US009480418B2

(12) United States Patent
Fausti et al.

(10) Patent No.: US 9,480,418 B2
(45) Date of Patent: Nov. 1, 2016

(54) SYSTEMS AND METHODS FOR THE SCREENING AND MONITORING OF INNER EAR FUNCTION

(71) Applicant: The United States Government as represented by the Department of Veterans Affairs, Washington, DC (US)

(72) Inventors: Stephen Fausti, Tigard, OR (US); Roger Ellingson, Portland, OR (US); Wendy Helt, Vancouver, WA (US); Peter Jacobs, Portland, OR (US); Grayson Silaski, Portland, OR (US); Debra Wilmington, Vancouver, WA (US); Samuel Gordon, Newberg, OR (US); Marilyn Dille, Vancouver, WA (US); Garnett McMillan, Portalnd, OR (US); Kelly Reavis, Portland, OR (US); Dawn Martin, Portland, OR (US)

(73) Assignee: The United States of America As Represented By The Department Of Veterans Affairs, Washington, DC (US)

( * ) Notice: Subject to any disclaimer, the term of this patent is extended or adjusted under 35 U.S.C. 154(b) by 0 days.

(21) Appl. No.: 14/989,613

(22) Filed: Jan. 6, 2016

(65) Prior Publication Data
US 2016/0113555 A1    Apr. 28, 2016

Related U.S. Application Data

(62) Division of application No. 13/842,880, filed on Mar. 15, 2013.

(60) Provisional application No. 61/624,097, filed on Apr. 13, 2012.

(51) Int. Cl.
*A61B 5/00* (2006.01)
*A61B 5/12* (2006.01)

(52) U.S. Cl.
CPC ............... *A61B 5/123* (2013.01); *A61B 5/121* (2013.01)

(58) Field of Classification Search
CPC ........ A61B 5/12; A61B 5/121; A61B 5/123; A61B 5/125
USPC ........................................................ 600/559
See application file for complete search history.

(56) References Cited

U.S. PATENT DOCUMENTS

| | | | |
|---|---|---|---|
| 6,602,202 B2 | 8/2003 | John | |
| 6,840,908 B2 * | 1/2005 | Edwards | A61B 5/121 600/559 |
| 7,133,715 B1 * | 11/2006 | Smits | A61B 5/04845 381/60 |
| 7,288,072 B2 * | 10/2007 | Stott | A61B 5/742 600/559 |
| 7,965,851 B2 * | 6/2011 | Bengtsson | A61B 5/0002 381/60 |
| 8,161,816 B2 * | 4/2012 | Beck | A61B 5/121 381/60 |
| 8,326,415 B2 | 12/2012 | Chan | |
| 8,340,757 B2 * | 12/2012 | Chan | A61M 21/00 600/559 |
| 8,394,032 B2 * | 3/2013 | Cromwell | A61B 5/121 600/559 |
| 8,529,464 B2 * | 9/2013 | Wasden | A61B 5/121 600/559 |
| 8,753,287 B2 * | 6/2014 | Bang | A61B 5/123 600/559 |
| 8,939,031 B2 * | 1/2015 | Gross | 381/60 |
| 9,138,178 B2 * | 9/2015 | Lee | A61B 5/121 |

* cited by examiner

*Primary Examiner* — Max Hindenburg
(74) *Attorney, Agent, or Firm* — Klarquist Sparkman, LLP

(57) ABSTRACT

Methods and systems for monitoring or testing the hearing of a user using a portable unit include presenting a plurality of test frequencies for selection by a user and storing data about those frequencies, and the user's response to stimuli presented at those frequencies, and comparing the stored data to previously acquired hearing data. Using mathematical prediction algorithms, changes in baseline hearing values can be used to identify potential hearing issues, especially hearing issues associated with ototoxicity.

7 Claims, 33 Drawing Sheets

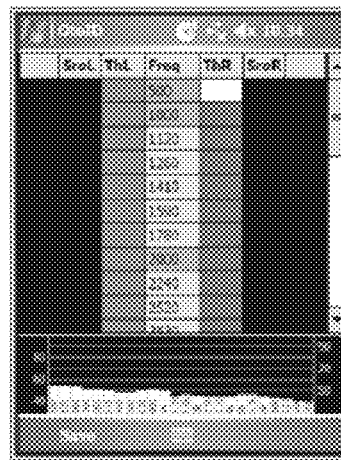 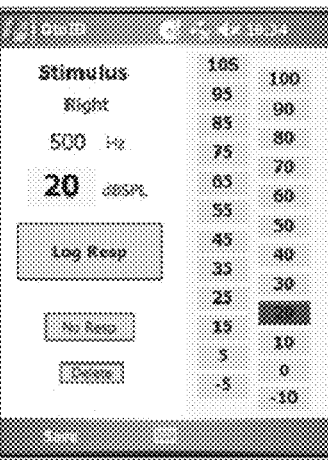 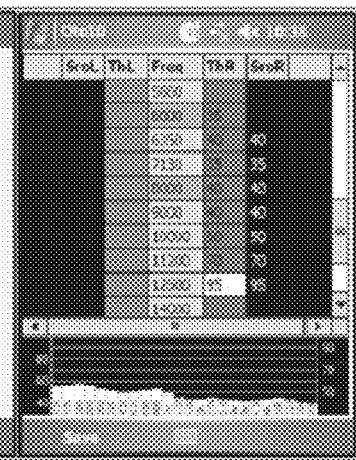
FIG. 2A    FIG. 2B    FIG. 2C
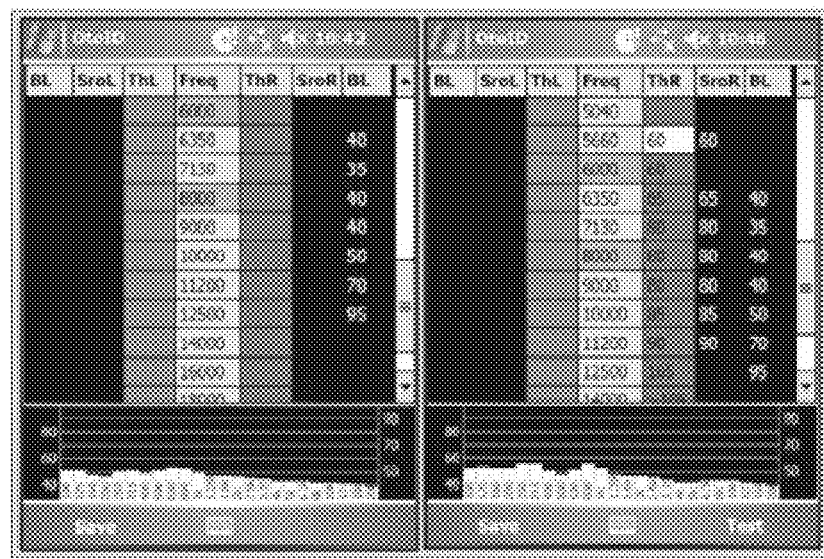
FIG. 3A    FIG. 3B Bias plot of the percent of automated (self-test) OtoID pure tone threshold (PTT) tests that are more than 5 dB from the manual (audiologist) test measurement taken on the same ear at the same time and place as a function of test frequency. Numbers in each panel indicate the number of separate visit measurements taken at each frequency.

Repeatability (% repeated tests within 5dB of initial test) of the manual (solid line) and automated (dashed line) OtoID protocols. Numbers in each panel indicate the number of separate measurements by ear taken at each frequency and range from a minimum of one to a maximum of 120 individual tests.

Characteristics of Subjects Administered Cisplatin from the Developmental and Validation Sample of Subjects

FIG. 19

| | Sample | | Total |
|---|---|---|---|
| | Developmental | Validation | |
| Total ears N | 45 | 24 | 69 |
| Total # patient × ear visits N | 155 | 62 | 217 |
| Pretreatment SRO avg (in dB SPL) Mean | 70.2 | 74.4 | 71.6 |
| Min | 49.6 | 52.9 | 49.6 |
| Max | 90.6 | 92.9 | 92.9 |
| Ears with one or more hearing change events N | | 9 | 31 |
| % | | 38% | 45% |

FIG. 20

Characteristics of Ears in the Developmental and Validation Samples

Results of the GEE Logistics Regression Analysis of Ears in Developmental Sample

FIG. 21

| Characteristic | | Statistic | Result | % |
| --- | --- | --- | --- | --- |
| Total Number of Subjects | | N | 22 | |
| Monitoring visits | | N | 71 | |
| | | Mean | 3.2 | |
| | | Min | 1 | |
| | | Max | 13 | |
| Visits with hearing change | | N | 31 | 43.7 |
| Age | | Mean | 62.4 | |
| | | Min | 51 | |
| | | Max | 79 | |
| Cancer Location | Bladder | N | 1 | 4.5 |
| | Head/Neck | N | 14 | 63.6 |
| | Lung | N | 6 | 27.3 |
| | Skin | N | 1 | 4.5 |

Characteristics of subjects and test sessions.

Results obtained for Freq 1 (higher) and Freq 2 (lower) relative frequency, stimulus level and ABR metric obtained at each treatment interval for subjects with or without ASHA-criterion hearing shift. ABR measurement failure rates also noted. (Stim levels in dBpeSPL; latency in ms and amplitude in nV)

| No. of metrics (K) | Metrics included in the candidate ORA |
|---|---|
| 1 | Dose-hearing model |
| 2 | 6 dB method+dose-hearing-model |
| 2 | Sum $\Delta OAE_f$+dose-hearing model |
| 2 | Maximum $\Delta OAE_f$+dose-hearing model |
| 2 | Mean $\Delta OAE_f$+dose-hearing model |
| 2 | PLS component 1+dose-hearing model |
| 3 | PLS components 1–2+dose-hearing model |
| 4 | PLS components 1–3+dose-hearing model |
| 5 | PLS components 1–4+dose-hearing model |
| 6 | PLS components 1–5+dose-hearing model |
| 7 | PLS components 1–6+dose-hearing model |
| 8 | PLS components 1–7+dose-hearing model |
| 9 | PLS components 1–8+dose-hearing model |
| 10 | PLS components 1–9+dose-hearing model |
| 11 | PLS components 1–10+dose-hearing model |

FIG. 32

|  |  | All |
|---|---|---|
| All | N | 19 |
| Patient ear-visits (post-baseline) | Total | 56 |
|  | Mean | 2.9 |
|  | Min | 1 |
|  | Max | 12 |
| Visits with hearing change | N | 23 |
|  | % | 41.1% |
| Age | Mean | 62.6 |
|  | Min | 51 |
|  | Max | 79 |
| Baseline SRO average threshold | Mean | 69.6 |
|  | Min | 43.6 |
|  | Max | 86.7 |
| Cancer Location |  |  |
| Bladder | N | 1 |
|  | % | 5.3 |
|  |  | All |
| Head/Neck | N | 12 |
|  | % | 63.2 |
| Lung | N | 5 |
|  | % | 26.3 |
| Skin | N | 1 |
|  | % | 5.3 |
| Starting Dose Level Cisplatin (mg/m$^2$) | Median | 100 |
|  | Min | 50.0 |
|  | Max | 100 |

FIG. 33

| Parameter | $w_i$ | Standard error | P-value |
|---|---|---|---|
| Intercept | −0.91 | 0.48 | 0.060 |
| Dose-bearing | 0.95 | 0.31 | 0.002 |
| C1 | 0.49 | 0.17 | 0.005 |
| C2 | 0.82 | 0.35 | 0.018 |
| C3 | 0.31 | 0.35 | 0.378 |

SYSTEMS AND METHODS FOR THE SCREENING AND MONITORING OF INNER EAR FUNCTION

CROSS REFERENCE TO RELATED APPLICATIONS

This is a divisional of U.S. application Ser. No. 13/842,880, filed Mar. 15, 2013, which in turn claims the benefit of U.S. Provisional Application No. 61/624,097, which was filed on Apr. 13, 2012; each of these applications are specifically incorporated by reference herein in their entirety.

FIELD

The present application relates to inner ear function screening and monitoring and, more particularly, to apparatus and methods for performing such screening and monitoring. For the purposes of this application, inner ear function refers to the sensation of hearing and the function of the sensory cells and spiral ganglion neurons that sub-serve this vital sensation.

BACKGROUND

Hearing loss screening and monitoring is an important part of general health monitoring. In addition, in some cases hearing damage can be reduced or prevented by early detection. For example, certain drugs, such as those used in the treatment of cancer, can be damaging to hearing, to auditory sensory cells and spiral ganglion neurons. Damage typically occurs first in the more basal regions of the cochlea which are specific for high-frequency hearing, and progresses to more apical regions that are relevant to speech understanding.

Monitoring of high-frequency hearing loss can be an effective means for early detection of hearing problems, including those caused by ototoxicity. Through early detection, for example, oncologists and others can adjust drug dosages or, alternatively, switch to medications that are less ototoxic. Despite substantial evidence and clear implications that preventing significant post-treatment hearing loss improves outcomes for patients, early identification and monitoring practices have not been implemented as a standard of care in most medical centers largely due to limitations in audiometric testing equipment. Currently available equipment requires patients to be seen in an audiology clinic for testing in a sound-attenuated room, which is generally not practical for patients undergoing treatment for cancer since these individuals often are severely ill or fatigued, or else live in rural areas and it is not realistic to expect them to return to the clinic to have their hearing tested. Accordingly, improvements in early hearing loss identification and monitoring to reduce and/or prevent permanent hearing loss are desirable. Because exposure to ototoxins and high levels of noise cause hearing loss primarily by damaging the outer hair cells and spiral ganglion neurons within the cochlea, non-invasive tests of outer hair cell function and neural survival are also needed.

SUMMARY

The systems and methods described herein are directed to improvements in early detection of inner ear damage, particularly identification and monitoring of ototoxic-induced hearing loss and sensorineural damage. In addition, the systems and methods described herein can also achieve improved detection and quantification of inner ear damage in applications other than those for early detection or ototoxicity monitoring. In some implementations, the systems and methods can be used to permit patients to monitor their own hearing using a device that alerts healthcare professionals in the event of a change in hearing.

For example, in some implementations, a portable audiometer is currently not available that is (1) capable of automatic or manual (by an audiologist) operation, (2) designed with precision pure-tone stimulus generation up to 20 kHz, and (3) able to remotely transfer health status information to a healthcare professional.

In one embodiment, a method for monitoring or testing the hearing of a user is provided. The method includes presenting a plurality of test frequencies for selection by a user through a display or acoustically, receiving indications of respective selections of test frequencies by the user, including indications of a right ear or a left ear that is to be tested at the respective selected test frequencies, causing an audio test unit to output one or more test sounds at respective ones of the selected test frequencies to the indicated ear, the one or more test sounds being output at one or more stimulus levels, and receiving an indication of whether the test sound was heard by the indicated ear at the selected test frequencies and, for instances where the test sound was heard, storing the stimulus level for which the test sound was heard. The highest set of test frequencies can be stored for which an indication was received that the test sound was heard by the indicated ear, with the highest set of test frequencies for each ear being the sensitive range for ototoxicity for that respective ear. Baseline values for each frequency in the sensitive range for ototoxicity for each ear can be stored, with the baseline value being based on the stimulus level at which the indication that the test sound was heard was received. The sensitive range for ototoxicity can be monitored for each ear by performing one or more subsequent hearing tests and comparing the baseline values for the respective sensitive range for ototoxicity with stimulus levels obtained from additional hearing tests. The method can include calculating whether any change from the baseline hearing values has occurred on one or more subsequent hearing tests using pre-determined criteria for a significant hearing change. The method can further include calculating whether a change from the baseline value is likely to occur with further exposure to a damaging agent using a mathematical prediction algorithm that includes the baseline hearing values and other risk factors for hearing loss.

In another embodiment, a portable hearing monitoring system is provided. The system can include an audio test unit configured to output one or more test sounds to an ear of a user and a hearing test control system configured to display the plurality of test frequencies on a display screen and receive indications of a selection of respective ones of the plurality of test frequencies. The audio test unit can be configured to deliver the one or more test sounds at a plurality of test frequencies and at a plurality of stimulus levels and the control system, upon receipt of an indication of a selected test frequency, can cause the audio test unit to output one or more test sounds at the selected test frequency to an ear at one or more stimulus levels. The control system can be configured to receive an indication of whether the test sound was heard by the indicated ear at the selected test frequency and, for instances where the test sound was heard, store the stimulus level for which the test sound was heard. The control system can also be configured to store the highest set of test frequencies for which an indication was received that the test sound was heard by the indicated ear along with a baseline value related to the stimulus level at which the test sound was heard. The highest set of test frequencies stored for each ear are the frequencies which are the sensitive range for ototoxicity for that respective ear.

The foregoing and other objects, features, and advantages of the invention will become more apparent from the following detailed description, which proceeds with reference to the accompanying figures.

BRIEF DESCRIPTION OF THE DRAWINGS

FIGS. 2A-2C illustrate exemplary testing applications for baseline hearing determination.

FIGS. 3A and 3B illustrate exemplary testing applications being used in a serial monitoring mode.

FIG. 19 illustrates the characteristics of subjects administered cisplatin from the developmental and validation samples.

FIG. 20 illustrates characteristics of ears in the developmental and validation samples.

FIG. 21 illustrates results of a GEE logistic regression analysis of ears in developmental sample.

FIG. 29 is a table of characteristics for subjects and test sessions.

FIG. 30 is a table illustrating results for Freq 1 (higher) and 2 (lower) relative frequencies, stimulus level, and ABR metric obtained at each treatment interval for subjects with or without ASHA-criterion hearing shift.

FIG. 32 is a table indicating candidate scoring functions and number of metrics contained within each function compared in this analysis. Each scoring function was evaluated using both the highest half-octave and highest quarter-octave DPOAE fine structure measurements in ⅛ octave steps.

FIG. 33 is a table showing study sample patient and treatment characteristics.

DETAILED DESCRIPTION

Figure 1:
FIG. 1 is an image of an exemplary hearing monitoring system, including a mobile application and a base unit, being used bedside to test hearing without transferring patient to clinic.

The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the terms "coupled" and "associated" generally mean electrically (wired or wirelessly), electromagnetically, and/or physically (e.g., mechanically or chemically) coupled or linked and does not exclude the presence of intermediate elements between the coupled or associated items absent specific contrary language.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernible, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Implementations of Personalized Systems and Applications for Monitoring Hearing Loss The systems and methods provided herein include mobile, full-frequency-range, auditory testing systems and methods which can provide detection of changes in hearing sensitivity including early detection of ototoxicity due to treatment with ototoxic medications. These systems and methods can be used efficiently in remote locations such as hospital wards, out-patient clinics, and industrial settings, as well as in patient homes. These systems and methods can also be used to monitor for any hearing change from other damaging sources, such as noise overexposure, and also to perform general audiometric hearing threshold testing at any desirable range, such as up to about 20 kHz which is generally considered to be the upper limit of the audible range for humans.

These systems and methods can also be desirably used in connection with the Sensitive Range for Ototoxicity (SRO), a shortened serial hearing monitoring protocol which has been shown sensitive and reliable in detecting early hearing change. A functional overview of the systems and methods designed to support the SRO hearing monitoring protocol is provided herein, including a description of exemplary implementations of mobile software applications. In these exemplary implementations, serial monitoring information for an actual patient is used to illustrate how the exemplary software application can be used to provide detection and monitoring of hearing change, including early detection of ototoxicity, noise overexposure or traumatic brain injury. Analysis of the patient's SRO monitoring data demonstrates the system's efficacy in detecting hearing threshold change. Overviews of other support applications are also provided, including one used for system calibration in the acoustics laboratory and one used for acoustic performance verification in the field.

Moderate to profound hearing impairment due to treatment with ototoxic medication and excessive noise exposure affects millions of people but can be avoidable through prevention, early diagnosis, and management. Research showing initial hearing change occurs first at the upper frequencies of human hearing range (>8 kHz to 20 kHz), and if untreated, progresses down into lower frequency ranges, eventually impairing communication ability.

Research has identified a one octave range of hearing individualized to each patient's high frequency limit of hearing, called the sensitive range for ototoxicity (SRO), which is able to detect 94% of early changes in hearing during treatment. The SRO is obtained by initially testing hearing from 0.5-20 kHz to find the highest frequency at which a threshold of 100 decibels (dB) of sound pressure level (SPL) is obtained. Thresholds in the next six consecutive lower frequencies, measured in ⅙th octave steps, comprise the SRO. The initial baseline test is done prior to treatment. Then, at each chemotherapeutic treatment interval, these seven SRO frequencies are measured for hearing shift. The SRO technique is both time efficient and has been proven to be sensitive to early effects of cisplatin in the cochlea.

An exemplary method for obtaining the SRO of a patient is set out below:

1. Establish baseline hearing thresholds across full range of human hearing at ⅙ octave frequency steps.

2. Identify SRO frequency set: composed of the seven consecutive highest frequency thresholds <105 dBSPL.

3. Monitor SRO frequency set for change, defined as: 1) ≥10 dB change at two consecutive frequencies, 2) ≥20 dB change at any one frequency, or, 3) no response at three consecutive frequencies which previously had responses.

The SRO protocol is highly personalized in that each person has their own set of frequencies that will be monitored for hearing change. This reduces the number of frequencies needed to test during monitoring, therefore reducing testing time.

The SRO protocol is a time efficient and reliable method to detect hearing change due to ototoxic medication. It can also be useful in detecting hearing change due to other factors, such as, for example, hearing loss due to excessive noise exposure. Unfortunately there are currently no commercially available systems designed to provide efficient and reliable early detection of hearing change in clinical settings, let alone the mobile environment. Moreover, conventional hearing loss screening products are generally capable of only performing routine clinical audiometric testing, primarily in the speech frequency range of 250 Hz to 8 kHz. To properly administer the SRO protocol, however, requires full-frequency range testing out to 20 kHz, in ⅙ octave steps at acoustic levels up to 105 dBSPL. Note, throughout this application, dBSPL is referenced to 20 uPa which is considered the threshold of hearing for healthy individuals. 93.8 dBSPL=1 Pa which is approximately as loud as a passing truck at a distance of 10 ft. An increase of 10 dB is generally perceived as twice as loud.

The systems and methods disclosed herein provide robust mobile instrumentation that is capable of providing detection of hearing change efficiently and reliably. These systems, such as the novel remote monitoring system illustrated in FIG. 1, are collectively referred to herein as the Ototoxicity Identification (OtoID) system. Although the reference to the device as "OtoID" obviously reflects a particular application target area (i.e., ototoxicity monitoring), it should be understood that the system described herein can also be of high utility for other purposes, such as audiometric devices capable of supporting general hearing testing, and the use of the term "OtoID" is not intended to limit the scope of the invention.

The OtoID system can comprise a small handheld portable computing device (PDA) and audiometer-like base unit with headphones. A base unit, such as is shown in FIG. 1 and described in more detail below, can be a battery-powered, audiometric-type stimulus generator with sufficient stimulus frequency range (e.g., 500 Hz to 20 kHz at ⅙ octave stepping) and quality (−10 to 105 dBSPL spurious-free acoustic transducer dynamic-range output measured with IEC318 artificial ear). The base unit, together with an audiometer-like stimulus control application, can function to obtain reliable full-frequency range hearing thresholds. The base unit can also be capable of measuring background ambient noise and verifying acoustical performance at ⅓ octave band intervals.

As shown in FIG. 1, the base unit can be controlled by a remote device, such as a smartphone or other such multifunction computing device. In the exemplary embodiment, the device comprises a computing device with a touchscreen that can receive inputs from a user either by contact with a finger or other selecting device (e.g., a stylus). Of course, other input means and devices can be used to control operation of the base unit. For example, personal computers, laptop computers, or other computing devices can be provided with one or more other physical user-interface devices, such as a physical click wheel, a physical keyboard, a mouse and/or a joystick. Instructions can be conveyed from the computing device to the base unit via various communication protocols.

The OtoID system can include SRO-monitoring specific software applications running on the PDA device. Such applications can wirelessly control the audiometric base unit. In one implementation, a main program, referred to herein as "OtoID.exe", can be used for hearing testing. Two other supporting applications, referred to herein as "OtoIDcal.exe" and "OtoIDchk.exe", can be used for acoustic calibration. Acoustic calibration actions (e.g., OtoIDcal.exe) can involve access to a sound level meter and artificial ear with acoustic headphone coupling device, and acoustic performance checking (e.g., OtoIDchk.exe) can involve an acoustic performance verification in the field.

In the exemplary embodiment, these applications are implemented in the C# programming language in the Microsoft®.Net Compact Framework environment and share a common basic user interface. The programs can also be all database driven in that system parameters, calibration values, and testing results are contained in one PDA database file. The programs also support viewing and saving detailed testing results and logging information to text and spreadsheet-format output files providing simplicity of access preferable to some users. The Windows Mobile®-based PDA environment has extensive built-in operating system support for networked data transfer and remote-application development-tools supporting tele-health models of care-delivery. Results of any test, including, for example, an audiogram, can be output to a printer or other display mechanism or exported to another program or system for analysis and/or storage.

The systems and methods disclosed herein can also include support for time-stamped, ⅓-octave-band ambient-noise and acoustical performance measurements. The ambient noise measurement and recording feature can be configured to verify that testing conditions in remote locations are suitably quiet when obtaining threshold data. In one embodiment of the invention, the ambient noise can be canceled using a technique called active noise cancelation. Active noise cancelation measures the incoming noise waveform and sums that waveform with an equal amplitude waveform that has its phase inverted from the incoming waveform. The test sound that is presented to the user's ear is theoretically not contaminated by the ambient noise source.

Prior to performing any testing, the user can select and/or enter subject, operator, system, and location parameters. This selection/entering can be achieved in various manners, including by using a drop-down menu to select previously-entered values. Then the user can select the action that is to be taken, such as "new baseline session", "selecting baseline for monitoring", and/or selecting, saving, viewing, deleting, and/or modifying any previous results.

Figures 4A, 4B:
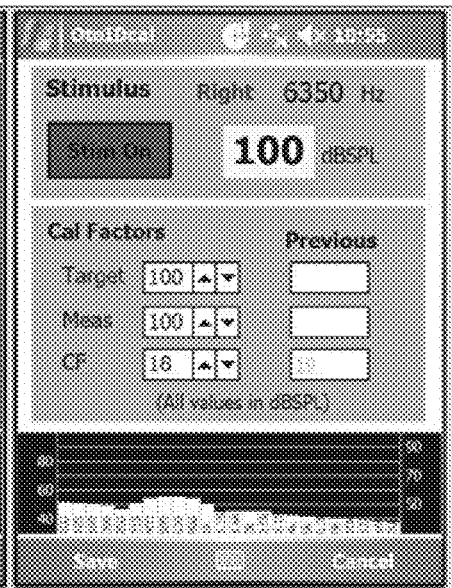
FIGS. 4A and 4B illustrate exemplary applications for performing acoustic calibrations.

The OtoID.exe program can be used for both baseline determination and serial monitoring of hearing. FIGS. 2A-2C illustrate various embodiments of control screens in a baseline mode and FIGS. 3A and 3B illustrate various embodiments of control screens in a monitoring mode. As discussed above, the OtoIDcal.exe application can be used for system acoustical calibration, and FIGS. 4A and 4B illustrate various embodiments of the interface and operation of the calibration systems.

FIGS. 2A-2C illustrate an exemplary testing application for making baseline hearing determinations using OtoID.exe. For example, after selecting and/or entering test session, subject, operator, system, and location parameters (not shown), the operator can be presented with a central testing control grid shown such as is shown in FIG. 2A. Upon selecting the testing frequency and ear that is to be tested (e.g., 500 Hz, 1000 Hz, and/or 2000 Hz; ThL or ThR), a test stimulus control panel can be displayed as shown in FIG. 2B. The base unit can be configured to present testing stimuli to the subject when the operator selects a level selection box. When a threshold has been obtained at that frequency, the operator can select "Log Resp", "No Resp", or "Delete" to record the threshold if found or not found or to delete the existing threshold. The SRO value can be generated and indicated on the display as shown in FIG. 2C for the respective ear (e.g., SroL or SroR).

The operator can return to the testing control grid shown in FIG. 2A after pressing "Save" menu item. As thresholds are obtained, the testing control grid shown in FIG. 2C is filled in. The system can be configured to automatically calculate and display the SRO in the ear's SRO column when enough thresholds have been recorded. Time-stamped, one-third-octave ambient noise bands, unlimited in number, are obtained from the base unit microphone measurement system and displayed and recorded along with testing data every time the operator presses in the display area.

FIGS. 3A and 3B illustrate the testing application (OtoID.exe) being used in an exemplary serial monitoring mode. As shown in FIG. 3A, after selecting parameters and baseline sessions (not shown), the operator can be presented with a testing control grid already filled in with baseline SRO results in the "BL" columns. Test frequencies can range from 500 Hz to 20 kHz at ⅙ octave stepping (plus 3 kHz and 6 kHz standard frequencies if desired). As testing progresses, the system can generate current SRO values (SroL and SroR). A bar graph can indicate logged ⅓ octave ambient noise.

As shown in FIG. 3B, operation can be generally identical to the baseline testing method with the serial monitoring SRO appearing in the "SRO" columns when obtained. Note that the SRO frequency shift shown in FIG. 3B indicates decreased hearing sensitivity. Also, because 6000 Hz is not a ⅙ octave frequency, it is not included in the SRO calculation.

As discussed above, OtoIDcal.exe can be used for system acoustical calibration. An exemplary interface for the system acoustical calibration is illustrated in FIGS. 4A and 4B. In order to perform reliable hearing threshold testing, it is desirable to establish and maintain calibrated acoustic-stimulus levels. This is preferably performed in a hearing clinic initially and at subsequent weekly or bi-weekly intervals by professional acoustics consultants or audiologists familiar with calibration procedures for a particular audiometer using precision acoustical references and known acoustic-transducer transfer characteristics.

Support program can be provided to acoustically calibrate system with traceable calibration equipment. In one exemplary method of performing calibration, the operator can place the appropriate headphone transducer on an acoustic coupler that is connected to a sound level meter indicating traceable dBSPL acoustic amplitudes. After selecting various calibration parameters (not shown), the operator can be presented with a control grid for frequency and ear calibration point selection as shown in FIG. 4A. Upon selecting a cell, the calibration point control form is presented as shown in FIG. 4B. The operator can select "Stim On" to turn on non-pulsing pure-tone stimulus and adjust the calibration factor ("CF") box until the sound level meter reading equals the "Target" level. Upon selecting "Save", the CF values are stored in the system database and base unit. Upon hearing monitoring testing application startup, the CF values are downloaded into the base unit. Ambient noise measurements are recordable as desired to document calibration conditions. In one embodiment, the OtoID achieves an operator-assisted calibration procedure by utilizing a Type I sound level meter and IEC318 artificial ear with flat plate circumaural headphone coupling adapter.

Figures 5A, 5B:
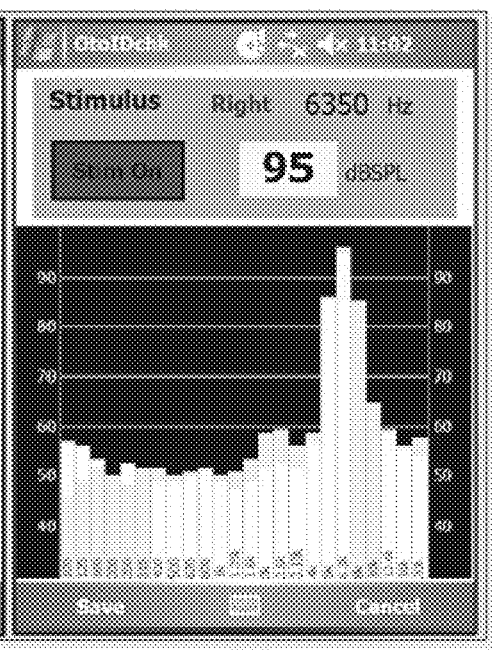
FIGS. 5A and 5B illustrate exemplary applications for verifying system acoustical performance in remote locations.

OtoIDchk.exe can be used to verify system acoustical performance in field locations using previously-verified reference spectrum values for each transducer and testing frequency. In some embodiments, support program used to verify system acoustical performance in remote locations without requiring external calibration equipment. The operator can place the headphones over the base unit and uses the interfaces and methods as shown in FIGS. 5A and 5B to verify the selected frequency and ear stimulus performance.

In one exemplary method, the operator places the headphone over the base unit case which contains the acoustic microphone measurement system. Upon entry, a testing control grid of frequency ear values is presented as shown in FIG. 5A. Selecting a cell (e.g., 6350 Hz) brings up the performance point form as shown in FIG. 5B. A 95 dBSPL pure tone, non-pulsating stimulus can be delivered out the headphone when the operator turns on the stimulus by pressing "Stim On". Touching the one-third octave display area collects a sample and displays the new set of yellow-colored band result bars. Should there have been a previous (performance check baseline) set of values in the database it would have been already displayed in white-colored bars in an overlaid manner to verify system integrity. Using this method one can visualize changes in acoustic performance that could affect field testing results. Upon "Save" the control grid (a) contains the new "Meas" (measured dBSPL) and "PB" (peak band frequency) result along with the previous baseline performance check values if they existed. Full performance-check band-data is also stored in the system database.

Figure 6:
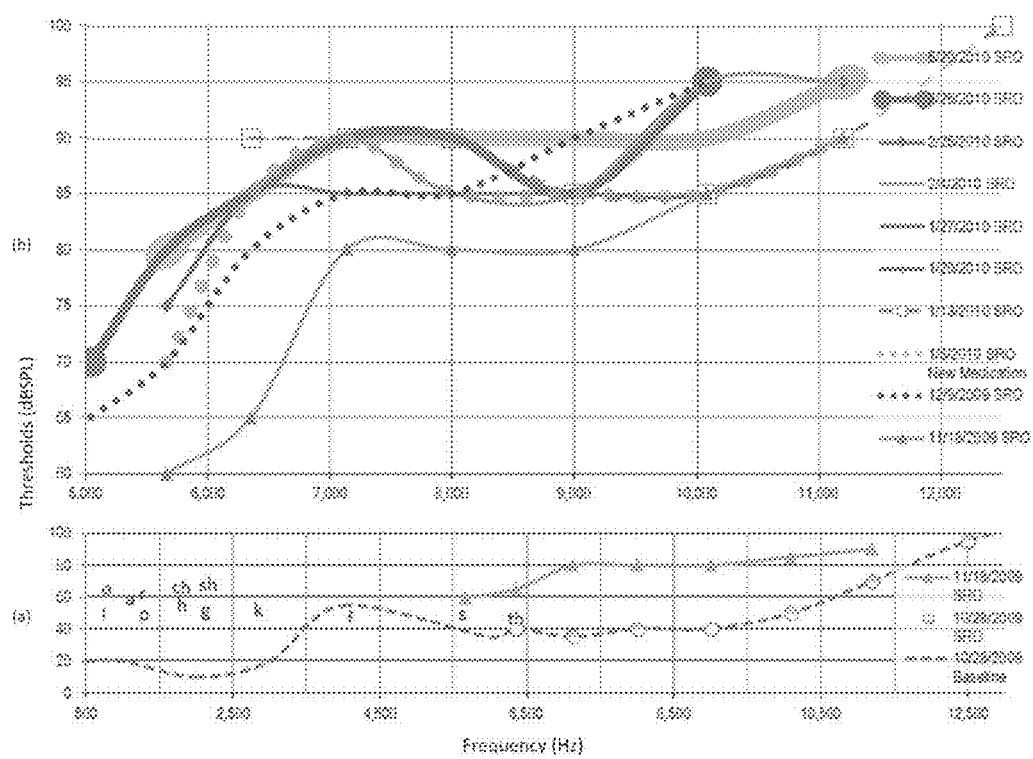
FIG. 6 illustrates SRO baseline and serial SRO monitoring results for individual study participant undergoing chemotherapy treatment, with the SRO being equal to the uppermost seven consecutive ⅙ octave frequencies with thresholds <105 dBSPL.

FIG. 6 illustrates the baseline and serial monitoring results for a cancer patient at risk for ototoxic hearing loss. Based upon SRO monitoring results, a significant change in hearing was rapidly detected soon after chemotherapy had begun. The rapid decrease in high frequency hearing sensitivity was apparently due to ototoxic medication. Upon follow-up with the attending physician, and based upon these and other indications, a medication change was made. Within weeks the progression of the patient's hearing loss slowed, then stopped, with hearing sensitivity eventually stabilizing, preventing further hearing loss in the patient.

The lower graph (a) in FIG. 6 illustrates baseline hearing configuration overlaid with baseline SRO frequencies. SRO monitoring results three weeks later (on Nov. 18, 2009) show a significant shift indicating severe decrease in hearing sensitivity. As shown in FIG. 6, the individual presented a hearing "notch" (i.e., an abrupt decrease followed by increase in hearing sensitivity) at 4000 Hz. The letters on the lower graph chart represent normal English speech phoneme presentation levels. Two speech phonemes, 's' and 'th', illustrate the effect ototoxicity can have on speech communication—within 3 weeks after chemo treatment, the subject would be unable to hear important components of words being spoken at normal levels. The notch in the 'f' region indicates potential hearing difficulty even before treatment.

The upper graph (b) in FIG. 6 shows further decreased hearing sensitivity in SRO(Dec. 9, 2010) which was after SRO(Nov. 18, 2010). After that date, the medication was changed and SRO(Jan. 6, 2010) indicates that the progression of hearing loss is slowing at upper frequencies, and SRO(Jan. 13, 2010) indicates some stabilization of hearing loss. Follow-up 12 week SRO(Mar. 26, 2010) indicates stabilization of hearing except for a general range frequency shift downward. Follow-up 20 week SRO(May 20, 2010) shows recovery at upper SRO frequency, shifting SRO range up on frequency step, but continues to indicate stabilization of hearing loss. SRO(Jan. 20, 2010) to SRO(Feb. 25, 2010), though difficult to identify, are included as measures of monitoring reliability.

Average testing time per serial monitoring visit can be approximately 10 minutes. The short testing time using the SRO protocol and the ability to test patients at various locations (e.g., at bedside in the chemotherapy ward or elsewhere instead of transferring to and from a hearing clinic) is a great advantage for those for whom travel can be difficult, such as cancer patients who can be feeling quite ill after treatment. Conventional systems that require patient transport can take significantly longer, since not only is there additional transport time required, but also patients must be prepared for transport and additional time taken to receive them upon return. Moreover, reducing travel requirements can also reduce exposing compromised patients to health risks relating to the additional transport or travel.

There is a need for clinical and mobile hearing-testing systems capable of detecting hearing change due to ototoxic medication or other factors such as on-going noise exposure. Research has shown the SRO protocol is an efficient, sensitive, and reliable method capable of early detection of ototoxic hearing change. The method requires full-frequency-range audiometric instrumentation which is not readily commercially available. The systems and methods described herein are capable of providing sensitive and reliable full-frequency-range hearing testing. In addition, the exemplary mobile software applications described herein not only efficiently support general ultra-high-frequency audiometric testing, but also effectively implement a novel computer-assisted SRO monitoring system. The system also has unique ambient-noise and acoustical performance measurement features which can be particularly helpful to ensure accurate operation in remote locations.

The innovative mobile instruments and methods of use of the same, moves testing out of the hearing clinic and into the hospital, the bedside, the home, or any remote location. This advancement is saving clinician time, patient transfer time, and nursing time. It is also more comfortable for the ill patient and is of less risk to patient health.

Implementations of Portable Telemedicine Audiometers and Methods of Using the Same The OtoID includes a portable audiometer with high frequency test functionality that meets ANSI/ASA S3.6-2010 standards and that is capable of reliably detecting a person's drug-related hearing changes relative to a baseline period (i.e., before they have received ototoxic drugs) using an automated test. In addition to the high-frequency audiometer, as described herein, the system can also include a wireless cellular modem that is capable of notifying a remote healthcare professional in the event that a significant change in high-frequency hearing has occurred in the patient. This system was evaluated on 9 test subjects and the results indicate that the OtoID system can be used by patients to effectively monitor high-frequency hearing changes remotely within their home, ultimately enabling early detection of ototoxic damage and potentially avoiding hearing loss.

Certain cancer-treating drugs such as cisplatin and carboplatin are considered to be ototoxic in that they have the potential to irreversibly damage a person's hearing. Cisplatin, the most ototoxic agent, results in hearing shift during treatment in approximately 60% of adults and children. Risk factors for ototoxicity are pre-exposure (to cisplatin) hearing threshold levels and cumulative cisplatin dose such that those with better hearing are more likely to have hearing shift at lower cumulative doses than those with poorer hearing. This can be helpful since individuals, such as older adults, often begin chemotherapy with significant hearing loss. Therefore, any hearing change has immediate impacts on their communication at a time when effective communication with family members and the medical team is important.

Ototoxic damage initially occurs near the high frequency-coded base of the cochlea before progressing apically to the lower frequency regions that are more relevant for speech understanding. Ototoxic-induced changes in hearing can only be detected by assessing auditory function directly. Early detection of ototoxicity is important since it has the potential to minimize the significant negative effects of increased hearing loss following treatment by providing an opportunity for oncologists to adjust treatment protocols or to change to less ototoxic chemotherapeutic agents. If dosage adjustment is not possible, the audiologist can plan for intervention strategies that include assistive listening devices/strategies as well as counseling relating to avoidance of loud noise exposure, which acts synergistically with drug exposure to cause damage.

In order to detect ototoxicity, hearing must be tested. Currently there are no commercially available portable audiometers capable of supporting high SPL output with required signal purity for accurate testing up to 20 kHz in ⅙th octave steps, a requirement for the SRO protocol. Portable audiometry would provide for bedside testing of patients during treatment and home testing post-treatment. In order to reduce healthcare costs, a portable device that has the capability for self-testing (automated testing mode) would provide an alternative to requiring all facilities provide professional staff capable of accurately testing hearing for ototoxicity monitoring purposes.

Finally, clinical testing at treatment intervals which can be 2-3 weeks apart may not provide earliest detection of hearing shift. Technological advances have allowed telemedicine to improve access, effectiveness, and efficiency of many aspects of healthcare, and have the potential to permit auditory testing. Telemedicine not only enables healthcare delivery outside of centralized settings, but also allows minimally trained healthcare professionals or patients to monitor indicators of health, thus increasing patient access to healthcare. Providing technology that would permit auditory testing at home or in the field by the patient utilizing telemedicine technology to deliver the results via a secure HIPAA-compliant network to the health care team would improve healthcare access for all patients, particularly those in rural or remote areas. Informed decisions regarding upcoming treatment or plans for aural rehabilitative strategies to improve communication could then be made.

The OtoID systems and methods address this clinical need by optimizing the access, efficiency and cost-effectiveness of ototoxicity early identification practices. The OtoID includes a monitoring system with the ability to transmit information to healthcare personnel where trained professionals would interpret the results. In addition, the OtoID system can include automated test functionality for self-evaluation of ototoxicity damage and achieves high quality audio based on an analog oscillator circuit, optical muting capability, discrete attenuators, ambient noise monitoring and other features necessary for meeting the ANSI/ASA S3.6-2010 specifications.

The OtoID system can be used within the home or clinic and can be capable of performing patient-guided conventional and extended high-frequency (9-20 kHz) audiometric testing for the purpose of determining damage from ototoxic drugs. In some embodiments, the OtoID systems can be used within a home or clinic and can include functionality that can notify remote medical personnel of testing results through a provided communication system, such as an on-board cell phone module. In addition, the communication systems provided herein can be fully HIPAA compliant.

Design of the high-frequency audio functionality and the telehealth components of the system are discussed. For convenience, the performance of the OtoID is compared with a non-portable Grason-Stadler Model 61 (GSI-61) clinical audiometer with high frequency options. The system was evaluated on 9 young normal-hearing listeners over the 0.5-16 kHz frequency range (high frequency limit of GSI-61). Results indicate that the OtoID favorably compares with commercially available audiometers used for clinical testing in both the conventional (250-8 kHz) and extended high frequency range (8 kHz-16 kHz). Furthermore, test subjects are able to accurately self-evaluate their hearing within the frequency ranges and step-sizes needed for ototoxicity monitoring.

The widespread implementation of ototoxicity monitoring best practices will provide the opportunity to minimize progression of hearing loss into the speech communication range, ultimately improving outcomes for patients and preserving the quality of their life following treatment.

Figure 7:
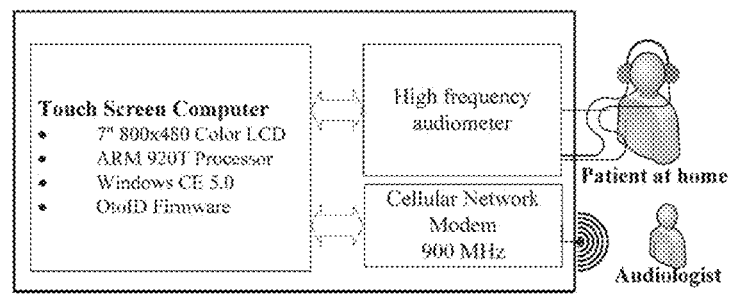
FIG. 7 illustrates a system overview of an exemplary system for monitoring and/or detecting hearing loss.

FIG. 7 illustrates an exemplary schematic architecture of a system comprising a PDA and a base unit. As noted above, the base unit and PDA can communicate via a communication protocol using respective wireless interfaces. The PDA can run various programs which can control the operation of the base unit and receive data from the base unit. The implementation and operation of the novel methods disclosed herein (e.g., the exemplary software applications) can efficiently guide a trained practitioner in administering the SRO protocol to individuals at risk for hearing damage in remote locations. Actual, single-patient, serial monitoring data is disclosed herein to illustrate program operation and demonstrate system sensitivity and reliability in early detection of hearing change.

As shown in FIG. 7, the OtoID system can include (1) an ARM-based processor with a touchscreen 800×480 pixel color LCD monitor running Windows CE and the OtoID firmware, (2) a custom audiometer with high frequency capability printed circuit board (PCB) for generating pure-tone high frequency audio and measuring ambient noise, (3) high frequency Sennheiser HDA 200 modified earphones, and (4) a Verizon Multitech (MTSMC-C1) 900 MHz cellular network modem, which is used for transferring diagnostic results to a health care professional such as an audiologist. The audiometer, touch screen computer, and cellular modem can be combined in a custom designed ergonomically styled portable package with a protective carrying case. Such portability can be particularly beneficial to enable a patient to detect ototoxic damage within their home.

Figure 8:
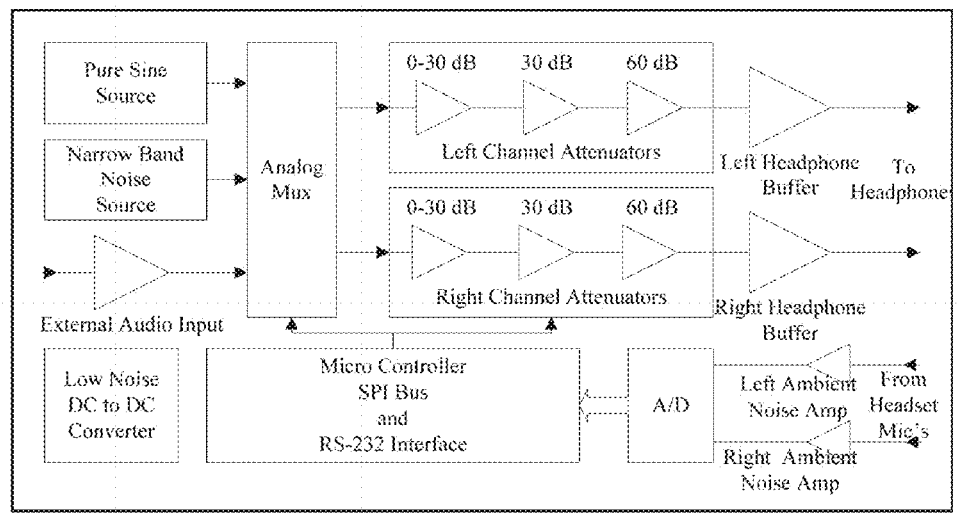
FIG. 8 illustrates a schematic block diagram of an exemplary audiometer with high-frequency capability that can be used with the novel system for monitoring and/or detecting hearing loss.

FIG. 8 illustrates a block diagram of an exemplary audiometer. The audiometer module shown in FIG. 8 was designed for compliance with ANSI S3.6-2010 Pure Tone Type 4 and Type high frequency (HF) requirements for audiometers. Subsequent testing indicates compliance with this standard.

Elimination of Artifacts. Suppressing or eliminating unwanted acoustical signals (e.g. hiss, clicks, pops, hum, beeps) is a difficult challenge in the design of audiometric instrumentation with high frequency capability. Patients often have a reduced hearing threshold in the high frequency range. Any unwanted acoustical signals that might be unintentionally presented along with the stimulus could easily be perceived and incorrectly reported as a positive response. A similar problem is posed when electrical crosstalk between left and right channels is present, and stimulus from one channel finds its way into the other (especially when the spectral content of the two channels differ significantly).

In addition to producing stimuli of very high quality, the OtoID audiometer employs a number of measures to ensure that the audio channels remain free of any unintended sounds or artifacts, even at high output levels up to 105 dB SPL. Techniques were also employed to minimize channel crosstalk, and to ensure the channels are not contaminated by any noise emanating from digital electronics employed in the system.

Figure 9:
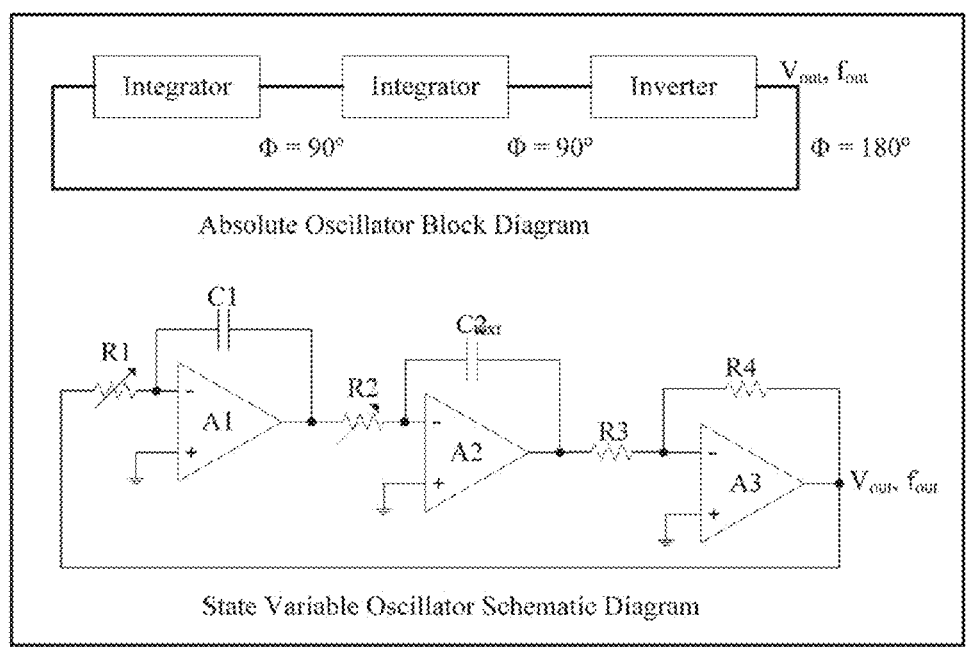
FIG. 9 shows the block diagram of an absolute oscillator.

Analog Pure-Tone Generator. FIG. 9 shows the block diagram of pure tone oscillator circuitry of a basic absolute oscillator that consists of two integrators and one inverting amplifier. Each integrator provides 90° of phase shift and the inverting amplifier provides an additional 180° of phase shift that is fed back into the first integrator to reinforce the oscillation. FIG. 9 also shows the simplified schematic for the State Variable Oscillator used in the OtoID. Op amps A1 and A2 are configured as integrators and op amp A3 is configured as a unity gain inverter. The equation to calculate the frequency of oscillation (Fout) is given below.

$$F_{out} = \frac{1}{2\pi}\sqrt{\frac{R_4}{R_1 R_2 R_3 C_1 C_2}}$$

Variable resistors $R_1$ and $R_2$ are used to vary the frequency. The actual implementation of the variable resistors can be accomplished using precision 12 bit multiplying DACs (TIDAC7811). The DACs are programmed by the system microcontroller as needed. With this approach, 4096 different frequencies can be selected by the controller on the audiometer board. The two pure tone generators in the audiometer are designed around high quality, analog state variable band pass filters. Precision automatic gain controls provide unity gain feedback and configures the filter to operate an ultra-stable, sine wave oscillator of exceptional quality. This type of analog oscillator eliminates the spurious artifacts, distortion, and transients commonly encountered when producing sine waves using digital waveform synthesis.

The high performance operational amplifiers (AD8674) used in the sine wave oscillators ensure low output distortion and low random noise. Passive components insensitive to temperature are used to ensure a stable output frequency and consistent signal level.

Optoelectronic Muting Circuits.

The OtoID audiometer enables the switching of the stimulus on and off in a controlled and completely noiseless manner (Section 5.4.4 of ANSI/ASA S3.6-2010). The OtoID audiometer design employs optoelectronic components called VACTROLs® which are tiny assemblies that contain both an infrared LED light source and a Cadmium sulfide (CdS) photoresistive cell. These devices are positioned inside the Vactrol so that light from the LED illuminates the surface of the CdS cell. The resistance of a CdS cell will vary according to the amount of light energy illuminating its surface, thereby acting as an ideal continuously variable resistor.

Figure 10:
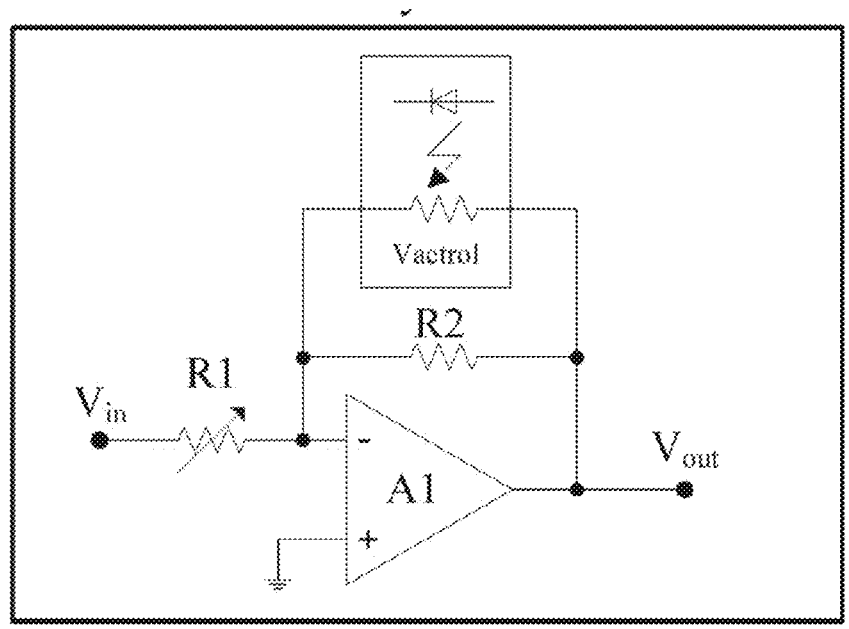
FIG. 10 illustrates a circuit diagram of circuitry digital attenuator circuit that uses VACTROL switches to quietly switch attenuator levels.

FIG. 10 illustrates a circuit diagram or a circuitry digital attenuator circuit that uses VACTROL switches to quietly switch attenuator levels. As shown in that simplified schematic of one of the attenuator blocks of the audiometer, op amp A1 is configured as an inverting amplifier whose gain is given by $-R_2/R_1$ where $R_2 < R_1$. For example if R2=R1/100 then the amount of attenuation would be 40 dB. The VACTROL® resistive element is connected in parallel to R2. The dark resistance of the photoresistor is much greater than the value of R2. Increasing the current through the LED will proportionally decrease the resistance of the photoresistor until its resistive value is much smaller than that of $R_2$ effectively reducing the gain of the stage to nearly zero. By using a multiplying 12 bit DAC (TI DAC7811) in the place of $R_1$ a digitally controlled attenuator is created.

The VACTROLs® are positioned at specific points within the six audio attenuator circuits, and by switching the LED illuminators on and off, audio stimuli can be fully attenuated (muted) and restored (un-muted) at a controlled rate. The microcontroller in the audiometer modulates the VACTROL® LED current so that light levels change on the CdS cells, which in turn controls the rise and fall rate of the CdS cell resistance. Using this method, the audiometer can provide calibrated stimulus rise and fall times in compliance with ANSI/ASA S3.6-2010 7.5.3. The ideal variable resistance of the VACTROL® CdS cells in the attenuator circuits produces a completely clickless and noiseless way to switch stimulus on and off (whether presenting a single stimulus or continuously pulsed).

Discrete Attenuator Circuits. The left and right attenuators in the audiometer are of a discrete, distributed design. While there are commercially available, integrated solutions for attenuating audio signals, none of these have the required distortion and crosstalk performance suitable for use in high frequency audiometric instrumentation.

Each discrete attenuator consists of three stages that are physically separated in order to prevent crosstalk that could negatively affect attenuation linearity over the required 120 dB range of human hearing. The first stage is adjustable over a range of 0 to 30 dB in 0.1 dB steps. A precision, current mode digital-to-analog converter (TI DAC7811) is used for the fine adjustment provided by this first stage. The second and third stages are fixed at 30 and 60 dB respectively, and either or both of these can be switched out. These three stages incorporate precision operational amplifiers (Analog Devices AD8671) to provide excellent signal-to-noise and low distortion performance required for a pure-tone audiometer.

Headphone Buffers and Output Pads. The final output stage on the audiometer channels is optimized for driving headphone impedances as low as 10 ohms (e.g. Etymotic ER-2). An integrated high performance, high current audio buffer (National Semiconductor LME49600) is incorporated into the feedback loop of the third attenuator stage combining the benefits of a low noise, bi-polar output stage, and a high-precision, high-speed operational amplifier.

Ambient Room Noise Detection. The OtoID includes a modified set of Sennheiser HDA 200 audiometric headphones. The Sennheiser HDA 200 is a closed-back, stereo headphone providing a wide frequency response suitable for high frequency audiometry. The "around the ear" ear cup design of the HDA 200 is based on PELTOR hearing protectors, and provides a high level of ambient noise isolation. The headphones were modified by building an omnidirectional electret microphone (CUI Inc., CMA-6542TF-K) into each ear cup for the purpose of sensing ambient noise. The electret microphones are flush mounted in the ear cup housing to maintain an airtight integrity of the cup, and face into the test room. A cable is run from the microphone to the OtoID audiometer where the signal is amplified, converted to a DC signal with a rectifier circuit, and then digitized using a 10-bit analog-to-digital converter. A firmware algorithm in the audiometer processes the digitized microphone signal using a "leaky integrator" topology where the signal is continually integrated, with a small portion of the result subtracted on a continuous basis, effectively resetting the integrator over time. Finally, the firmware algorithm traps particular events where the integrated signal exceeds a set level, which can be adjusted to suit the particular needs for a given test environment.

Unified Switching Power Supply. The audiometer incorporates a built in DC to DC power converter with a fixed operating frequency, and multiple outputs, each with its own LC filter. This DC to DC converter also serves to maintain a degree of electrical isolation between the audiometer board and additional devices powered from the same AC adapter (touch screen computer and cellular radio modem). The fixed frequency operation of the power converter combined with the LC filter networks minimize power supply noise and ripple on the analog power supply rails that can interfere with the signal quality on the audio channels. The switching flyback topology of the converter permits the audiometer to operate from a single external power source from 8 to 14 VDC. A medical-rated, 12 VDC output source from 8 to 14 VDC. A medical-rated, 12 VDC output adapter is currently employed, with the provision for conversion to battery operation in future.

Multiplexed Digital Links to Analog Circuits. The microcontroller (Microchip. PIC18F42520) in the audiometer controls several analog functions (including attenuators and the pure tone oscillator itself) using an industry standard synchronous serial communication link called the Serial Peripheral Interface (SPI) bus. Each noise sensitive analog circuit function group has its own dedicated SPI communication link with the microcontroller. This reduces the potential of the digital signals interfering with the precision analog waveforms being generated. After the controller has changed the settings in a noise sensitive circuit the SPI bus is halted thereby eliminating the possibility of digital crosstalk into this circuit. There are a total of four separate SPI links in the audiometer design, each multiplexed to the microcontroller.

Communication Baud Rate. The OtoID incorporates a 38.4 kbps RS-232 serial communications link to the touch screen computer. The Baud rate was chosen to prevent unintended heterodyning with high frequency stimuli. Such a phenomenon, if it occurred, could result in frequency shifted components (in the range of normal sensitive hearing) finding their way into the audio channels.

Cellular Network Data Communication. Cellular network voice communications and simple messaging services (SMS text messages) are carried over low frequency (900 MHz) networks while Internet and high speed data access are carried over high frequency networks. The OtoID has a built in 900 MHz cellular network modem (Multitech, MTSMC-C1) that is used to transmit patient test result information from the patient's home to the healthcare institution. De-identified patient test data is encapsulated inside of a text message that is sent to a health care provider's phone. The responsible clinician performs diagnostic interpretation of the test data. This method circumvents the hazards associated with the use of the Internet while providing the broad area coverage required by patient populations. Using a 900 MHz modem enables the OtoID to be used in many rural areas that only have access to low-frequency networks. Rural access to the cellular network is required, lower frequency network infrastructure is usually available. High-speed data networks are usually deployed in more densely populated metropolitan areas and therefore are not available to patients in rural areas.

Figure 11:
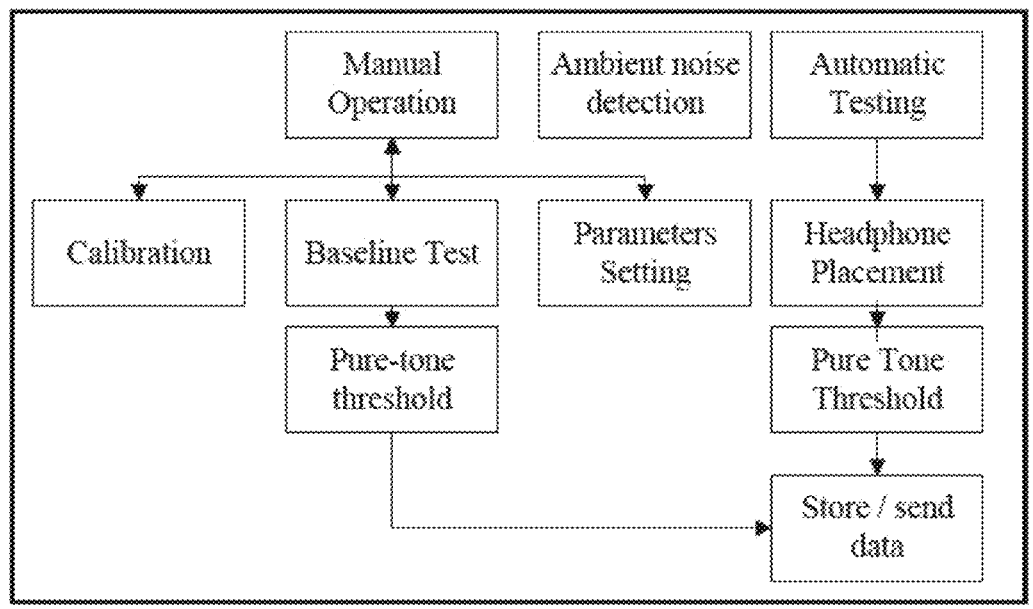
FIG. 11 illustrates a schematic block diagram of an exemplary software program for use with a system for monitoring and/or detecting hearing loss.

Software Design. FIG. 11 illustrates a block diagram schematically illustrating the operation of the software for the OtoID system. In one exemplary embodiment, the software was written in C++ and Nokia's Qt development environment running on top of a Windows CE 5.0 operating system. The software enables either manual or automatic testing of high frequency hearing thresholds. A specific touch sequence on the screen is used to put the device into manual operation as compared with automatic testing mode. The audiologist can perform the operation of entering any patient-specific settings, calibrating the device and performing the baseline (pre-exposure to cisplatin) audiometry. Subsequent testing is automated and completed by the patient at home.

Specifications. In one embodiment, the OtoID can be as set forth below in Table 1.

TABLE 1

| OtoID specifications | |
|---|---|
| Parameter | Value |
| Frequency range [Hz] | 125 to 20,000 |
| Frequency resolution [Hz] | 5 |
| Frequency accuracy [%] | +/−1 |
| Line level audio output [V RMS] | 0.1 to 1.0 |
| Output level [dB SPL] | −15 to 105 |

TABLE 1-continued

OtoID specifications

| Parameter | Value |
|---|---|
| Attenuator range [dB] | 0.0 to −119.9 dB |
| Attenuator resolution [dB] | 0.1 |
| Attenuator accuracy [%] | +/−0.4% |
| Power amplifier output [dB] | 40 |
| Power amplifier resolution [dB] | 0.1 |
| Transducer output impedance [ohm] | 16 |
| Output power maximum [W] | 2 |
| Ambient noise frequency [Hz] | 125 to 14,000 |
| Harmonic distortion + noise [%] | <0.1 |
| Cellular wireless format | 3GSM TS 23.040 Compliant |
| Data storage format | ASCII text files |

In this section, results are presented that demonstrate how the OtoID system meets or exceeds all ANSI/ASA S3.6-2010 calibration standards including frequency accuracy and purity, attenuator accuracy and linearity, rise/fall time accuracy and low harmonic distortion. Additionally, results of 9 subjects tested using the OtoID in the manual as well as automated mode were compared with results obtained using the commercially-available Grason-Stadler Model 61 (GSI-61) clinical audiometer. All manual testing was done by an ASHA-certified Research Audiologist at the NCRAR.

Figure 12:
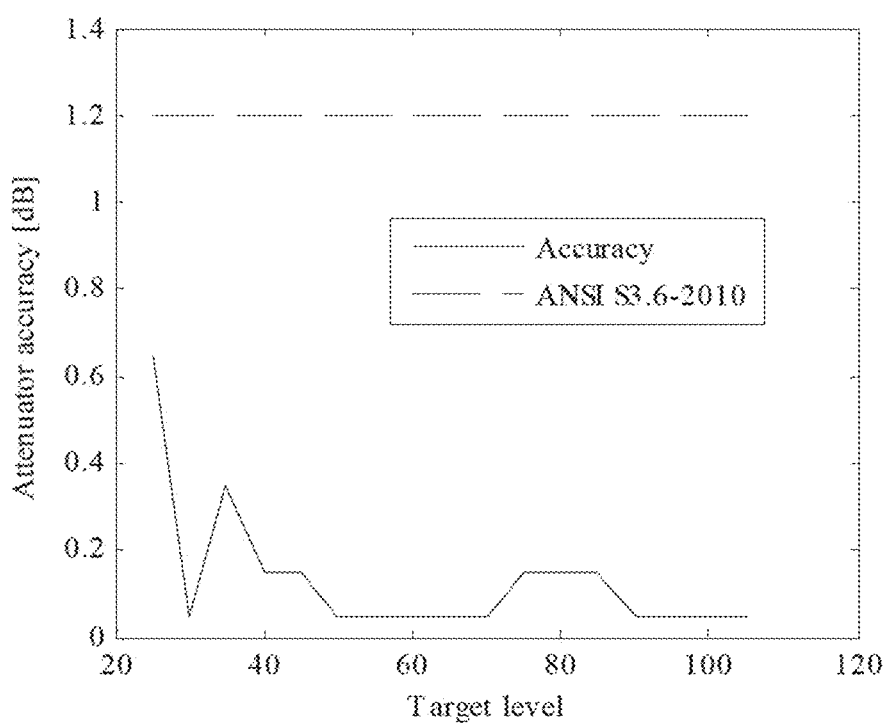
FIG. 12 illustrates a graph of the accuracy of the attenuator across various level settings.

The accuracy of the attenuator is illustrated in FIG. 12. As shown in FIG. 12, the accuracy falls well within the ANSI requirement range of 1.2 dB across all levels tested (25 dB SPL up to 105 dB SPL). For lower target levels, the signal is approaching the noise floor despite calibration in an anechoic chamber, which may cause the measurement accuracy to drop slightly.

Figure 13:
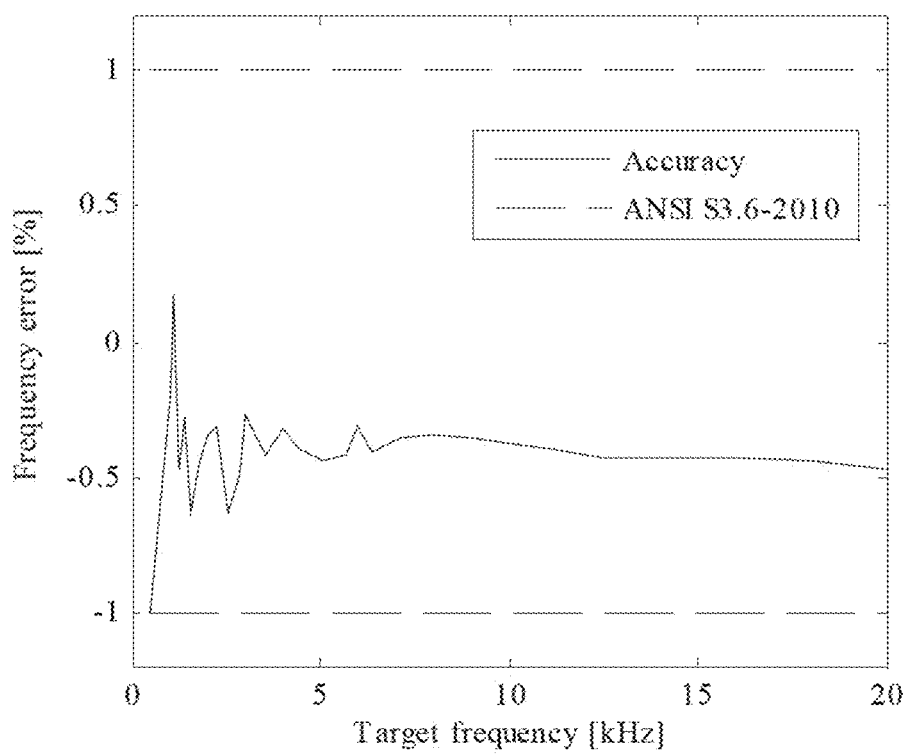
FIG. 13 illustrates the accuracy of the frequency synthesizer.
Figure 14:
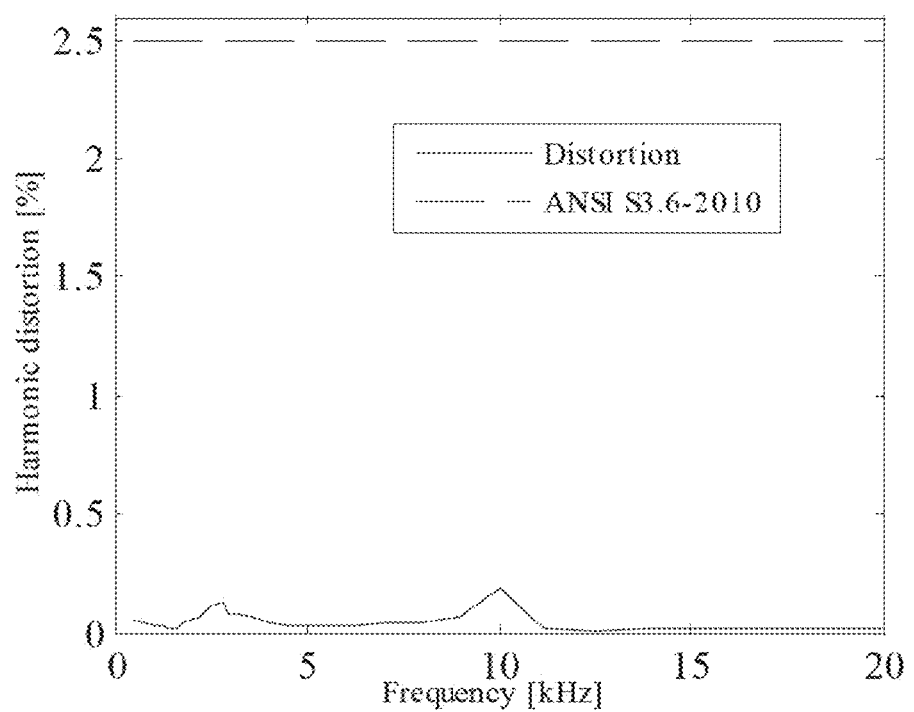
FIG. 14 illustrates harmonic distortion of an exemplary system for monitoring and/or detecting hearing loss across 0.5-20 kHz range.

FIG. 13 illustrates the accuracy of the frequency synthesizer. The ANSI standard permits +/−1% of error in frequency accuracy. The analog pure-tone generator provides excellent accuracy across the entire range of frequencies required for ototoxicity monitoring. Typical total harmonic distortion plus noise performance for the pure tone oscillators in the OtoID audiometer is 0.03% measured at the acoustic coupler. This is well below the ANSI/ASA S3.6-2010 6.1.5 limit of 2.5% shown in FIG. 14.

A total of 9 young (age 18-24, 5 male/4 female), normal-hearing subjects (behavioral threshold less than 25 dB HL across all test frequencies) were included in this study. All subjects met the following criteria: 1) negative history of ear disease; 2) normal otoscopy; and 3) normal tympanometric findings. All subjects were tested in a double walled, sound attenuated booth, with the OtoID system, using both the manual (audiologist tested) and automated (subject tested) software programs. Comparisons in obtained thresholds were made using the Grason-Stadler GSI-61 clinical audiometer. The same research audiologist performed all of the manual testing and also trained and supervised the subjects in the use of the OtoID automated mode of testing.

Figure 15:
FIG. 15 illustrates a test subject evaluating their hearing using an exemplary system for monitoring and/or detecting hearing loss.

Behavioral hearing thresholds were obtained at the following frequencies for each ear: 0.5-8 kHz in half-octave steps (0.5, 1, 2, 3, 4, 6, 8 kHz) and 9-16 kHz in ⅙th octave steps (9, 11.2, 12.5. 14. 16 kHz). The audiologist determined thresholds using the modified Hughson-Westlake technique. The OtoID automated test uses a similar testing algorithm (up in 5 dB steps until the patient indicates a tone is heard, then down in 10 dB steps until the tone is no longer heard. This procedure is repeated until ⅔ responses are made at the lowest hearing intensity level measured.). Unlike the Hughson-Westlake procedure, the starting level in the automated program was 10 dB above the threshold obtained using the manual program. The threshold was determined when the subject heard the tone at least 50% of the time (two out of three responses) at the lowest ascending level. The order of testing with the OtoID Manual, OtoID Automated and GSI-61 were counterbalanced, and a thirty minute break was given between test conditions. All testing was repeated on a second day within one week of the initial test session. FIG. 15 illustrates a subject using the OtoID system to monitor their hearing. The subjects generally reported the OtoID system was easy to use.

Figure 16:
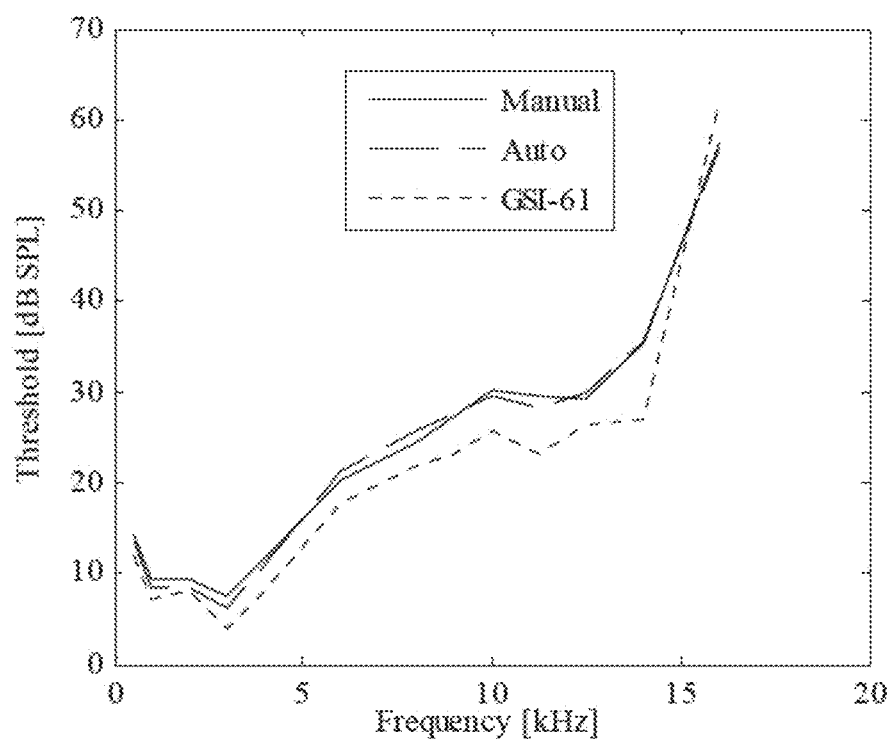
FIG. 16 illustrates normal hearing baseline testing, including a comparison between the current systems and GSI-61

FIG. 16 indicates that the thresholds were comparable between (1) automated mode when the patient evaluated their own threshold, (2) manual mode when the audiologist evaluated the patient's threshold with OtoID, and (3) the audiologist evaluated the patient's threshold using the GSI-61. The difference between the manual threshold and the automated threshold across frequencies was on average 0.3 dB and the maximum deviation was 1.5 dB. The difference between the automated threshold using the OtoID and the GSI-61 was 2.7 dB with a maximum difference of 5.1 dB.

Figure 17:
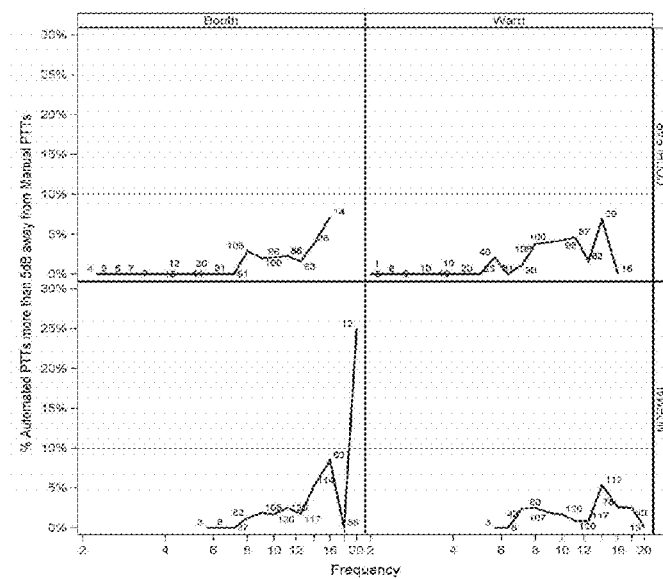
FIG. 17 illustrates OtoID lack of bias when testing on young and older normal and hearing impaired adults on the hospital ward and in the sound booth
Figure 18:
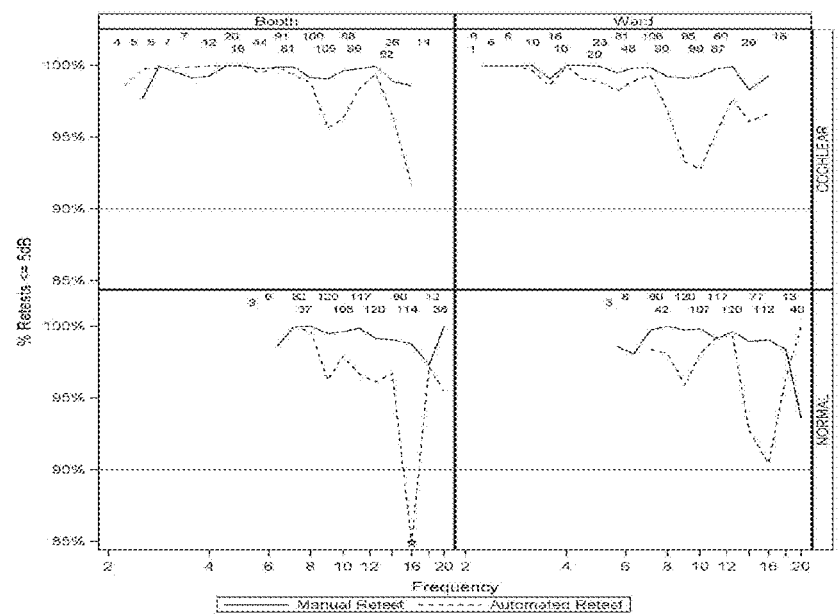
FIG. 18 illustrates OtoID repeatablility when testing on young and older normal and hearing impaired adults on the hospital ward and in the sound booth

The OtoID system is capable of evaluating the hearing of a person across a broad range of frequencies (0.5-20 kHz), sound pressure levels, and specific ⅙ octave step sizes desired to evaluate a patient's SRO during ototoxicity monitoring. The OtoID system is capable of storing baseline measurements and detecting changes from the baseline which may be due to ototoxicity damage. If changes are detected, the system is designed with a cellular modem installed that can notify health care personnel so that the oncology medical team can consider changes in treatment. The level accuracy, linearity, harmonic distortion, and frequency purity of the OtoID system meet the specifications of ANSI/ASA S3.6-2010. Analysis performed on a group of 9 normal-hearing test subjects indicates that the OtoID system thresholds were on average within 2.7 dB of the thresholds measured using a commercial, non-portable audiometer (GSI-61) and that self-testing by a patient is nearly equivalent (within 0.3 dB on average) to testing done by a trained audiologist. Further, when testing young and older adults with and without hearing loss in two environments (hospital ward and sound booth), the OtoID provided self-tested threshold measurements that were unbiased (FIG. 17) relative to testing done by an audiologist. Both the OtoID manual (audiologist test) and automated (self-testing) modes provided repeatable (FIG. 18) thresholds whether they had normal hearing or hearing loss in both environment (Dille et al., in press)

Frequent and regular hearing monitoring has the potential to save the hearing of many cancer patients undergoing treatment with ototoxic drugs if changes in treatment can be made. The OtoID system can be used by patients to monitor their hearing at home, thereby enabling the early detection of hearing damage and improving the quality of these patients' lives post-treatment. In some embodiments, other physiologic measurements can be added to the system, such as otoacoustic emissions whereby distortion product otoacoustic emissions were combined with a cisplatin dose model to predict ototoxicity damage. Instead of using tones to evoke the OAEs, different types of auditory stimuli can be used to evoke the otoacoustic emission including clicks, chirps, or noise. In another embodiment, evoked potentials as measured using electroencephalograms (EEG) or metrics from a psychophysical test could also be integrated with a similar drug dose model to predict ototoxicity damage or damage from other sources such as, noise overexposure or traumatic brain injury especially when this might occur in remote and inaccessible (to medical professional care) areas.

The following examples are provided. These examples are exemplary in nature and not intended to be limiting. In addition, the subjects of these studies included Veterans, however, it should be noted that benefits and applicability of the systems and methods disclosed herein are not limited to Veterans or any other specific class of patients.

EXAMPLE 1

Portable Audiometric Device

As discussed above, the portable hearing testing device described herein, the OtoID, can monitor hearing while a Veteran (or other patient) is undergoing treatment for cancer. Since many Veterans enter treatment with hearing loss, minimizing any additional, treatment-related hearing loss is very important. The OtoID device allows a Veteran to test himself using an automated testing mode or can be tested by an audiologist using a manual testing mode. We tested fifty subjects in a sound booth and on a hospital ward for three days and found that the OtoID provided equivalent results regardless of the test environment or the subject age or hearing ability.

Subjects. Subjects were recruited from the Portland VA Medical Center (PVAMC), the local community, and from a database of research subjects maintained by the National Center for Rehabilitative Auditory Research (NCRAR). All subjects were consented to participate in the study following the guidelines of the PVAMC Institutional Review Board and were compensated for their time. All subjects met the following criteria: (1) no history of ear disease and (2) normal tympanometry and otoscopy at the time of testing. In order to achieve a balance of important patient characteristics, recruitment was based upon three factors: age, hearing status and gender. Age was defined as <40 years or >40 years of age while hearing was divided into normal (≤25 dBHL at 0.5-8 kHz) and hearing impaired (>25 dBHL in at least one frequency). Criteria for excluding potential subjects from this study were: 1) cognitively, physically or psychologically unable to participate; 2) unable to provide reliable behavioral threshold responses (patient did not meet intrasession reliability of ±5 dB using the manual testing mode; and 3) subject or medical record report of Meniere's disease, retrocochlear disorder or active or recent history of middle ear disorder.

Instrumentation. The OtoID device, shown in FIG. 15 during subject self-testing, is comprised of an ARM-based processor with a touch screen monitor running Windows CE and OtoID Firmware, a custom audiometer circuit board with extended high frequency audiometer (HFA) capability, and Sennheiser HDA200 circumaural headphones. The OtoID is ergonomically designed to be sturdy and comfortable to use by both professional and non-professional personnel. In the development of the OtoID, demanding acoustic performance was required such that each ⅙th octave frequency (0.5-20 kHz) has a dynamic range of 115 dB (−10 to 105 dBSPL). The OtoID meets all ANSI S3.6-2010 Class Type 4 and HF audiometer specifications for reference equivalent sound pressure level (RETSPLs), frequency accuracy and purity, attenuator accuracy and linearity, tone switch characteristics, and absence of unwanted acoustic signals. A fully detailed description of the technologies employed in the OtoID device and performance of the device is available elsewhere. Full calibration of the OtoID was done annually with intensity verification checks done weekly at 0.5-20 kHz in ⅙th octave intervals, accomplished using a Bruel and Kjaer (B&K) 2250 sound level, a B&K model 4153 flatplate coupler equipped with a B&K 4192 microphone. The Grason-Stadler Tympstar middle ear analyzer and Maico EasyTymp used in the study were calibrated annually.

Procedures. Procedures for all subjects included (1) a brief hearing history questionnaire; (2) otoscopy; (3) tympanometry; (4) pure tone air conduction thresholds obtained by a licensed audiologist using the modified Hughson-Westlake procedure, and (5) pure tone air conduction thresholds in the SRO frequency range obtained by each subject using the automated self-testing mode. Tympanometry was measured on all subjects using either a Grason-Stadler Tympstar middle ear analyzer or the Maico easyTymp hand-held immittance screening device and results were required to be normal. Tympanometric measurements were considered to be normal when compliance ranged within 0.2-1.8 cm3 and peak pressure ranged within −150-+100 decaPascals (daPa).

All testing occurred on three separate days within one month and was done in a sound attenuated booth and in a quiet area of a hospital treatment unit on each day. All manual mode testing in both ears was done by the same licensed audiologist. Self testing of the seven individualized SRO frequencies using the automated mode was done by the subject. All initial evaluations by the audiologist included behavioral hearing testing (0.5-20 kHz) and subsequent determination of the individualized SRO, defined as the uppermost frequency, R, with a threshold of <100 dBSPL followed by the next adjacent six lower frequencies in ⅙th octave steps, R−1 through R−6, all <100 dBSPL. Initial testing location (hospital treatment unit vs sound suite) was counterbalanced for each subject. The 3-day testing sequence was kept the same including test location and order of testing (e.g., audiologist testing then self-test).

FIG. 15 also provides a view of the OtoID screen during self-testing in the automated test mode. Prior to the subject self-test, the audiologist provided a brief explanation and orientation to the OtoID device and indicated the response required. The subject then began the automated SRO threshold program which utilized the modified Hughson-Westlake threshold procedure. Subjects were first alerted (with "Listen Now" on the screen) to an upcoming listening interval in which a tone may or may not be presented. After the trial, the subject was required to indicate whether a tone was heard (yes/no). If the subject reported hearing the tone when the tone was presented, the level of the tone was decreased by 10 dB. If the subject reported that no tone was heard when a tone was presented, the tone was increased by 5 dB. This continued until a threshold was obtained (two out of three ascending responses at the same dB level) for each of the SRO frequencies. Ten percent of the presentations were randomly presented "catch" trials to detect false positive responses. If the subject reported hearing the tone during a catch trial, the screen message read, "listen carefully for the tone". At this point, a tone may or may not (presentation of another catch trial) be presented. If the subject reported that no tone was heard during a catch trial, the testing continued.

Data Analysis. To determine if the OtoID was accurate for serial self-testing regardless of gender, age, and hearing status, a comparison was necessary between pure tone results obtained from serial automated testing with serial manual testing across testing environments and test frequencies. The assessment was made by contrasting the automated mode OtoID results with the manual mode OtoID results under the variety of conditions. In order to be clinically recommended, automated testing must perform no worse than manual testing by an audiologist, considered for this analysis to be the "gold standard". While frameworks for assessing a new device are varied, in this analysis, three metrics were used to assess the accuracy and reliability of the OtoID automated testing procedure compared with the manual testing procedure: 'Bias', 'Repeatability', and 'False-positive rate'.

Bias: Bias was defined as the percentage of thresholds measured by the subject (automated mode) which was >5 dB different from the thresholds obtained in the same ear and frequency of each subject when tested by the audiologist in the same session and location (booth vs ward). Bias less than 10% indicates that patients evaluating their own thresholds using the automated mode of the OtoID give functionally equivalent thresholds to those obtained by an audiologist under the same conditions.

Repeatability: Repeatability is a measure used to determine if hearing thresholds are functionally equivalent when the threshold test is performed multiple times under identical conditions. To be deemed repeatable, 90% or more tests must achieve retest results within 5 dB for all conditions. Repeatability was derived from an estimate of the variance of the difference between retests and assumed no true change in pure tone thresholds between tests. The variance of the difference between retests was estimated from twice the residual variability of a one-way analysis of variance model, with subject-by-ear as the factor, fit separately to each frequency, location and subject hearing level. The percentage of retests within 5 dB was computed from percentages of the cumulative normal distribution with zero mean and variance defined above.

False Positive Rate: False positives are retests that indicate a clinically significant shift in pure tone thresholds when no true hearing shift should occur. Recall that all subjects are healthy volunteers. A clinically significant shift indicating ototoxicity has been defined by ASHA as 1) a 20 dB or greater increase in threshold at any SRO frequency, 2) a 10 dB or greater increase at any two adjacent SRO frequencies, or 3) loss of response at any three adjacent SRO frequencies where responses were initially obtained.

In this analysis, the set of threshold measurements taken on the first study visit constituted the baseline test, and false positive rates were computed for the second and third follow-up visits. Throughout this analysis, statistical hypothesis tests were avoided for three important reasons. First, multiple threshold measurements obtained from the same subject must be addressed using multiplicity adjustment, such as Bonferroni, resulting in extremely low test power. Second, each subject provided an automated and a manual measurement over seven SRO frequencies of both ears in two locations (booth and ward) on three days of testing, or 84 measurements per subject. This induced a complex correlation structure that must be accurately estimated for any of the p-values to be correct. Finally, all tests must be equivalence-type tests, requiring sufficient evidence to reject the null hypothesis that the manual and automated methods gave different results. Under some limited circumstances, equivalence testing methodology is well developed. However, similar methodology for the instrument testing conducted here is not available. In the end, hypothesis testing was not done in favor of more easily interpretable outcomes.

Results. Forty subjects (80 ears), 19 females and 21 males, ranging in age from 18-74 years with normal hearing or sensorineural hearing loss were recruited for participation. The groups were roughly equivalent across gender. However, younger cochlear subjects and older normal hearing ears were under-represented compared to the other groups, typical for these groups of subjects.

Bias is an indication of measurement similarity between the two testing modes, in this case automated and manual. The four panels represent the type of subject (cochlear, normal hearing) and location of test (booth, hospital ward). The numbers in each panel are the number of tests at each ⅙th octave frequency ranging from 1 to a maximum of 120. Fewer tests were done at frequencies ≤6 kHz as compared to frequencies >6 kHz. This is particularly true for the normal hearing group of subjects since the individualized SRO for this group is primarily in the extended frequency range (above >8 kHz). Only one frequency (20 kHz) exceeded 10% bias. This occurred for the normal hearing subject group when tested in the sound booth. However, apart from this condition, the automated OtoID thresholds did not exhibit bias (better or poorer) compared to the manually-obtained OtoID results and, in fact, results were very similar.

Repeatability was the estimated percent of retests with thresholds that were within 5 dB, the standard definition of a reliable measure in clinical auditory testing. Repeatability was high (>90%) under all test conditions except for subjects with normal thresholds at 16 kHz in the sound suite. When tested using normal hearing subjects in a sound booth, this frequency gives unacceptably low retest accuracy using the automated mode. Note also that the automated test gives lower repeatability throughout the extended frequencies (>8 kHz) though the difference was generally within the standard (±5 dB) across tests and/or subjects.

Hearing shifts that meet or exceed the ASHA hearing change criteria are considered false positives when using subjects not in treatment. It was not uncommon for the SRO frequency range to vary. This situation, uncommon clinically, is one in which the SRO frequencies established at the first visit changed because of retest variability. This may be the result of the definition of "high frequency limit of hearing". This highest frequency showed an inherent fluctuation in our groups. However, in practice, the SRO frequency is established at baseline and does not fluctuate since this is the standard to which all subsequent tests are compared. The measurements in which the SRO did vary were not included in the analysis.

Manual testing yielded uniformly small false-positive rates of 0% under all conditions except for measurements of cochlear subjects tested on the ward (3.8%; 2 tests). The automated false positive rates were somewhat higher for normal subject tested in the booth (3%; 2 tests) and cochlear subject tested in the booth (5.7%; 3 tests) and ward (5.8%; 3 tests). While the automated tests gave slightly higher false positive rates, the actual number of tests was few and within acceptable limits. It should be kept in mind that, in actual practice, when an ASHA-significant shift in hearing occurs regardless of the mode of testing, thorough retesting after repositioning the headphones is done by the audiologist to validate the findings.

The mean age of Veterans across our ototoxicity studies is 62 years. Most Veterans entering treatment have significant histories of noise exposure such that even small decrements in hearing result in large changes in communication ease with family and with the oncology team. Ototoxicity monitoring has the potential to minimize debilitation post-chemotherapy hearing loss if treatment can be changed. Cancer survivability is improving such that quality of life after treatment is emerging as an important treatment goal. An easy to use, sturdy device that allows hearing testing during treatment either professionally or through self-testing is available. In tight budgetary times such as these, husbanding professional resources by using automated testing strategies is an idea whose time has come. After testing, if hearing is found to be stable, no action is necessary. If, however, hearing has shifted, the audiologist can inform the Veteran and the oncology team of the change so that 1) treatment options can be discussed with the patient and 2) auditory assistive devices can be considered.

Additional advantages of the systems and methods disclosed herein include remote data transfer via SMS (simple messaging system) so that testing can be done at home by chemotherapeutic patients. Data transfer capabilities allow the audiologist to monitor hearing thresholds in real-time from a central location, and provide the opportunity for the audiologist to contact the patient for a professional hearing assessment prior to the next treatment if there is evidence of hearing changes. The OtoID device further enables the widespread implementation of ototoxicity monitoring best practices and provides clinicians the critical information and opportunity to minimize or prevent the progression of hearing loss, ultimately preserving a high quality of life for Veterans following treatment.

EXAMPLE 2

Cisplatin Dose-Ototoxicity Model

The following example illustrates systems and methods for (1) establishing pretreatment risk curves that quantify the probability that a new patient will suffer hearing loss within the SRO during treatment with cisplatin and (2) evaluating the accuracy of these predictions in an independent sample of Veterans receiving cisplatin for the treatment of cancer.

Development Study, Sample Subjects. Potential subjects receiving cisplatin were identified daily from the appointment list of the chemotherapy unit at the Portland VA Medical Center (PVAMC) or from an oncology nurse referral. They were prescreened using the electronic medical records for exclusionary criteria and to obtain treatment information. Criteria for excluding potential subjects from this study were (1) subject was cognitively, physically, or psychologically unable to participate; (2) retest thresholds must be within 5 dB at the baseline (pretreatment) evaluation; (3) subject or medical record report of Ménière's disease or retrocochlear disorder; (4) subject or medical record report of active or recent history of middle ear disorder, abnormal otoscopy, or abnormal tympanometric findings; (5) behavioral hearing thresholds were poorer than 70 dB HL #4 kHz. The study subjects were recruited as part of a larger project whose purpose was to compare objective measures (distortion product otoacoustic emission and auditory brainstem response testing) for early detection of ototoxicity. Defining maximum hearing loss was necessary to achieve the goal for that objective measures project.

Subjects were tested in a sound-treated room. All efforts were made to evaluate both ears of each patient at each visit. Hearing shifts are typically bilateral but are not identical in terms of the extent or the timing of the change. Therefore, the hearing result from each ear of a subject at each testing session, designated the subject-ear visit, constituted the unit of analysis to be used throughout.

Development Study, Equipment and Measurements. A Virtual Corporation M320 audiometer was used for collecting all behavioral threshold data including ⅙ octave frequencies. KOSS Pro/43 Plus earphones, modified to improve the signal-to-noise ratio, were used for testing the frequencies 2 to 20 kHz. The earphones were calibrated twice monthly. The calibration procedure, specified by the earphone manufacturer, utilized a platform and silicone rubber coupler to tightly house the Bruel & Kjaer (B&K) 4134 microphone. The Koss earphones were centered and locked onto an aluminum spacer resulting in an effective volume of 6 cm3. The tympanic membranes of each ear used in the analysis were fully visualized. Immittance testing was accomplished using a Grason-Stadler Tympstar middle ear analyzer that was calibrated annually. Tympanograms were considered normal if compliance ranged from 0.2 through 1.8 cm3 and peak pressure ranged within −150 and 1100 daPa. Behavioral pure-tone thresholds were obtained using the modified Hughson-Westlake technique. All testing and calibration was done by an audiologist.

Initial (baseline) testing was done prior to cisplatin administration to establish pretreatment hearing thresholds and to define each individual's SRO, a technique developed and verified previously. Specifically, subjects were tested from 2-8 kHz in ½-octave steps and in ⅙-octave steps in the extended high frequency range (9-20 kHz). The lowest frequency at which a threshold of 100 dB SPL was obtained constituted the top frequency of the SRO. This threshold plus the next six frequencies with thresholds of 100 dB SPL constituting each subject's individualized behavioral SRO were determined and tested. Subsequent testing was done using only SRO frequencies at each treatment interval unless this screen resulted in a hearing shift.

All testing was completed within 24 hr of each chemotherapy treatment, immediately following cessation of treatment, and at 1 mo post-cessation of treatment. There were other sessions in which the SRO thresholds were obtained on a subject but no cisplatin was administered. If a hearing shift was confirmed, testing was expanded to include the entire frequency range of 2-20 kHz to search for other frequencies that might be affected by the cisplatin treatment. Upon confirmation of hearing shift, weekly hearing thresholds were obtained until the behavioral SRO thresholds stabilized. If a hearing shift was confirmed, the oncology team was notified of the shift and provided information about whether speech frequencies were compromised. For the purpose of this study, significant threshold shifts were defined using American Speech-Language-Hearing Association (ASHA) clinical guidelines (American Speech-Language-Hearing Association Ad Hoc Committee on Audiologic Management of Individuals Receiving Ototoxic and/or Vestibulotoxic Drug Therapy, 1994) and included (1) ≥20 dB change at any one test frequency, (2) ≥10 dB change at any two consecutive test frequencies, or (3) loss of response at three consecutive test frequencies. Testing was limited to 105 dB SPL at all frequencies. Using these criteria, a binary indicator for the presence or absence of hearing shift in an ear within the SRO frequencies was obtained. This served as the primary outcome measure used in this study.

Validation Study, Sample Subjects. Patients receiving cisplatin were potential subjects recruited from adult inpatient and outpatient units at the PVAMC. Potential subjects receiving cisplatin were identified daily from the appointment list of the chemotherapy unit or from an oncology nurse referral. Subjects were prescreened using the electronic medical records for exclusionary criteria and to obtain treatment information. The subjects enrolled in the Validation study were part of a larger project to develop and evaluate a portable hearing testing device capable of measuring extended high frequency hearing. Except for the following two study-related differences, the same exclusionary criteria were used to recruit both groups of subjects (those participating in the Developmental or Validation studies). First, there was no exclusion for extent of hearing threshold loss in the Validation study sample. Second, subjects from the Validation study were tested on the chemotherapy unit or at bedside in the case of inpatients. There was no overlap of subjects in these two samples.

Validation Study; Equipment and Measurements. The subjects from the Validation study sample were tested using a handheld ototoxicity identification device. This device, the OtoID, was evaluated in an independent study for its ability to optimize the sensitivity, efficiency, and cost-effectiveness of ototoxicity early identification practices. The OtoID was programmed to deliver up to 105 dB SPL stimuli output levels from 0.50 to 20 kHz. Prior to testing, the tympanic membranes of all subjects were fully visualized. A Grason-Stadler GSI 33 Middle-Ear Analyzer was used to obtain tympanometric measures and was calibrated annually. Tympanograms were considered normal if compliance ranged from 0.2 through 1.8 $cm^3$ and peak pressure ranged within 2150 through 1100 daPa.

Sennheiser HDA 200 earphones were used with the OtoID to reduce the detrimental effects of environmental noise. Prior to each testing session, the OtoID was calibrated using a B&K 4153 artificial ear equipped with the flat plate adaptor. A B&K 2250 sound levelmeter and aB&K4192 microphone were used in the calibration. Testing procedures used with the Validation study subjects were identical to the Developmental study subjects procedures except that subjects in the Validation study were tested across the entire range of 0.5-20 kHz at all sessions, done to achieve the goals of this research project. All testing was conducted by an audiologist. Initial (baseline) testing was done prior to cisplatin administration to establish pretreatment hearing thresholds and to define each individual's SRO. The seven frequencies constituting each subject's individualized behavioral SRO were evaluated at each treatment interval. Subjects were tested within 24 hr of each cisplatin dose (monitor evaluations). Subjects were also evaluated immediately following cessation of treatment and at 1 mo post-cessation of treatment. The criterion for hearing shift (previously described ASHA-defined significant hearing shift) was the same for both studies. If an ASHA-significant hearing shift was noted, repeat testing was conducted across the entire range of frequencies in order to verify the shift.

Data Analysis. Logistic regression was used to develop a statistical model, called the dose-ototoxicity model, relating risk of ASHA-significant hearing shift to treatment factors and patient features using logistic regression. This model would then test the importance of a variety of patient and treatment characteristics on the risk for hearing shift.

Cancer and Treatment Measurements. Subject characteristics were extracted from medical records. These included the subject's age, cancer location, and stage at diagnosis. Lung cancer stages I-IIIa were grouped into early-stage cancer, while stages IIIb-IV were grouped into late-stage cancer. Head and neck, skin, and bladder cancers diagnosed at stage I-III were grouped into early stage, and stages IVa-IVc were grouped into late stage. Treatment factors were also identified from medical records and included whether radiation therapy was administered and the total dose of radiation in gray (Gy), and whether concomitant chemotherapy (doublet) medication, most commonly gemcitabine or etopiside, were given. In addition, the dose, dose given, and cumulative dose of cisplatin administered at each treatment appointment were determined from medical chart review. Dose was the prescribed level of cisplatin (mg/m2) given each subject at each treatment visit. Dose given was the amount of cisplatin received at each treatment (in mg). Cumulative dose was the sum of the doses given (in mg) of cisplatin received up to, but not including, the date that hearing measures were taken on any particular visit. The dose administered on the date of the hearing measurement was not included since the ototoxic effect of cisplatin is not presumed to be immediate. Finally, the measure of the cycles of chemotherapy was defined as the ratio of the number of cisplatin treatments completed up to the hearing measurement date divided by the number of months since the baseline measurement. Admittedly, some treatment factors may seem redundant since, for example, cumulative dose captures both dose given and cycles of chemotherapy.

Developmental Study Analysis. There were repeated measurements in this dataset: between ears at each monitoring appointment and across successive monitoring appointments within each ear. The effect of these sources of correlation was modeled using generalized estimating equations (GEE). With very large sample sizes, it is feasible to build the regression model including all patient factors and treatment effects simultaneously, along with interaction effects, to test the importance of each effect on the fitted risk of hearing shift. However, this approach leads to computational difficulties in the GEE algorithm when sample sizes are as small as are commonly employed in cisplatin ototoxicity research, which appears to average about 40 subjects. To avoid these difficulties, a dose-ototoxicity model was built sequentially to achieve an accurate and parsimonious prediction of hearing shift from our sample of subjects. This model was built in three stages:

1. A "Patient Factor" model was first built and included subject age, cancer location (referenced to lung cancer), and cancer stage (referenced to early stage cancer). Lung cancer was used as the reference location for the model, and early stage cancer was used as the reference category. Pretreatment average pure tone threshold in the SRO was included, along with the upper limit frequency of the SRO obtained at the baseline evaluation. Pretreatment SRO average pure-tone threshold was standardized to a mean of zero and standard deviation using the following equation:

$$(BaseSROAvg-70.2)/12.3$$

BaseSROAvg is the average threshold in the SRO frequencies obtained before chemotherapy on each subject included in the study. The constants are the mean (70.2) and standard deviation (12.3) of the sample baseline SRO. The Patient Factor model was reduced by backward elimination using p-values for the generalized score statistic to find the most important susceptibility factors predicting ototoxic hearing shift.

2. A "Chemotherapy Factor" model was built including cisplatin dose (mg/m2), dose given (mg), and cumulative dose received, along with the important susceptibility factors determined in the model building of stage 1, above. We also included all two-way interactions between the cisplatin dose effects and the important patient factors. Cumulative dose of cisplatin was log transformed and standardized to a mean of 0 and standard deviation of 1 to improve computation. The transformation was log(CumulativeDose) 2 5.70)/0.62. The constants correspond to the sample mean log (dose) of 5.70 and standard deviation of 0.62. The Chemotherapy Factor model was reduced by backward elimination as per stage 1.

3. An "Other Cancer Treatment Factor" model was built on top of the results in stages 1 and 2. This model included presence/absence of prescribed radiation and presence/absence of doublet medication effects as categorical predictors and the dose of radiation prescribed as a continuous covariate. This model was reduced by backward elimination. The model selected at the conclusion of stage 3 constitutes the final dose-ototoxicity model that best predicts ototoxic-induced hearing shift in this sample. The final GEE logistic regression model selected in this analysis provided an estimate of the average risk of hearing shift for each ear at any subject visit, given the covariates included in the final model. Risk curves are computed from the fitted model.

Validation Study Analysis. The risk curves fitted in the Developmental study were used to predict hearing shift at each monitoring appointment on each ear in the Validation sample. Risk scores were compared to the observed hearing shifts at each appointment using receiver operating characteristic (ROC) curve analysis. The ROC is a plot of the true positive rate for predicting a hearing shift against the false positive rate of incorrectly identified nonshifts. The area under the receiver operating characteristic curve (AUC) is a measure of the average true positive rate over the range of false positive rates. High values of AUC indicate an accurate risk model. A 95% confidence interval for the AUC was estimated using a nonparametric standard error estimator for correlated measurements.

Developmental Analysis. One hundred and twenty-three potential subjects were identified from daily checks of the electronic medical records at the PVAMC. Fifty-six of the 123 potential subjects were ineligible according to one or more of the exclusionary criteria. Eleven subjects were ineligible based upon an interview with the subject or pre-interview with the oncology nurse regarding suitability of the subject for recruitment into the study. An additional 20 potential subjects declined to participate. Of the remaining 36, 13 had either baseline hearing that did not meet the inclusionary criterion or did not provide any further visits beyond the baseline visit. The final sample was composed of 23 subjects with one or more follow-up measurements after the baseline visit.

Characteristics of these 23 subjects included in this analysis are shown in FIG. 19. These subjects provided an average of 3.5 (range 5 1-14) hearing assessments. All subjects were male with a mean age of 62.4 yr (range 5 51-79 yr). The majority (n 5 15; 65.2%) presented with head and neck cancers, followed by lung cancer (n 5 6; 26.1%). One subject each presented with skin and bladder cancer. Almost half of the subjects (n 5 10; 43%) were diagnosed with late-stage cancer.

Cisplatin dose ranged from 50 to 100 mg/m2 with a median dose of 100 mg/m2 per treatment. The average initial dose given was 168.7 mg, and average final cumulative dose was 378.8 mg. (Final cumulative dose is the dose as of the last test session on that subject.) Six subjects (26%) were prescribed either gemcitabine or etopiside as concomitant chemotherapy medications. Most subjects were prescribed radiation therapy in conjunction with cisplatin (n 5 18; 78%) with an average radiation total dose (in grays) of 54.9 (range 5 14 to 70) among those prescribed radiation. Forty-five ears (of the 23 subjects) were followed over a total of 155 monitor visits, shown in FIG. 20. From this group, one subject was subsequently removed from the analysis because his baseline thresholds were too variable upon retest. Pretreatment average pure-tone threshold at baseline in the SRO region was 70.2 dB SPL (range 5 43.6-88.6 dB SPL). The highest test frequency in the SRO, which could be taken as a severity measure of each subject's high frequency hearing loss, averaged 11.6 kHz (range 5 5.7-16 kHz). Twenty-two of the 45 ears (49%) experienced a hearing shift during treatment with cisplatin.

Figure 21:
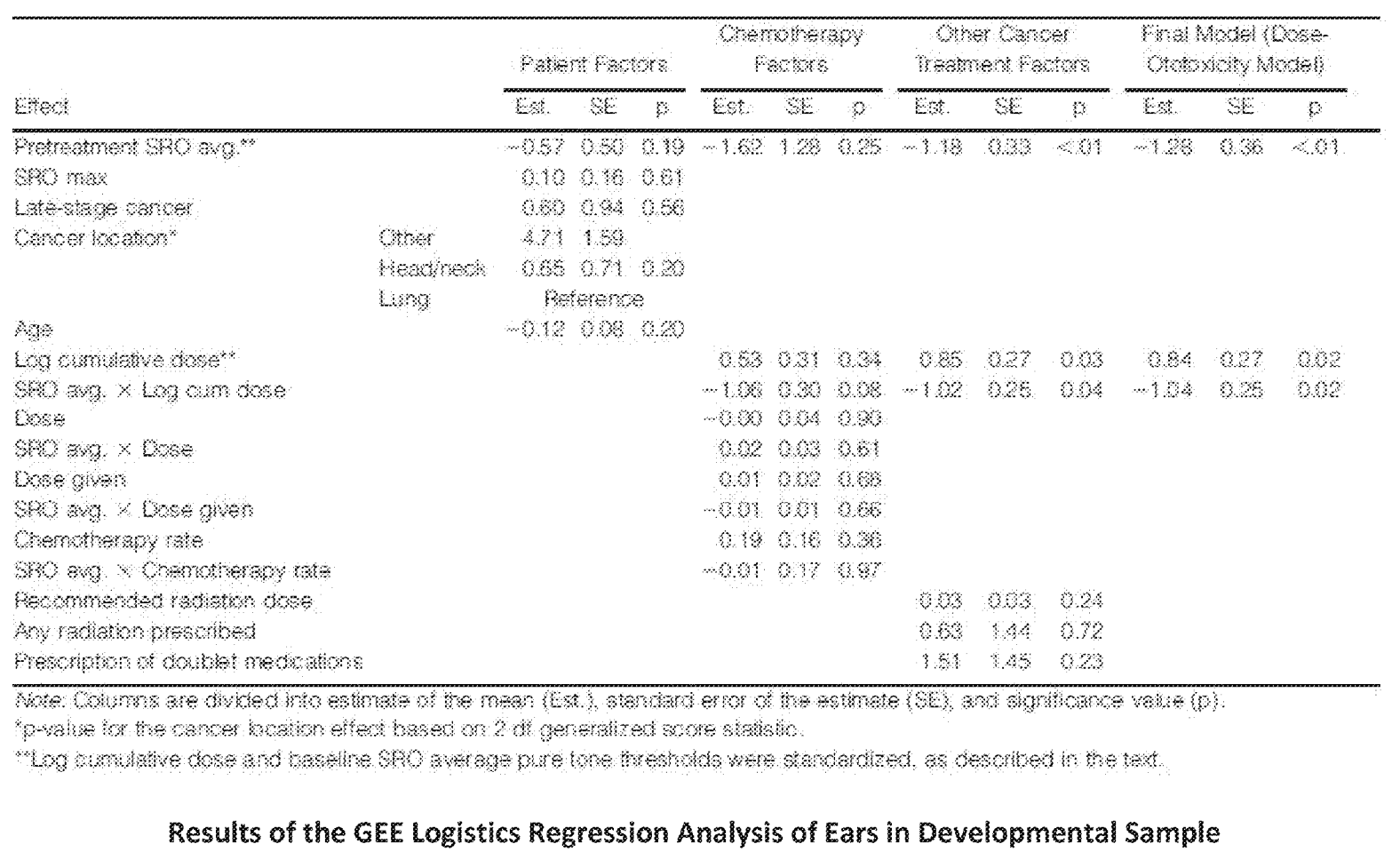

FIG. 21 shows results of the GEE logistic regression analysis. The final model was built sequentially from left to right in the table. The initial Patient Factor model included pretreatment SRO average pure tone threshold, highest frequency in the SRO, presence/absence of a late-stage cancer at diagnosis, location of the cancer, and age. Only pretreatment SRO average remained in the model after backward elimination. No other variables showed important effects on the risk of hearing shift (score statistic 5 2.63, df 5 4, p 5 0.62). The Chemotherapy model included all chemotherapy metrics, along with an interaction between each metric, and pretreatment SRO average retained from the Patient Factor model. Backward elimination indicated that only the standardized log cumulative dose and the interaction between this and pretreatment hearing were the important predictors of hearing shift. The remaining effects had no statistically significant impact on the fit of the model (score statistic 5 4.62, df 5 6, p 5 0.59). Finally, the effects of radiation therapy and doublet medications were tested on top of the Chemotherapy model. No statistically significant effect of radiation (score statistic 5 2.44, df 5 2, p 5 0.29) or doublet medication was detected (score statistic 5 1.45, df 5 1, p 5 0.23) though patients were tested only at treatment intervals and were not followed for long-term effects radiation on the cochlea.

These results indicate that the risk of hearing shift in this sample is best modeled using the standardized log cumulative dose and standardized baseline SRO average pure-tone threshold, and their interaction. The coefficients for these predictors are listed in the Final Model column of FIG. 21. The fitted intercept of the dose-ototoxicity model was 20.24; standard error of the intercept was 0.41. As expected, parameter estimates indicate that increasing cumulative dose of cisplatin induces greater risks of hearing loss. Higher pretreatment pure tone thresholds in the SRO are associated with lower risks of hearing shift. The negative sign on the interaction term indicates a "dampening" effect of poorer hearing on the ototoxic effects of cisplatin.

Figure 22:
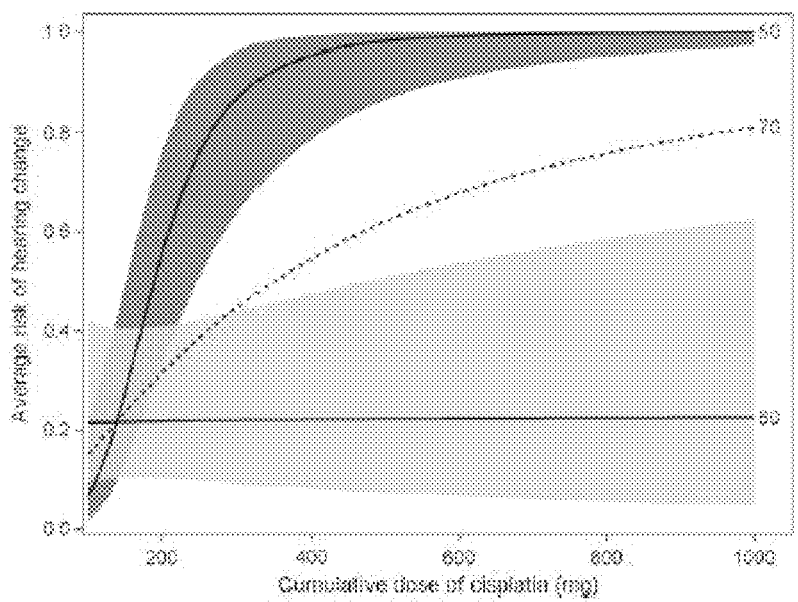
FIG. 22 illustrates a risk curve using a dose-ototoxity model. Risk curves are shown for Developmental sample cisplatin induced hearing shifts in the SRO frequencies. Separate curves are shown for ears with an SRO average hearing of 80 dB SPL (flat line) and 50 dB SPL (solid line) and 70 dB SPL (dotted line), which was the sample mean. The shaded area represents the 95% CI of risk for hearing shift.

Validation Analysis. Twelve subjects in the Validation sample provided 62 monitoring appointments on 24 ears (FIGS. 19 and 20). Subjects in the Validation sample had a mean age of 65.1 yr (range 5 48-80 yr). The majority (n 5 8; 66.7%) presented with head and neck cancers, followed by lung cancer (n 5 3; 25%) and bladder cancer (n 5 1; 8.3%). This group had a considerably lower mean starting cisplatin dose given (mean 5 85 mg vs. 168.7 mg) and had somewhat lower rates of radiation administered (58% vs. 78%). FIG. 20 shows that hearing loss occurred in 9 (38%) ears monitored in the Validation analysis. FIG. 22 shows histograms of the predicted risks in the Validation sample based on the regression results (shown in FIG. 22) and the risk curves (shown in FIG. 21) obtained from the Developmental sample. The factors employed to determine risk were the factors found to be significant from the analysis using the Developmental sample (i.e., cumulative cisplatin dose and baseline hearing thresholds). Hearing testing information obtained at each treatment interval was used only as a means of validating the dose-ototoxicity model when applied to this new, independent sample of subjects.

The top panel of FIG. 22 shows the hearing results obtained from each ear during a monitoring appointment in which there were no ASHA-significant shifts in the SRO frequencies while the bottom panel shows results in which a significant hearing shift occurred. Since subjects were tested multiple times across multiple monitoring appointments, the result from an individual ear might appear in the top panel at one visit and in the bottom panel at another. Among the ears without significant hearing change (n 5 38) during treatment, the risk scores were clustered to the left side of the distribution indicating the model was highly accurate in predicting when no behavioral shift had occurred. Recall that 62% of ears in this sample did not have hearing change during treatment. Among the 38% of ears that experienced hearing shift (n 5 9), the risk scores were more variable though they tended to cluster to the right (higher risk) side of the distribution, as would be expected. Though the Validation study sample was smaller, FIG. 22 shows good separation between histograms. This model is efficient since it determines risk solely on pretreatment hearing information and cisplatin cumulative dose.

Figure 23:
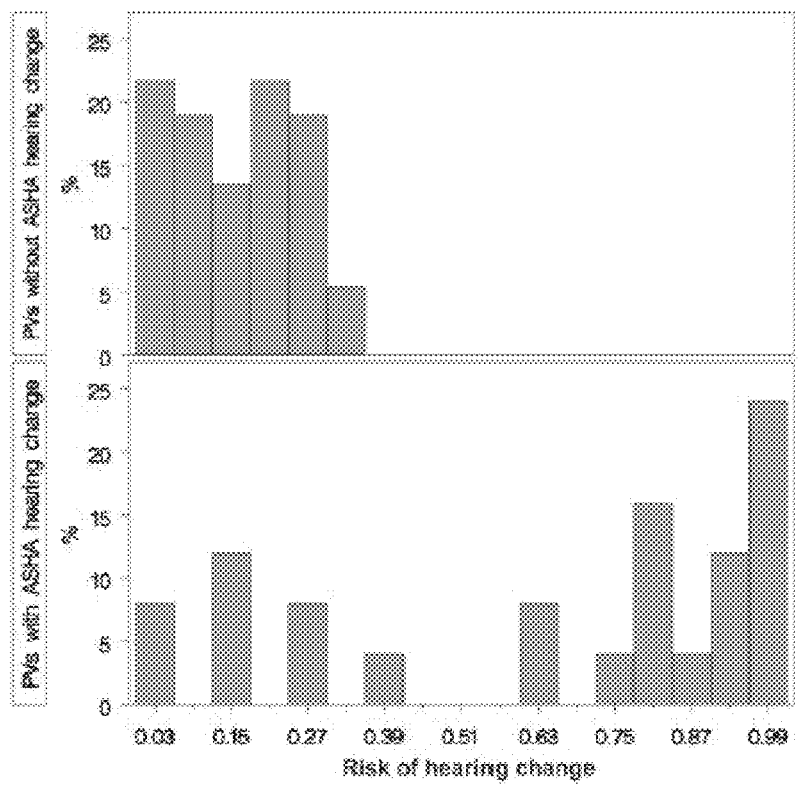
FIG. 23 shows histogram of predicted risk for patient visits associated with an ASHA-significant hearing shift in the SRO frequencies for the Validation sample. The top panel shows risks for monitoring appointments in which the ears did not actually show a shift. The bottom panel shows these risks for ears that had a significant shift. Predictions are based on the doseototoxicity model from a separate Developmental sample.

The ROC curve provides a visual representation of a diagnostic binary classifier. The promising separation of risk scores provided by the ototoxicity model (FIG. 22) should result in a ROC curve that has a high degree of specificity (low false positive rate) and sensitivity (high true positive rate). The ROC curve of FIG. 23 shows the accuracy of the diagnostic model (trained on the Developmental sample) when used to predict hearing shift on the Validation sample. The estimated AUC was 0.85 (95% confidence interval 0.62 to 1.0) indicating an accurate and robust model. More interesting is the high true positive rate (70%) with a concomitantly negligible false positive rate of 0% obtained with this model, improving to 80% at the cost of a low false positive rate of approximately 20%. Further, this elevated false positive rate could be successfully reduced with hearing threshold testing when risk scores for a patient become elevated with successive cisplatin dose.

Predicting which patients will experience ototoxic hearing loss prior to treatment has been a clinical challenge. The systems and method disclosed herein can be used to estimate with better precision who will experience hearing shift and when hearing shift might occur. Pretreatment counseling of those patients and their families as they prepare for and undergo cancer treatment is invaluable. Further, for those found to be at risk of SRO changes within the speech frequencies, the oncology treatment plan could incorporate anticipated dosing adjustment that could stave off the impact that ototoxicity might bring. These prediction models may also improve efficiencies in monitoring programs by providing cost-effective strategies for hearing monitoring. In a time of rising healthcare costs, directing ototoxicity monitoring resources toward those patients most likely to experience hearing shifts near the speech frequencies is cost-effective, but only insofar as the risk of missing a patient who might experience a hearing shift is minimized.

EXAMPLE 3

Ototoxicity Monitoring Using Time Efficient ABR

Accurate, early detection of hearing shifts and subsequent changes in the treatment regimen can help limit ototoxic damage. Objective techniques of auditory nerve and brainstem function such as the auditory brainstem response (ABR) test can be used to achieve ototoxicity monitoring. However, the challenges in using the ABR for monitoring are three-fold. The response must be robust, sensitive to hearing shift, and the procedure must be time efficient.

This example tests the performance of two types of rapidly presented stimulus trains: a Frequency train (holding level relatively constant while varying frequency) and an Intensity train (holding frequency constant while varying level). Additionally, as described herein, cisplatin dose risk assessment model has been developed based on two pieces of information obtained at the pre-treatment assessment: hearing threshold severity and planned cisplatin dose. When used alone or in combination with information about test-retest changes in distortion-product otoacoustic emissions, these two factors can be used to predict with relative precision which patients will experience ototoxic hearing shift and when that shift will likely occur. This example illustrates the accuracy of these ABR trained stimuli when testing Veterans treated with cisplatin for various cancers.

Figure 24:
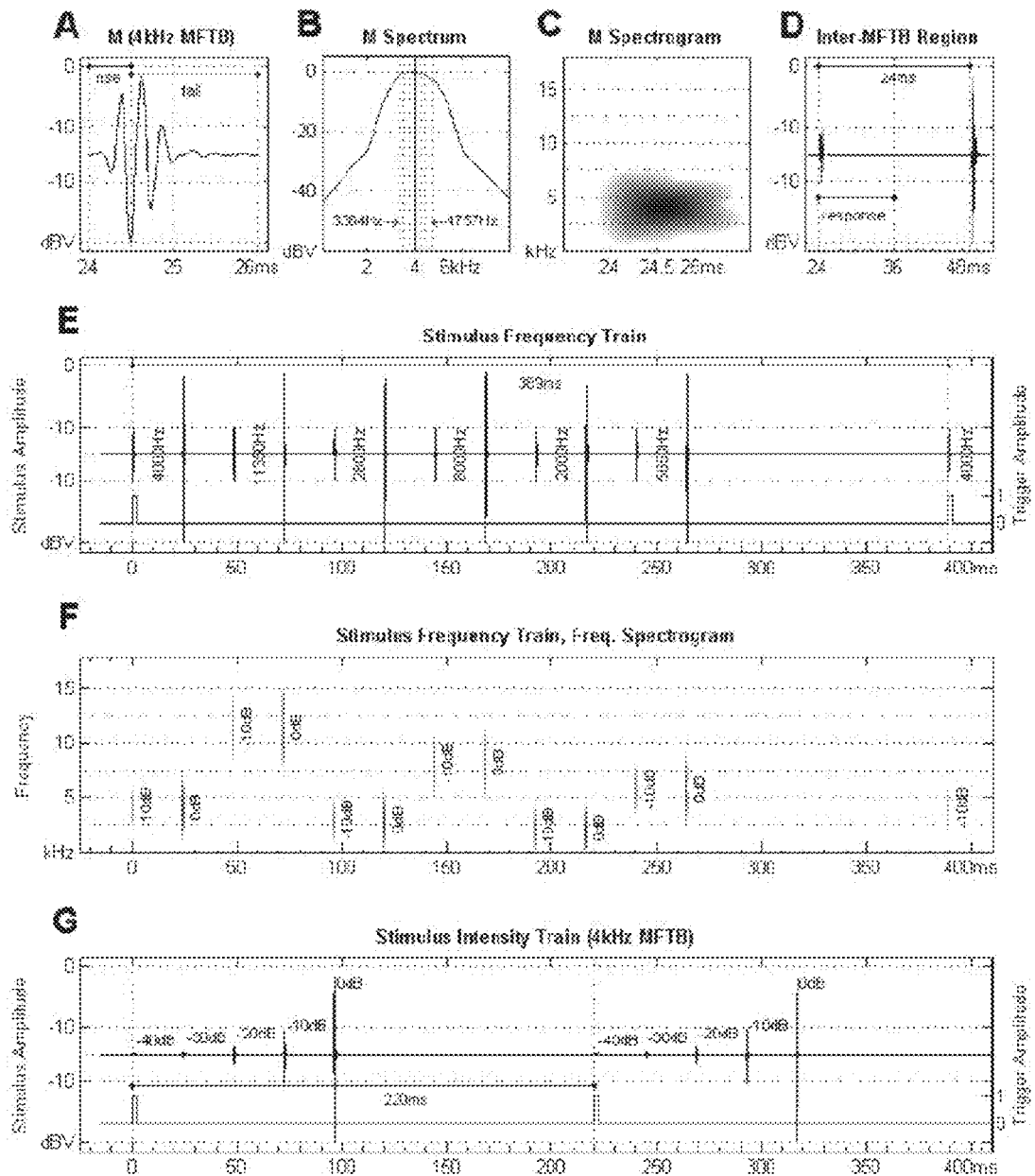
FIG. 24 illustrates specific characteristics of individual Multiple Frequency Tone Bursts.

Methods: Multiple Frequency Tone Burst Stimulus. Six individual multiple frequency tone burst (MFTB) stimuli varying in frequency and level were created for use in the trains. Each of the six MFTB stimuli had an overall bandwidth of ½ octave and was comprised of seven pure-tone frequencies spaced in 1/12 octave steps around the center frequencies of 2, 2.8, 4, 5.6, 8, 11.3 kHz. The digitally created tones were rapidly-gated and phase-shifted to precisely control the peak amplitude of the complex. Specific characteristics of an individual MFTB are shown in FIGS. 24A-D. A time-domain view of the 4 kHz MFTB stimulus, shown in FIG. 24A, has a 2 ms period with 0.5 ms rise and 1.5 ms fall time. This asymmetrical shape with rapid stimulus rise was designed to improve the amplitude of the ABR response while maintaining frequency specificity. Precisely controlling the peak amplitude across frequency relied on the properties of the cosine function to achieve maximum amplitude at onset of the stimulus. Each component of a MFTB was digitally shifted in latency relative to the center frequency so that peak amplitude of the complex could be predicted and then summed to create the composite waveform. Each composite MFTB was then shifted to the presentation starting point relative to other MFTBs and smoothly gated using a Nuttall-type windowing function (FIG. 24B). The frequency spectrogram of the raw MFTB as well as the inter-stimuli interval (24 ms, including response processing time) between individual MFTB when contained in trains of stimuli are shown in FIGS. 24C and 24D, respectively. The polarity of the MFTB could be specifiable as rarefaction or condensation. The real-time waveform of the Frequency train, shown in FIG. 24F, was configured with 6 MFTB stimuli at center frequencies ranging from 2-11.3 kHz in ½ octave steps each presented at two levels (95 and 105 dBpeSPL). The Frequency train played for 288 ms and repeated every 389 ms for a trigger pulse rate of 2.57/sec. A spectrogram for the Frequency train is shown in FIG. 1F which displays the real-time frequency and level distribution of the trained stimuli designed to help prevent auditory adaptation to repeated stimuli.

The real-time waveform of a 4 kHz Intensity train is shown in FIG. 24G. This train consists of five 4 kHz MFTB stimuli stepping in level from 65 to 105 dBpeSPL in 10 dB increments. Separate Intensity trains were created for each of the six center frequencies comprising the Frequency train. An Intensity train took 120 ms to complete and repeated every 220 ms yielding a trigger rate of 4.54/sec.

Instrumentation. All stimuli and stimulus trains were digitally synthesized and controlled using a custom stimulus generation and response acquisition system. The components of the PC-based system consist of a) NI 4551 Dynamic Signal Analyzer (National Instruments, Austin, Tex. USA); b) PA4 Programmable Attenuator, HB6 Headphone Buffer, and DB4 Biological Amplifier (Tucker Davis Technologies, Alachua, Fla. USA); and c) custom designed stimulus generation, EEG acquisition and ABR scoring software. The NI 4551 is an external PC-card with 16 bit resolution, 48 kHz simultaneously sampling, dual channel, ±10V range, precision digital to analog and analog to digital converter. The NI 4551 operates as a signal averaging instrument with one output channel used to generate the electrical stimulus and a second channel to provide a synchronization pulse to the card's analog trigger input which accounts for a 1 ms delay re: stimulus onset of the DB4 processor. The PA4 was used to adjust the overall acoustic stimulus level. Stimuli are presented via the Etymotic ER4B earphone driven by the HB6 amplifier. The DB4 physiologic amplifier system has an internal 1 ms processing delay and the NI 4551 has an internal 33 sample delay, both accounted for in the custom acquisition software application.

The ABR system was acoustically calibrated annually using a B&K 4157 coupler with a B&K 2669 microphone pre-amplifier, B&K 2690 signal conditioning amplifier, and B&K 2231 sound level meter. The broadband noise signal output of a SR780 Dynamic Signal Analyzer (Stanford Research Systems, Sunnyvale, Calif. USA) was fed to the input of the HB6 amplifier reproduced by the ER4 and recorded on the analyzer. Using the peak acoustical amplitude as a reference, the relative amplitude of each of the 42 MFTB component frequencies making up the six different center frequency MFTB stimuli was determined. The amplitude of the reference peak on the analyzer was equivalent to the maximum output amplitude (10V) of the NI 4551, the corresponding relative amplitudes of the pure-tone frequencies at each of the 42 MFTB component frequencies was stored in the stimulus generation program. When operating, the final MFTB stimulus train presentation level was set by establishing a 1 kHz peak reference amplitude on a digital oscilloscope (Model TDS420A, Tektronix, Beaverton, Oreg. USA) using an acoustic calibrator (Model 4230, Bruel & Kjaer). Using peak equivalent SPL (peSPL) calibration methods, the PA4 attenuator was adjusted until the desired acoustical presentation level was obtained. Level verification of the stimuli occurred twice monthly in a 4157 coupler.

Hearing thresholds were acquired for stimuli delivered using the Virtual 320 clinical audiometer (Virtual Corporation) through Koss Pro/4X Plus earphones, modified to improve signal-to-noise ratio for high frequency testing. Full calibration (ANSI S3.6-2010) of the audiometer occurred annually. In addition, intensity verification occurred twice monthly utilized a platform and silicone rubber coupler to tightly house the B&K 4134 microphone.

Subjects. Subjects receiving cisplatin for the treatment of cancer were recruited from the Chemotherapy Unit of the Portland VA Medical Center. A list of patients prescribed chemotherapy was generated daily from the Chemotherapy Unit appointment list and used to identify potential subjects. Subject inclusion criteria were: a) cognitively and physically able to participate, b) the ability to provide reliable (±5 dB) behavioral responses at baseline; c) hearing no worse than 70 dB HL≤4 kHz; d) no active or recent history of middle-ear disorder, Meniere's disease, or retrocochlear disorder; e) normal otoscopic and tympanometric findings and f) the willingness to participate in the study. All subjects were consented to participate in the study following the guidelines of the medical center's Institutional Review Board and were compensated for their time.

Testing. All testing, typically during the hydration portion of treatment, was done in a sound suite at the NCRAR by the same experienced audiologist. The baseline evaluation was performed within 24 hours of the initial chemotherapeutic treatment, typically just prior to infusion. Monitoring sessions were completed within 24 hours of each subsequent treatment and at one month post-cessation of treatment. The total number of patient visits and intervals between visits varied across subjects since treatment regimens depend on cancer type, location and stage, patient health, and other medical factors.

Ototoxic hearing shift was determined by serial pure tone threshold testing. Subjects completed a battery of tests at the baseline session and during each follow-up visits that included otoscopy, tympanometry, conventional (2-8 kHz) and extend frequency (9-20 kHz) audiometry. Bilateral behavioral thresholds were obtained using a modified Hughson-Westlake technique. Following completion of threshold testing, the individualized behavioral sensitive range for ototoxicity, SROBEH, was identified for each ear. The upper bound of the SROBEH was defined as the highest frequency at which a threshold of 100 dBSPL or less could be measured. The next adjacent six lower frequencies with thresholds less than 100 dB SPL, measured in ⅙-octave steps, were then obtained. In order to determine if thresholds were reliable, all testing was repeated at all frequencies after replacing the earphones. Only the SROBEH was tested at each monitoring visit. If hearing change was noted, then full frequency (2-20 kHz) testing was done to search for any additional frequencies with hearing change. Behavioral hearing change was assessed relative to thresholds measured at the baseline visit. The determination of a significant hearing change was based on the American Speech-Language-Hearing (ASHA) clinical guidelines (1994) and included: a) ≥20 dB change at any test frequency; b) ≥10 dB change at any two consecutive test frequencies; or c) loss of response at three consecutive test frequencies where responses were previously obtained. Tympanometry was considered normal if compliance ranged 0.2-1.8 cm3 and peak pressure ranged within −150-+100 daPa.

Out of time considerations, ABR testing was done in one ear only chosen either as the better hearing ear or, in the case of symmetrical hearing, by coin toss. Each subject was seated in a comfortable reclining chair within the sound suite. After preparing the skin, Norotode 20 Ag/AgCl disposable electrodes (Myotronics Inc., Kent, Wash.) were affixed to the skin surface. Electrode impedance of ≤3 kR was the target however, if this impedance was not attainable after three attempts, testing began. Each subject was encouraged to relax and to sleep, if possible. The response was acquired using a two channel recording with the noninverting electrode at Fz, inverting at each mastoid and ground at Fpz. The contralateral recording was used only to verify presence of waveforms, if necessary. Biological signals were bandpass filtered at 30-3000 Hz with the physiological amplifier gain adjusted to the highest gain possible (typically 300,000-400,000) with a rejection rate of 10%. Averaging continued until one thousand artifact-free sweeps were obtained. Each response was replicated at each stimulus frequency and intensity condition.

Rarefaction and condensation standard clicks were used at the baseline session to determine the polarity that resulted in a response that had the clearest waveform morphology and highest amplitude wave V response. This "best" polarity was then used for all subsequent testing. The Frequency train incorporating six MFTB stimuli was used at the baseline session to determine the highest octave (in ½ octave steps) that resulted in a reproducible wave V response, at 105 dBpeSPL and at least one additional lower intensity level, typically 95 dB. The top frequency (F1) was chosen if the response was reliably obtained at both intensity levels across two independent runs. The only exception was in the instance when hearing was very poor. In this instance, if a reliable wave V was obtained at only one level, typically 105 dBpeSPL, at 2.8 kHz and a reliably wave V response was obtained at the lowest available tone burst frequency, 2 kHz, at more than one level, both frequencies were monitored. Intensity trains at both highest half-octave frequencies were then used to collect the ABR at five intensities (65-105) in 10 dB steps. Each Frequency and Intensity train was replicated and summed resulting in grand averages of 2000 ABR runs at each frequency and level. Subsequent (monitoring) testing was done at each treatment interval and included only Intensity trains from the two highest frequencies (F1 and F2) established at baseline.

The same experienced audiologist scored all available response waveforms for latency and amplitude. Other waves (I, III) were also scored, if present. Amplitude was measured from the peak of the response to the following trough in nV. Since the stimulus artifact was present at the highest intensity level, latency was measured from the peak stimulus artifact to the peak response of wave V. At lower intensity levels (<105 dBpeSPL) without stimulus artifact, the wave V was scored relative to the wave V response established at the highest level. Peak wave V latency measured from the peak of the stimulus artifact ranged from 7-10 ms, depending on test frequency. Each subject acted as his own control such that latency and amplitude measures obtained at each treatment interval were compared for change with the measures obtained at baseline. Scorable ABRs were generally limited to the highest two intensities tested (105, 95 dBpeSPL), therefore, most of the analyses presented concern those levels.

Data Analysis. Briefly, a set of discriminant (scoring) functions were derived using logistic regression to model the risk of cisplatin-induced hearing change within the SROBEH. Independent variables were one of several ABR metrics alone each combined with a dose ototoxicity risk assessment model. Receiver operating characteristic (ROC) curve analysis were used to evaluate and compare the test performance of these scoring functions. Details of the data analysis are described below.

A given scoring function was developed, denoted Rij for the ith PV on the jth patient, that best distinguishes patient visits (PVs) with a behavioral hearing change from those without a hearing change. In this analysis, Rij is defined as
(1) $R_{ij} = DO_{ij} W_{DO} + M_{ij} W_M$ $M_{ij}$ is an ABR measurement such as, change in latency, taken on the jth subject during the ith PV, and $W_M$ is the weight assigned to the metric. DOij is the log odds on hearing change of the jth subject at the ith PV conditional on pre-treatment hearing and cumulative dose of cisplatin, and $W_{DH}$ is the weight assigned to that effect.

DO (for "Dose Ototxicity") was defined as DOij=−0.24+ 0.84·Lij−1.28·Bj−1.04·Bj·Lij. Bj is the standardized, pre-treatment SROBEH average pure-tone threshold for the jth subject and L is the standardized log cumulative cisplatin dose in mg. A univariate scoring function has WDO=0 and WM=1 so that identification of hearing change lies solely with the metric M under consideration. This is contrasted with a multivariate scoring function where both the Dose Ototoxicity component and the metric under consideration contribute to the scoring function so that WDH≠0 and WM≠0.

ABRs were collected at each treatment interval using a pair of Intensity trains at the two highest MFTB frequencies tested that generated a robust response at baseline. Candidate metrics were indexed by frequency (F1, F2) and level (95, 105 in dBSPL). Frequency 1 (range 11.3-2 kHz) refers to the Intensity train with the highest relative center frequency; Frequency 2 (range 8-2 kHz) was the train corresponding to the lower relative center frequency. For each frequency by level combination, change in latency (CLat), change in amplitude (CAmp), and loss of ABR response (LoR) were considered. Also considered were summary metrics that involved changes at any stimulus frequency and level combination tested. These were any change in latency greater than 0.3 ms (LatInc) and any loss of ABR response (AnyLoss). The change measures were defined as monitoring value minus baseline value. The change in amplitude measures were multiplied by −1 so that larger values (as opposed to smaller values) on all metrics would be associated with hearing change. Both univariate and multivariate scoring functions were defined for each candidate metric. Throughout the analysis, the weights (W) were established using logistic regression.

Scoring functions were compared using the area under the receiver operating characteristic curve (AUC). The AUC is an estimate of the average true positive rate over the domain of false positive rates. A higher AUC is associated with a more accurate method that correctly identifies hearing change with relatively few false positives. The AUC was estimated using an analog to the Wilcoxon-Mann-Whitney U-statistic. We anticipated that the ABR measurements taken on a subject over the course of ototoxicity monitoring would be correlated. Estimates of the AUC under these circumstances that are based on the U-statistic are correct, but the standard error of the estimated AUC is incorrect, motivating the use of the non-parametric estimator. AUC and standard errors for each candidate metric were estimated using Leave-One-Out Cross Validation, with subjects (as opposed to PVs) constituting the held-out unit.

For a variety of reasons, the ABR measurement was prone to missing data. It was important to describe how these affected the evaluation of ABR methods for ototoxicity monitoring and therefore how missing data can affect clinical utility. A clinically useful ototoxicity monitoring procedure has to be accurate with relatively few inconclusive results. Accuracy, measured using the AUC, was defined above. Inconclusive results occur when measurement attempts fail. Failed measurements decrease the clinical utility of an ototoxicity monitoring method because they yield no relevant information. In the current study, ABR measurement failure rate occurred primarily because of a tester-related problem (e.g., equipment issue) or poor ABR waveform morphology yielding an unscorable response. Further, at times, subjects could not be tested (CNT) due to extenuating circumstances such as chemotherapeutic-related illness. A session resulting in CNT was always a measurement failure because the subject was unable to be tested despite the best efforts of the tester. However, those missed sessions in which no measurement (DNT) was obtained were not counted as a measurement failure because, in theory, the session could have been completed. The final reason for a failed measurement was an absent ABR metric. In this circumstance, ABR metrics could not be extracted for analysis. These instances were scored as "no response" (NR). Whether or not NR is a measurement failure depends on the metric under consideration and the session in which the NR occurred. During baseline visits, NR was always a measurement failure, since it did not permit evaluation of change in latency or amplitude at that frequency by level combination at subsequent monitor visits. During a monitoring visit, NR also failed to provide certain metrics from which to compare the response obtained baseline. However, in this instance, NR was not a measurement failure but rather a true loss of the ABR response. Using this rationale to proceed, measurement failure rates for each metric were computed. The analytic goal was to select the ABR metric that (1) achieved the highest accuracy for correctly identifying hearing as changed or not changed (based on the cross-validated AUC), and (2) provided the most data with the smallest measurement failure rate. To this end, the AUC was plotted against measurement failure rate. The optimal ABR ototoxicity monitoring method was defined as the scoring function with the smallest measurement failure rate that was within one standard error of the AUC obtained from the most accurate metric. This application of the 'one standard error rule' selects the method with smallest risk of inconclusive results and test performance that is statistically similar to the most accurate method.

Figure 25:
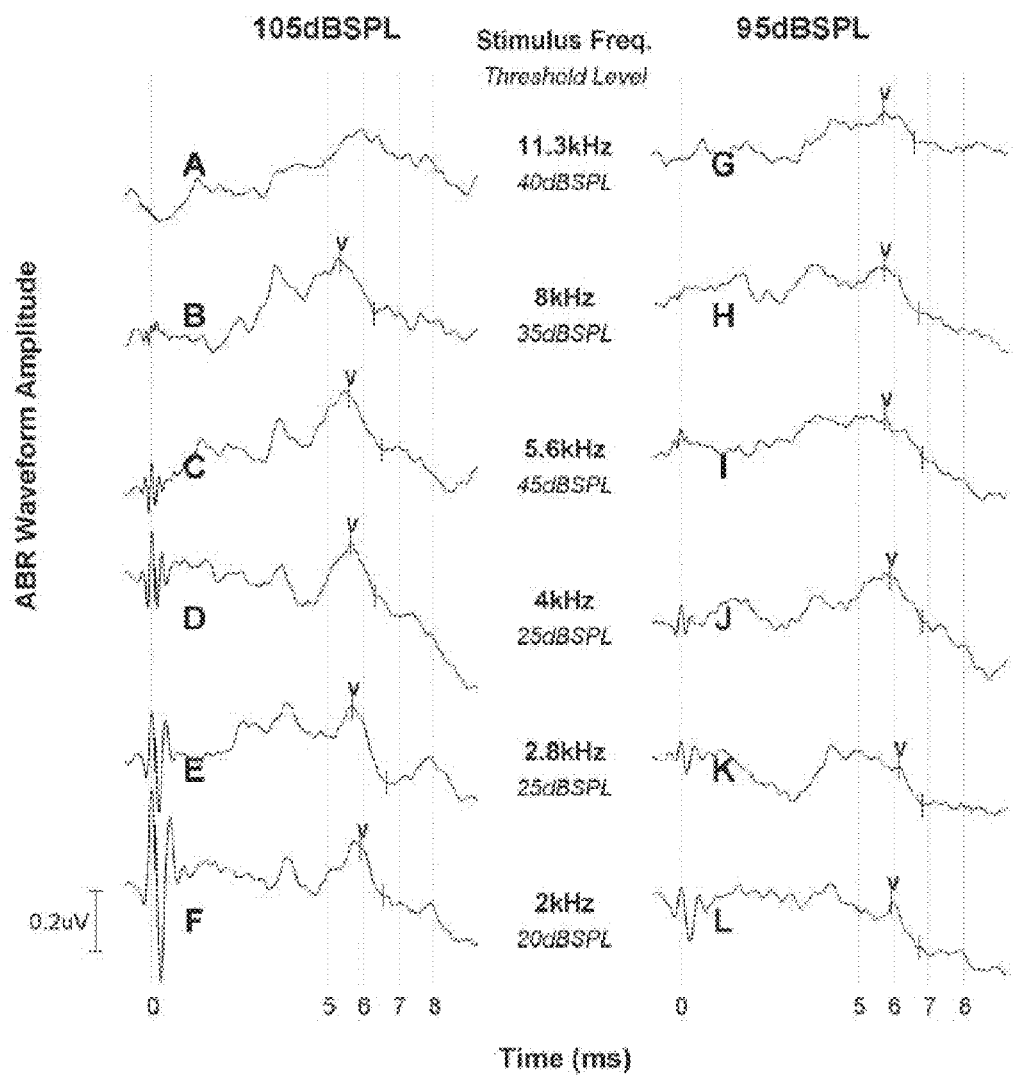
FIG. 25 shows the ABR response obtained from a Frequency train in which MFTB stimuli vary in their center frequency
Figure 26:
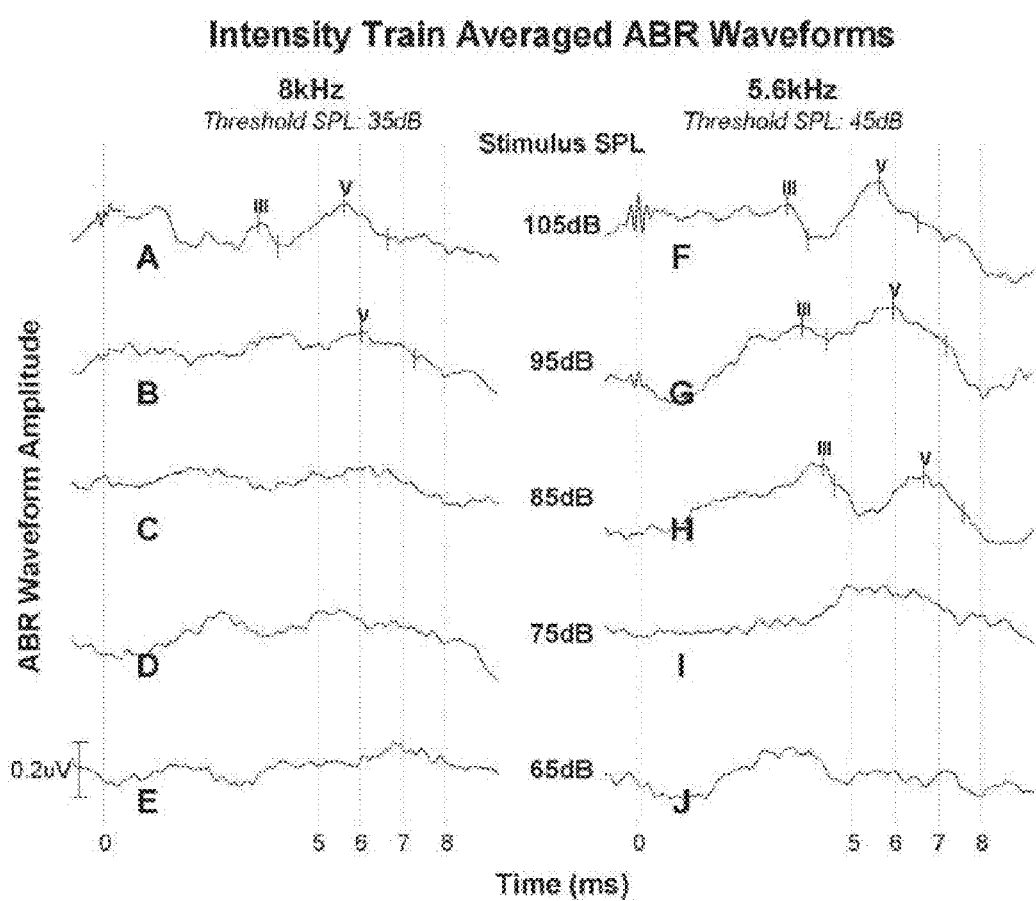
FIG. 26 illustrates intensity train averaged ABR waveforms.

Results. FIG. 29 shows characteristics of the 22 subjects included in this study and the number of visits that were included in the analysis. The subjects provided a total of 71 monitoring appointments during treatment with cisplatin. The average number of monitoring visits was 3.2 (range 1 to 13). Thirty one (43.7%) of these appointments resulted in an ASHA-criterion hearing change. Mean age of subjects was 62.4 years, ranging from 51 to 79 years and all were men. Most subjects had head and neck cancers (n=14; 63.6%) followed by lung cancer (n=6; 27.3%). FIGS. 25 and 26 show a representative example of results obtained from an enrolled subject tested during chemotherapeutic treatment at the baseline (initial) visit. FIG. 25 shows the ABR response obtained from a Frequency train in which MFTB stimuli vary in their center frequency (11.3-2 kHz) and were played at 105 and 95 dBpeSPL. Amplitude (in YV) is shown as a function of time (in ms) with frequency as the parameter. Shown under each frequency is the behavioral hearing threshold (in dBSPL) at same or near the center frequency of the MFTB obtained in the same testing session. For this subject, the top two MFTB frequencies at which an ABR response was reliably obtained at both intensity levels were 8 and 5.6 kHz. Note also the progression of latency increase as center frequency decreases. FIG. 26 shows the ABR results obtained in the same testing session using Intensity trains chosen from the top two frequencies identified from the Frequency train results. For this subject, wave V was reliably obtained at the highest two intensities at using the 8 kHz intensity train while both waves III and V were apparent at the top three levels using 5.6 kHz Intensity train. As can be seen, with each reduction in stimulus level, the response latency migrated out in time as would be expected.

Figure 27:
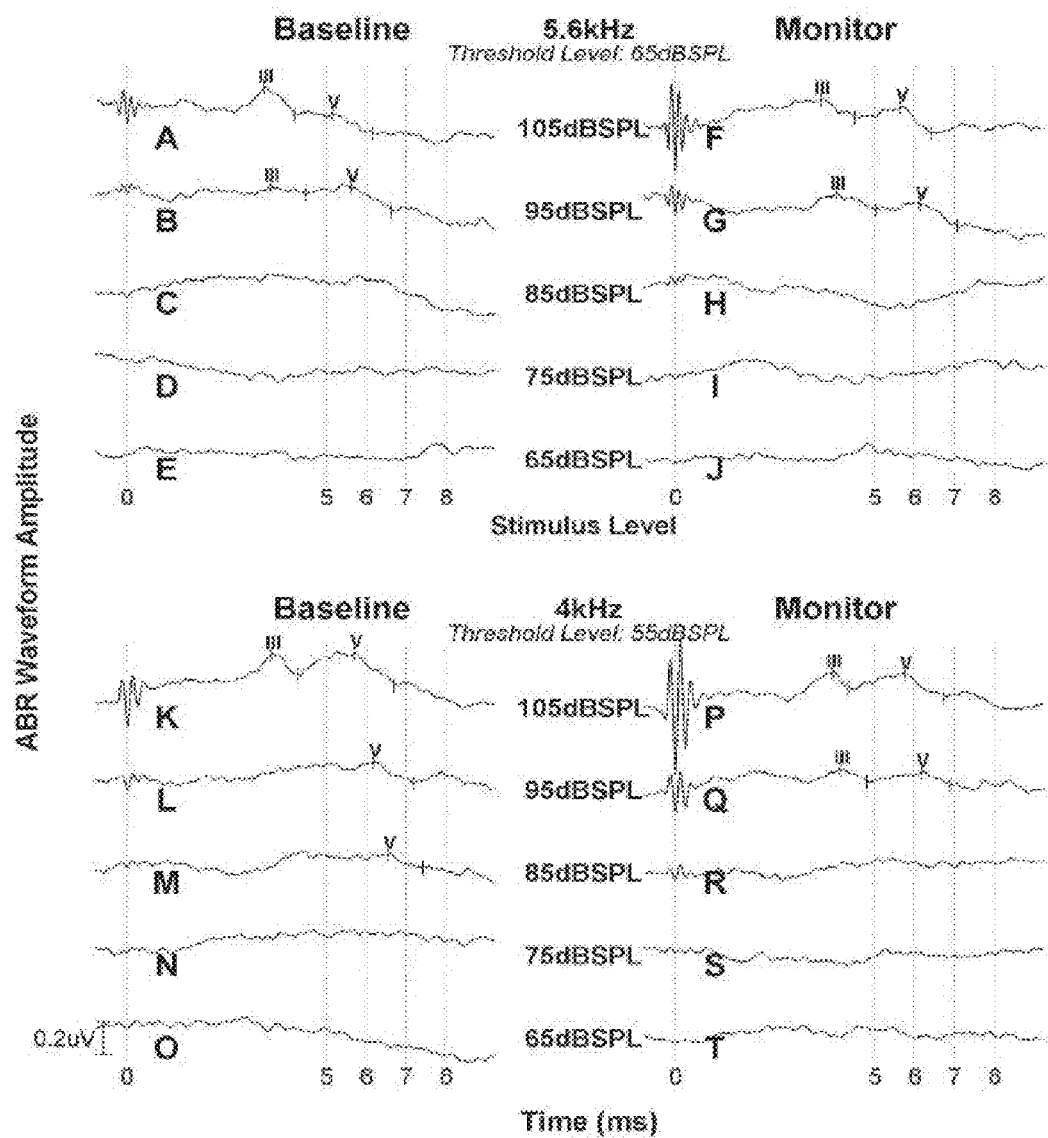
FIG. 27 illustrates intensity train (monitoring) averaged ABR waveforms.

FIG. 27 illustrates change in the ABR response on a subject who experienced ototoxicity during treatment. Using Intensity trains at each treatment interval, the ABR response was compared to the baseline test result for change in latency, amplitude and presence of the response. At the top frequency (5.6 kHz), wave V latency increased by 0.5 ms at both intensity levels compared to the baseline findings. Wave V at 4 kHz during the monitor visit was present with stable latency at 95 and 105 dBpeSPL but was absent to at the next lower stimulus level (85 dBpeSPL). This subject hearing had changed since baseline. An ASHA-significant hearing shift was found in the test ear of +10 dB at 9, 10 and 11.3 kHz at a cumulative cisplatin dose of 190 mg. No further testing was done since cisplatin chemotherapy treatment was suspended. FIG. 30 shows each of the candidate ABR wave V metrics (e.g., 95 change in latency) considered in this analysis, along with mean values for patient visits (PVs) with and without an ASHA-criterion hearing change. Other potential waves (waves I and III) were not present often enough to be included in the analysis. The final column of FIG. 30 shows the measurement failure rate for each test. High failure rates occurred in more than half of the candidate metrics and were exceptionally high at Frequency 1/level=95 dBpeSPL, the highest relative frequency. Further, obtaining a response at the top two frequencies at both levels (105 & 95 dBpeSPL) using a Frequency train did not ensure that the response would also be present using the Intensity train. A test that is inconclusive more than half the time is not clinically useful, so failure rates ≥50% were not considered in remaining analyses.

Figure 28:
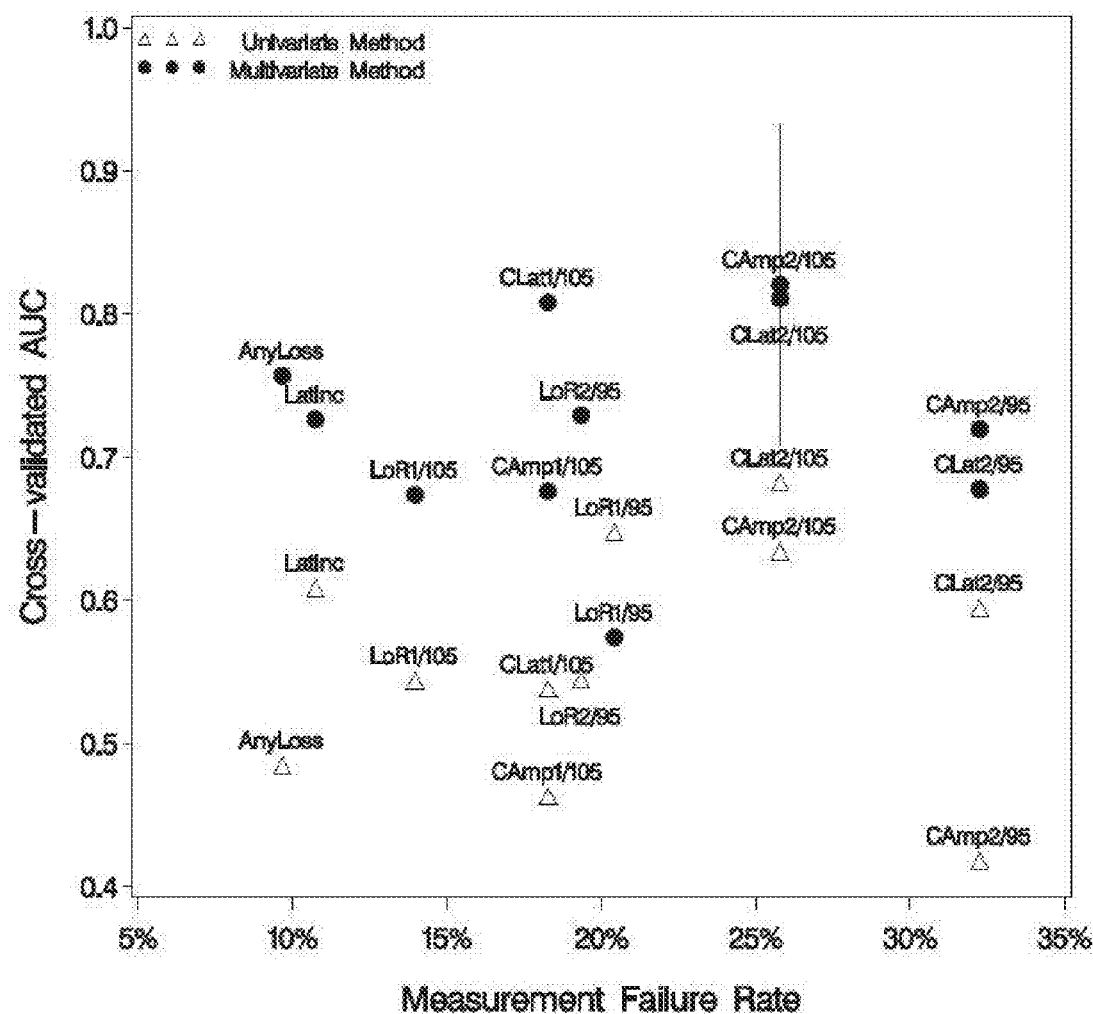
FIG. 28 illustrates measurement failure rates.

A potentially accurate ABR metric shows a high degree of separation between PVs with and without hearing change. FIG. 30 presents the candidate variables for both frequencies and all metrics of those frequencies. Note that the number of metrics increases as the test frequency changes from high (F1) to low (F2). Recall that at the baseline visit, F1 (highest center frequency) was selected only if a response was obtained at two intensity levels, typically 105 and 95 dBpeSPL. FIG. 30 suggests that good candidates may be amplitude CAmp at F1/level=105 dBpeSPL (mean among PVs with hearing change=8.43 nV; mean among PVs without hearing change=1.40 nV) and CAmp at F2/level=105 dBpeSPL (mean with hearing change=57.55 nV; mean without change=10.01 nV). Also, the percentage of PVs with any latency increase greater than 0.3 ms was higher among PVs with hearing change (27%) than those without (3%). FIG. 30 also indicates a large difference in the loss of response metric for F2/level=105. None of the PVs (0.0%) with a hearing change had a loss of response at this stimulus compared to 24% among PVs without an ASHA hearing change. This indicates a backward effect that ears without ASHA-criteria hearing change are more likely to lose ABR response at this stimulus. We believe that this is idiosyncratic since the results were generated by 2 subjects over 2 monitoring appointments where they had no hearing change. Accordingly, this metric is ignored in subsequent analyses. While FIG. 30 hints at the clinical utility of univariate ABR metrics, it does not indicate how multivariate scoring functions might compare. To maximize the clinical utility of an ABR-based ototoxicity monitoring method, the most accurate method that has the smallest measurement failure rate is required. To achieve this objective, the cross-validated AUC is plotted against the sample measurement failure rates in FIG. 28. The scoring function with the lowest measurement failure rate that was within one standard error of the best performing model was selected as the optimal ABR-based scoring function. Filled circles show multivariate scoring function results while open triangles show univariate scoring function results. With the exception the multivariate LoR at F1/level=95 dBpeSPL and univariate CLat at F2/level=105 dBpeSPL, the multivariate methods provide uniformly greater accuracy than the univariate results. The method with the highest overall accuracy was the multivariate scoring function using CAmp at F2/level=105 dBpeSPL (cross-validated AUC=0.82). This method also has a relatively high measurement failure rate of 26%. The AUC±1 standard error is indicated by the vertical bar at the multivariate CAmp at F2/level=105 dBpeSPL point. According to the 'one standard error rule', the most clinically useful scoring function is the one with the smallest measurement failure rate that is within the limits of the standard error bar. Thus, the preferred method is the multivariate scoring function of "AnyLoss" of response, which is statistically similar to the most accurate method but with considerably lower measurement failure rates (10%). This is the optimal ABR ototoxicity monitoring method determined for this sample.

Discussion. Detection of ototoxicity using objective measures such as the ABR is necessary since many patients become incapacitated at some point during treatment and cannot undergo the rigors of a hearing test. Having a test available that can act as a proxy for a hearing test and can be submitted to comfortably is an important tool in an audiologist's armamentarium because ototoxic hearing changes can be considered dose limiting. To be clinically useful, however, ototoxicity monitoring procedures must be robust, sensitive to hearing shift and time efficient. This report examines the test performance of our previously developed trains of stimuli that offer rapid, reliable ABR testing of a range of tone burst frequencies and levels. Unlike prior reports, here we use statistical approaches rooted in clinical decision theory to assess the accuracy with which rapid ABR testing could determine whether or not hearing had changed, taking into account measurement failure rate (the inability to obtain a scorable ABR when testing was attempted, not including loss of response at a treatment visit).

Cisplatin ototoxicity risk assessment models based on pre-treatment hearing thresholds and cumulative cisplatin dose improved prediction accuracy. Multivariate (ABR plus dose ototoxicity model) metrics accurately identified hearing shifts when scorable ABRs could be obtained, with best performing metrics achieving AUC values of over 80%. This rivals the performance of DPOAE testing. The clinical utility of ABR is somewhat more hampered than that of DPOAEs by a relatively high measurement failure rate. Depending on stimulus frequency and level and on the metric selected (amplitude, latency, presence), the ABR measurement failure rate ranged between 10-52%. Only about 10% of ears had to be excluded for a lack of DPOAEs at baseline among Veterans participating in two prospective trials investigating the use of DPOAEs for detecting ototoxic-induced hearing shifts. DPOAEs rarely were "unscorable", perhaps because averaging was variable and continued until the noise floor was low.

Since a test sensitive to early detection should monitor at regions within the cochlea that are likely to change first, ABR testing was done near the high frequency limit of the response. This implies that the ABR may be somewhat elusive at the highest frequency (F1). In fact, we did find that the failure rate at this frequency was much higher than at F2, but only at a lower level (95 dB). At a higher level (105 dB), the metrics were equivalent. Regardless, the measurement failure rate was unacceptably high at almost all levels and frequencies. It is hard to imagine that clinical decisions regarding chemotherapy regimen change could be made using a metric that failed to provide a definitive indication of hearing shift 20% or more of the time. For this reason, the DPOAE method may be preferable to the ABR method. On the other hand, it is possible that other methods for obtaining auditory brainstem measures quickly might perform better than our MTBF trains, such as Auditory Steady State Response (ASSR) for use in obtaining responses at multiple frequencies simultaneously. High modulation rates produce ASSR responses from the brainstem with favorable signal-to-noise ratios obtained more quickly than for analogous measures using tone burst stimuli presented individually.

EXAMPLE 4

Ototoxicity Risk Assessment

Traditionally, early detection is achieved by the monitoring of pure-tone thresholds at each chemotherapy patient visit. However this has drawbacks. The main drawback is that more than one-third of patients who receive ototoxic medications are, at some point in treatment, unable to be tested using behavioral techniques either because of the effects of the disease or the side-effects of treatment. There is a clear need for an objective monitoring strategy for all patients and, in particular, for those who cannot be tested using traditional behavioral means.

Distortion-product otoacoustic emission (DPOAE) testing holds promise as an excellent objective ototoxic monitoring technique. DPOAEs are generated by the cochlear outer hair cells, which are the primary site of damage from ototoxins. The systems and methods described herein relate to a diagnostic method that uses changes in DPOAE levels collected with fine-frequency step sizes to distinguish ears with ototoxic hearing shift from those with stable hearing. A diagnostic method was developed, based on weighted combinations of several DPOAE metrics and a Dose-Hearing model which incorporates pre-treatment hearing and cisplatin dose that best identified ototoxic hearing shift in Veterans taking cisplatin. For comparison, we also evaluated test accuracy for a single DPOAE criterion value, a 6 dB change in DPOAE level, because this value is frequently suggested for DPOAE ototoxicity monitoring applications. DPOAE test performance can be optimized by a multivariate approach and by applying statistical methods to select candidate DPOAE metrics.

Sample. Subjects receiving cisplatin for the treatment of cancer were recruited from the Portland Veteran Affairs Medical Center. A list of patients prescribed cisplatin generated by the Chemotherapy Unit was used to identify potential subjects for the study. Selection was based on: a) cognitively and physically able to participate, b) ability to provide reliable behavioral responses; c) hearing no worse than 70 dB HL at and below 4 kHz; d) no active or recent history of middle-ear disorder, Meniere's disease, or retrocochlear disorder; and e) willingness to participate in the study. All subjects were consented to participate in the study following the guidelines of the medical center's Institutional Review Board and were compensated for their time.

Testing Schedule. Subjects completed a battery of tests at the baseline session and during follow-up visits that included questions regarding tinnitus and vertigo onset or changes, otoscopy, immittance testing, behavioral audiometry, and DPOAE testing. Out of time considerations, DPOAE testing was done in one ear only chosen either as the better hearing ear or, in the case of symmetrical hearing, by coin toss. Baseline testing was performed within 24 h of initial treatment with cisplatin. Subsequent monitoring visits were completed within 24 h of each chemotherapy treatment. The total number of patient visits (PV) and intervals between visits varied across subjects since treatment regimens depend on cancer type, patient health and other medical factors. Additionally, testing was performed at one month after cessation of treatment. Ototoxicity monitoring protocols seek to identify presence or absence of hearing change at each patient visit. Since the VA Medical Center in Portland, Oreg. is regional, often Veterans returned here only on the day of treatment.

Behavioral Audiometry Measurements. The gold standard for hearing change in this study was determined by serial pure tone threshold monitoring. Puretone thresholds were obtained using the modified Hughson-Westlake technique. Baseline (pre-exposure) thresholds were measured from 2-20 kHz using a Virtual Corporation, Model V320 audiometer and modified Koss Pro/4X Plus earphones. The audiometer and earphones were calibrated twice each month.

A behavioral sensitive range for ototoxicity, SROBEH, was identified for each ear from the baseline pure-tone thresholds (2-20 kHz). The upper bound of the SROBEH was defined as the highest frequency at which a threshold could be obtained using a pure-tone signal of 100 dB SPL or less. The pure-tone thresholds of the six lower adjacent frequencies in ⅙-octave steps were then obtained. Thus, seven frequencies constituted the behavioral SROBEH, which was the frequency range tested at all monitoring visits. If a hearing change was noted within the SROBEH, then full frequency (2-20 kHz) testing was done. Behavioral hearing change was assessed relative to the SROBEH measured at baseline. Presence or absence of behavioral hearing change was based on published clinical guidelines (ASHA, 1994) and includes: a) 20 dB change at any one test frequency; b) 10 dB change at any two consecutive test frequencies; or c) loss of response at three consecutive test frequencies where responses were previously obtained.

Using these criteria, a binary indicator for presence or absence of hearing change was constructed for each post-baseline PV in the sample. This binary indictor is the gold standard against which all candidate objective measures are compared. Distortion-product otoacoustic emission measurements. DPOAEs were collected using custom software (Otoacoustic Emission Averager, EMAV; Boys Town National Research Hospital) run on a PC. The software utilized a CardDeluxe digital signal processing board (Digital Audio Laboratories) to generate stimuli and record responses. The primary frequencies (f1 and f2, where f1≤f2) were separately digitized, converted to analog voltages, passed through custom headphone buffers to two earphones (Etymotic Research, ER-2) and delivered to the sealed ear canal. The probe also contained a low-noise microphone (Etymotic Research, ER-10B+) to record responses. The signal was sampled at a rate of 32 kHz, amplified 20 dB by the ER-10B+ pre-amplifier, digitized in 64-ms time windows, and stored in two interleaved buffers, which were averaged in the time domain. The DPOAE level at 2f1-f2 was estimated from a Fast Fourier transform of the grand average of the two response buffers ([A+B]/2). The noise level was estimated at the DPOAE frequency from the A-B spectrum. Measurement-based stopping rules were used, such that at each f2 frequency, averaging stopped when the noise floor was <-26 dB SPL or after 32 s of artifact-free averaging, whichever occurred first. The system was electrically calibrated annually according to the EMAV manual.

DPOAEs as a function of f2 frequency were measured first in seven half-octave steps with f2 ranging from 2-14 kHz using a fixed primary frequency ratio f1/f2=1.22. The levels of the f1 and f2 primaries were L1=L2=65 dB SPL. The two highest half-octave steps (i.e., a one octave range) that elicited DPOAEs at +6 dB signal to noise ratio defined the individualized SRODP. DPOAEs as a function of f2 frequency were then measured across this highest octave in ⅟₄₈-octave steps with f2 ranging over the SRODP and sweeping from high to low frequencies. Thus the SRODP comprised 48 DPOAE measurements. Because measurement-based stopping rules were used, testing time was longer for subjects with greater physiological noise and/or DPOAE monitoring limited to frequencies below about 2 kHz. That is, a low frequency SRODP, imposed by impaired hearing at higher frequencies, increased testing time since biological noise in DPOAE measurements is greater at the lower frequencies. Total test time for octave-range frequencies measured in fine steps ranged from 20-45 min with 45 min being the typical upward limit of tolerable testing for our patients. As a result, due to time constraints, the lower half-octave of the SRODP was not always collected, resulting in missing data. Thus, this report only describes DPOAEs measures derived from the highest half-octave with valid responses.

Both DPOAE and stimulus levels were measured at the plane of the microphone near the entrance to the ear canal. In-the-ear calibration was used to adjust voltage applied to the source transducers in order to set the SPL of f1 and f2 to desired values. Ear canal transfer functions obtained during in-the-ear calibration for baseline recordings were employed as target calibration spectra in order to ensure consistent probe placement across PV and thus improve test-retest reliability. Recorded DPOAE levels were smoothed using a 5-point running average at every PV in order to minimize fine structure level variations.

System distortion was estimated as the DPOAE level at 2f1-f2 measured in a standard 2 cc cavity (Bruel and Kjær 4153 Coupler) for the frequencies and intensity levels used in the present study. For the purpose of assessing system performance, estimates of system distortion were made weekly to ensure that system distortion remained at levels less than -20 dB SPL. In order to determine whether a DPOAE response recorded at a PV was valid, ear canal DPOAE and noise level measurements were compared to the corresponding system distortion averaged across 7 separate coupler measurements.

Specifically, data from the 7 coupler runs were converted to intensity values and means and standard deviations (SD) were calculated from them. For each ear canal measurement, biological noise was converted to intensity, added to the corresponding mean coupler intensity level and the combined noise and distortion value was transformed to dB SPL. The signal to noise ratio was defined as the observed DPOAE level in dB SPL minus the back transformed sum of the subject noise and system distortion in dB SPL.

For a given stimulus condition, a DPOAE ear canal response was considered valid and present if the SNR was at least 6 dB. If the SNR was less than 6 dB and if the subject noise was less than or equal to mean system distortion plus 2 SDs, the DPOAE measure was still considered valid, i.e., the low level emission was considered present, interpretable, and the measurement value was used in the analyses. If the SNR was less than 6 dB and the subject noise was greater than the mean system distortion plus 2 SDs, the DPOAE measure was set to missing, i.e., the measurement was considered uninterruptable and was not used in the analyses.

For the analyses, the highest frequency tested was f=1, followed by f=2 for the next highest ⅟₄₈-octave step, and so forth. Change in DPOAE level was computed as $$\Delta OAE_f = (\text{Baseline DPOAE}_f) - (\text{PV DPOAE}_f)$$

$$f=1, 2, \ldots, 24$$

so that positive values indicate a decrease in DPOAE level at step f and negative values indicate an increase. Cisplatin is expected to cause a positive $\Delta OAE_f$, corresponding to a response decrement.

Data Analysis. The purpose of this analysis is to develop a scoring function, denoted Ri, for the ith PV that best distinguishes PVs with a hearing change from those without a hearing change:

$$R_i = \Sigma_K w_k M_{ik}, k=1,2,\ldots,K.|$$

where Mik is one of K measurements taken on the ith PV, and wk are weights assigned to each metric. A single DPOAE criterion value was initially selected, a 6 dB change at any DPOAE test frequency, and denoted throughout this analysis as the '6 dB method'. Using this notation, the 6 dB method has K=1 metric, such that $$M_{ik} = \begin{cases} 1 & \max(\Delta OAE_f) \geq 6 \text{ dB} \\ 0 & \text{otherwise} \end{cases} \text{ with } w_k = 1.$$

The 6 dB method thus simply assigns a risk score, Ri, of 0 or 1 to each PV based solely on the largest observed $\Delta OAE_f$.

The larger goal was to define Mik more generally, including DPOAE summary metrics as well as patient characteristics and aspects of the cisplatin treatment regimen. There were three stages to this analysis. 1) Identify candidate scoring functions, each distinguished by the metrics included in K, for diagnosing hearing change. Partial least squares regressions were used as well as some relatively simple summary metrics to identify candidate scoring functions in stage 1. 2) Determine the weights, wk, to assign to each metric so that PVs with a hearing change have higher values of Ri than PVs without any hearing change. Logistic regression was used to establish the weights in each candidate scoring function in stage 2. 3) Compare empirically the accuracy of each scoring function against the gold standard of ASHA-significant hearing change. Receiver Operating Characteristic (ROC) curve analysis was used to assess accuracy in stage 3.

Figure 31:
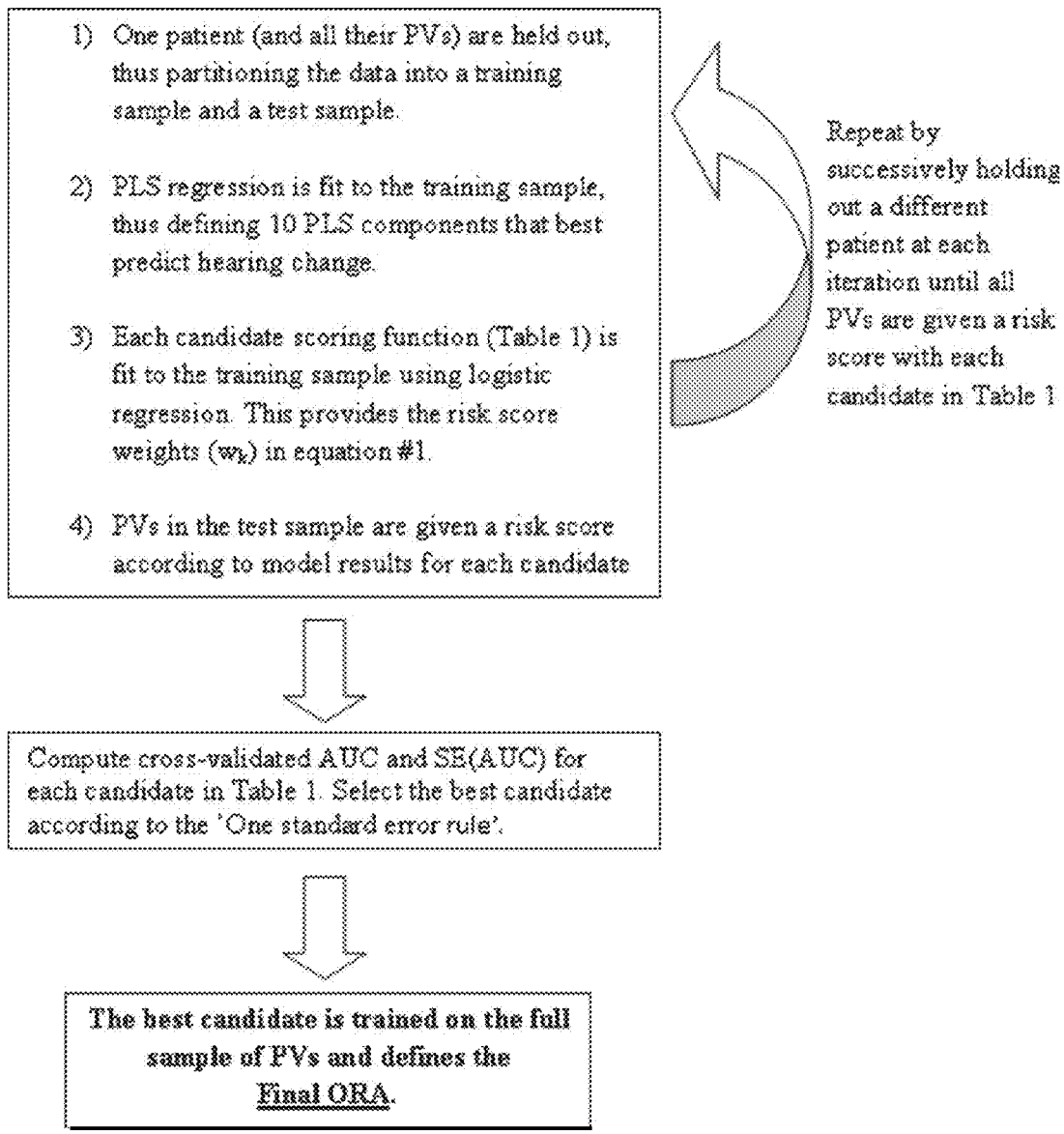
FIG. 31 is a diagram of a Leave One Out Cross-Validation (LOOCV) analysis.

An advantage to this approach is that scoring functions determined a priori (such as the 6 dB method) can be objectively compared against alternative scoring functions. A schematic outline of the approach used here is shown in FIG. 31, and is described in this example.

Identify Candidate Scoring Functions. Patient age, cancer type, cancer stage and location at diagnosis, single dose volume or dose level of cisplatin, concomitant medications, and concurrent radiation therapy do not significantly alter the risks of hearing change in a sample. However, mean thresholds from the pretreatment SROBEH and cumulative cisplatin dose are statistically important variables (p<0.05). More specifically, the Dose-Hearing model is defined for the standardized (mean=0; SD=1), pre-treatment SROBEH average pure-tone threshold in dBHL (Bj) and the standardized log cumulative cisplatin dose in mg (Lij), as the average log (odds) of hearing change for the jth subject at the ith PV:

Log(odds of hearing change$_{ij}$)=−0.24+0.84·$L_{ij}$− 1.28·$B_j$−1.04·$B_j$·$L_{ij}$.

The DPOAE analysis begins with this Dose-Hearing model embedded within it. There were 24 DPOAE level measurements taken during each PV at $\frac{1}{48}$-octave steps in the highest half-octave of the SRODP. Simple summaries of change in OAE level were computed, including mean $\Delta OAEf$, maximum $\Delta OAEf$, and sum $\Delta OAEf$. These, in combination with the Dose-Hearing model, are among the candidate scoring functions to be compared in this analysis (FIG. 32). The 6 dB method was also considered alone and with the Dose-Hearing model.

An alternative approach to simple summary measures is to use partial least-squares (PLS) regression to generate optimal DPOAE summary measures. PLS is suited to situations where there are many measures that are highly correlated such as, DPOAE data. As such PLS constructs new explanatory variables, denoted "components," which are linear combinations of the $\Delta OAEf$ that best predict hearing change. In this approach, each component is defined such that it has maximum covariance with the observed hearing changes (i.e., how much these two variables change together), and is uncorrelated with previous components. The first component accounts for the most variance in the $\Delta OAEf$, the second component for the second most variance, and so on. 10 uncorrelated PLS components were estimated from the sample of PVs.

Next, each uncorrelated component was sequentially added to the base Dose-Hearing model yielding 10 candidate scoring functions for assessment. Thus, the scoring functions that include the 1st component, the 1st and 2nd components, the 1st, 2nd, and 3rd components, and so on, constituted the remaining scoring function candidates under consideration. The set of all 15 scoring function candidates considered (Dose-Hearing model, 1 scoring function with the 6 dB method, 3 scoring functions with simple summary metrics, and 10 scoring functions with PLS components) is provided in FIG. 32.

Determine the Weights of Each Scoring Function. The weights, wk, for each combination of metrics were estimated by logistic regression. Specifically, the log-odds of hearing change at each PV were modeled as a linear function of the metrics listed in Table I. Regression coefficients from the fitted model correspond to the wk, so that Ri in the equation above is equivalent to the estimated log-odds of hearing change at each PV. Separate logistic regression models were fit for each candidate model listed in FIG. 32.

Find the Most Accurate Scoring Function. Each of the scoring functions described in FIG. 32, and their weighting schemes established using logistic regression, were compared using Receiver Operating Characteristic (ROC) curve analysis. The ROC is a plot of the true positive rate against the false positive rate for different cut-offs of the scoring function, and is the basis of most diagnostic test evaluations. The true positive rate and the false positive rate describe the accuracy of a particular candidate scoring function. The true positive rate is the proportion of PVs with a hearing change that are correctly diagnosed using the scoring function, and the false positive rate is the proportion of PVs without a hearing change that the scoring function incorrectly diagnoses with a hearing change. The true positive rate and the false positive rate depend on the cut-off risk score above which a PV would be diagnosed with hearing change. The true positive rate can be arbitrarily increased by lowering the cut-off point, but this comes at the cost of increasing the false positive rate.

The accuracy of each candidate model was succinctly estimated using the area under the ROC curve (AUC). The AUC estimates the average true positive rate over the domain of false positive rates. Higher AUC are associated with overall more accurate diagnostic methods that correctly identify more PVs with hearing change and have comparatively few false positive diagnoses. The AUC was estimated using an analog to the Wilcoxon-Mann-Whitney U-statistic. Since most subjects were observed during several monitoring visits, some degree of correlation was anticipated among the $\Delta OAEf$ across monitoring appointments. Estimates of the AUC under these circumstances that are based on the U-statistic are correct, but the standard error of the estimated AUC is incorrect. Therefore, the non-parametric estimator was used to compute the standard error of AUC and denoted as SE(AUC).

The accuracy of any diagnostic method that is applied to the same sample from which the risk score weights were derived will always be overly optimistic. A scoring function candidate that works well to construct the scoring function on this data set might perform poorly in a separate sample of cisplatin patients. An approach for obtaining nearly unbiased estimates of the diagnostic accuracy is leave-oneout cross-validation (LOOCV). This is a computational algorithm whereby each patient is successively excluded from the training data set, thus partitioning the data into a test sample, which includes the omitted subject's PVs, and a "training" sample composed of all remaining PVs. The risk score weights for all candidate metrics in FIG. 32 are determined from the training sample, and each is then used to predict the excluded patient's risk of hearing change at each PV. The procedure is iterated by leaving out a different patient at each step until all PVs are assigned a risk score according to each candidate in FIG. 32. Nearly unbiased cross-validated ROC curves, AUCs, and SE(AUC) of each candidate in FIG. 32 are then computed from the risk scores. Note that these estimates are 'nearly unbiased' (as opposed to unbiased) because LOOCV is a sample re-use algorithm, which always induces a certain degree of bias.

A test that is rapid is preferable, but only insofar that accuracy is not sacrificed. Therefore, the half-octave analysis was repeated by using only DPOAE frequencies restricted to the highest quarter-octave. Given the same level of accuracy, the quarter-octave model would be preferable to the half octave model since it would take half as long to implement in a real world clinical setting.

More complex models tend to be more accurate than simpler models when evaluated within the sample used to develop the model, but may not generalize to other samples. This is because complex models tend to 'adapt' to the idiosyncrasies of the training data sets, which may not represent other, independent samples. Accordingly, model reduction is necessary to enhance generalizability. Model reduction techniques are commonly used in standard statistical practice, but most are unsuitable for the current analysis. The PLS models are non-nested, so methods based on the likelihood ratio are inappropriate. Metrics often proposed for selecting among non-nested models, such as Akaike's Information Criterion (AIC), are also inappropriate because all of the models listed in FIG. 32 are fit to the same sample and are, therefore, correlated.

Furthermore, these reduction methods are based on the likelihood, which is ill defined in the LOOCV setting. Because the likelihood is conditional on the fitted model, which is different at each LOOCV iteration, the AIC or likelihood ratio statistics are incorrect. In light of the fact that formal ranking and testing methods are unavailable for general problems such as that in the current study, researchers in machine learning advocate model reduction according to the 'One Standard Error Rule'. The best model is the scoring function with the smallest number of metrics (K) that is within one SE(AUC) of the most accurate scoring function. Put another way, the simplest model that is statistically indistinguishable from the best model is preferred.

Also, scoring functions using the quarter-octave fine structure that are within one SE(AUC) of the most accurate scoring function are preferable to scoring functions using half-octave fine structure for reasons noted. Once selected according to these criteria, the best scoring function, hereafter called the "Ototoxicity Risk Assessment" (ORA), was trained on the entire sample, and constitutes the best method among those considered for diagnosing hearing change during a follow-up PV.

Results. Patients were recruited into the study over a 17 month period. One-hundred twenty three patients were identified from pharmacy lists and chart reviews as receiving cisplatin. Fifty-six (45.5%) of these patients met inclusion criteria for the study. Of these, 36 (64%) agreed to participate in the study. Of the 36 patients who agreed to participate, 19 (55.6%) passed the screening physical examination and provided two or more total visits for use in the analysis. Refusals to participate or complete the protocol requirements were primarily due to the time commitment, inconvenience and/or discomfort associated with going to the research laboratory for testing after chemotherapy treatment was administered. This underscores the need for objective and portable measures of hearing.

Figure 34:
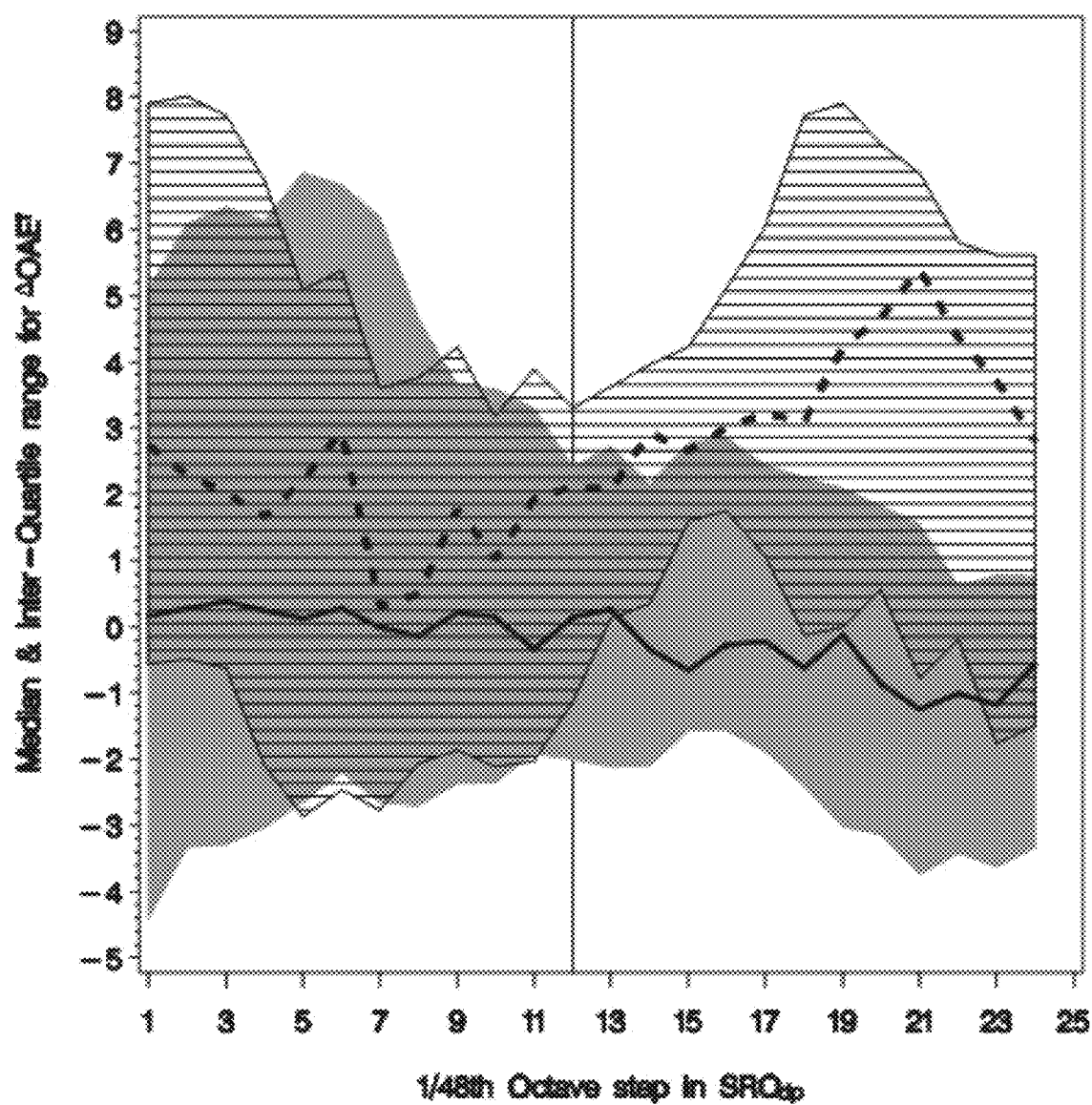
FIG. 34 is a graph of median and inter-quartile range for the indexed $\Delta OAE_f$.

FIG. 33 summarizes the sample used in this analysis. Fifty-six post-baseline PVs from 19 subjects contributed data. The average number of post-baseline PVs per subject was 2.9, ranging from 1 to 12 PVs. Twenty-three of the 56 PVs (41.1%) had an ASHA-significant hearing change. The sample was generally composed of older veterans (mean age 62.6; range 51-79 years). Baseline average pure tone threshold in the SRO frequencies was 69.9 dB SPL and ranged from 43.6 to 86.7 dB SPL. The majority (n=12; 63.2%) of subjects had head and neck cancers, followed by lung (n=5; 26.3%), and one each of bladder and skin cancer. On average, the median starting cisplatin dose level was 100 mg/m2, and ranged from 50 to 100 mg/m2. FIG. 34 shows changes in DPOAE level within the highest half-octave of the SRODP. The dashed line indicates median $\Delta OAE_f$ among PVs with a hearing change. The solid line indicates the same among PVs without an ASHA significant hearing change. The hatched region shows the inter-quartile range of $\Delta OAE_f$ among PVs with a hearing change, and the shaded region shows the same for PVs without a change. An indication of the utility of the DPOAE measurements is given by the degree of non-overlap in the median and inter-quartile ranges between PVs with and without a hearing change. Recall that positive values of $\Delta OAE_f$ indicate a decrease in DPOAE level, while negative values indicate an increase. Several features stand out in FIG. 34. First, median $\Delta OAE_f$ is higher across all f among PVs with a hearing change. This is promising evidence of the utility of DPOAEs for monitoring hearing change among patients treated with cisplatin. Second, the difference in the median $\Delta OAE_f$ appears greater at the highest (left edge of the horizontal axis) and lowest (right edge) steps, and smaller in the middle region. More than anything, this suggests that frequencies should be weighted differently for predicting hearing change, and underscores the potential advantage of PLS over simply averaging the $\Delta OAE_f$ since the latter assumes constant weights. Finally, the inter-quartile range shows the biggest separation at the lowest steps (f=12 to 24), suggesting that a complete halfoctave of testing may be necessary to accurately predict hearing change.

Observations on FIG. 34 provide a better understanding of the differences in the distribution of DPOAE fine structure between PVs with and without a hearing change. However, FIG. 34 does not adjust for the fact that some patients provided many more PVs than other, which might influence the appearance of FIG. 34. This is mitigated using the LOOCV analysis with the candidate scoring functions described in FIG. 22. The LOOCV procedure successively holds out each biologically independent unit (i.e., the subject) while developing the predictive model. Subjects with a relatively large number of PVs cannot influence predicted hearing change on their own PVs, since that subject does not contribute to model fitting during that iteration of the LOOCV procedure.

Figure 35:
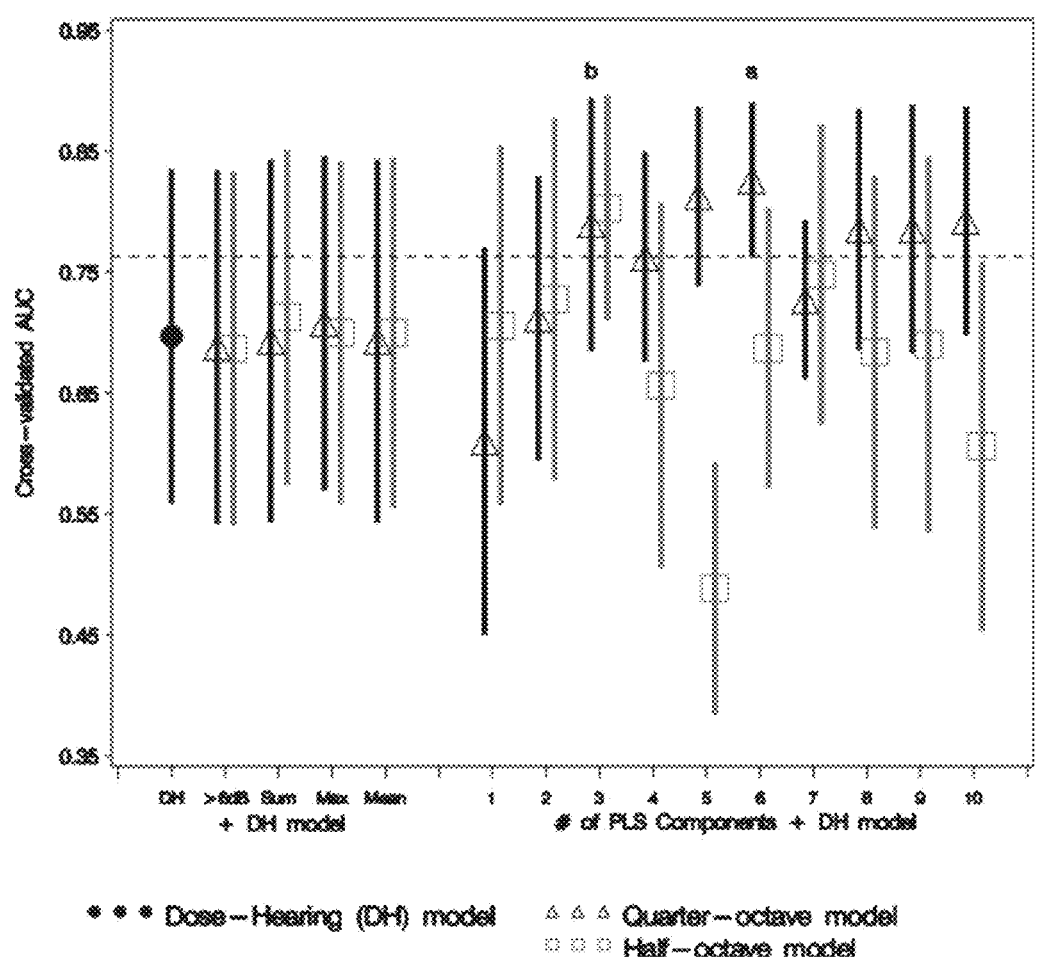
FIG. 35 illustrates cross-validated AUC as a function of each candidate scoring functions.

Results of the LOOCV analysis are shown in FIG. 35. The vertical axis corresponds to the cross-validated AUC and the horizontal axis identifies the candidate scoring functions from FIG. 32. Black triangles show results using the quarter octave fine structure, while gray squares show results for the half-octave fine structure. Vertical bars at each symbol indicate SE(AUC). As a point of reference, the AUC based on the Dose-Hearing model alone, without any DPOAE monitoring, is indicated by the black dot.

FIG. 35 shows that simple summary metrics based on changes in DPOAE fine structure offer little improvement over the Dose-Hearing model alone, which already achieves some success in identifying hearing change (AUC=0.7). However, several of the PLS models using more than two components show considerably higher accuracy than the simple Dose-Hearing model or the simple ΔOAEf summary metrics in conjunction with the Dose-Hearing model. The most accurate model is the six PLS component model, labeled 'a', based on one quarter octave DPOAE fine structure, with a cross-validated AUC of 0.83. However, with six PLS components (and the Dose-Hearing model), this scoring function is more complex than some other candidates that have only slightly lower accuracy. The preferred scoring function is thus selected according to the 'One Standard Error Rule', that is the simplest model with an AUC that is within one standard error of the most accurate model. The dashed, horizontal line marks the AUC minus SE(AUC) of the six PLS component, quarter-octave model. The preferred scoring function is the one with the fewest components that has an AUC above the dashed reference line. According to these criteria, the preferred scoring function is the quarter-octave model using the top 3 PLS components (AUC=0.79) and is labeled 'b' in FIG. 35.

Figures 36, 37:
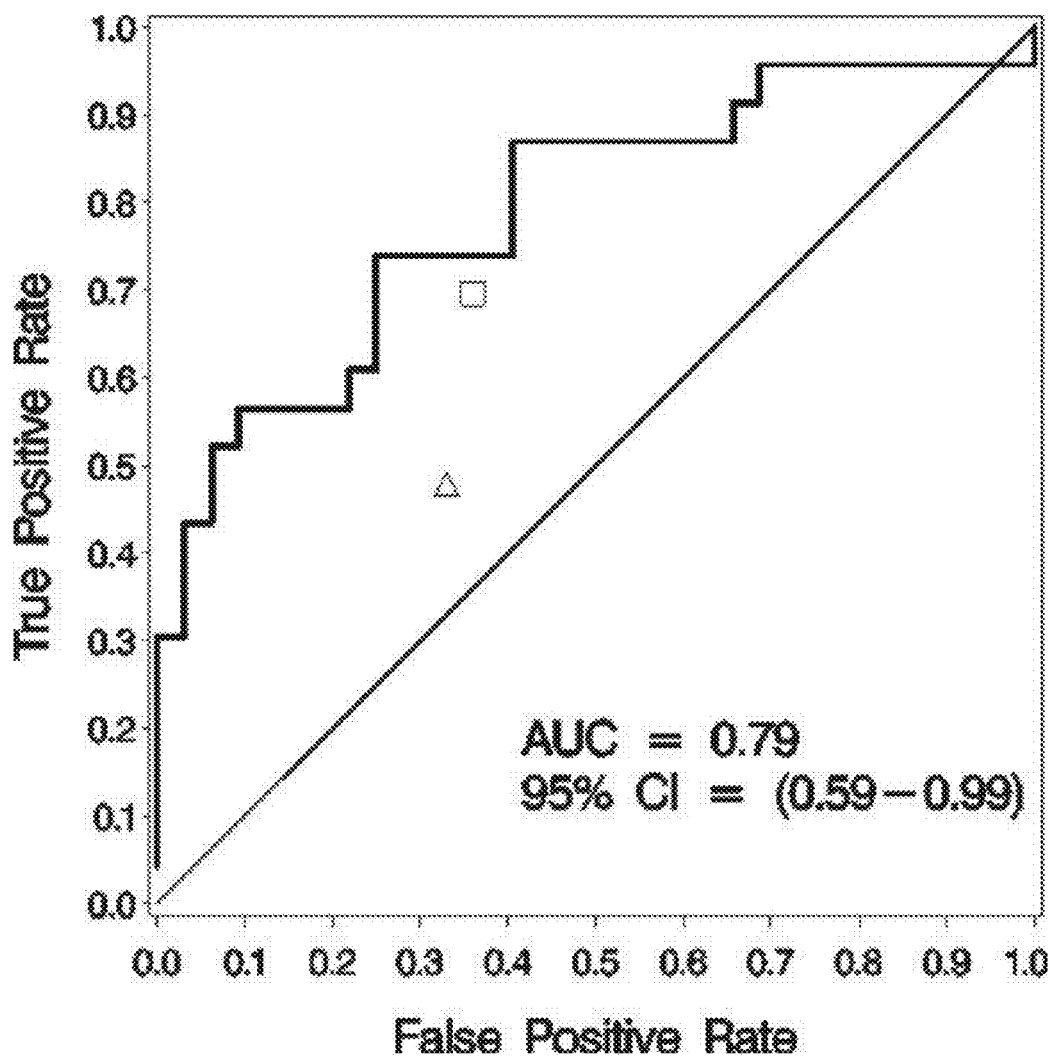
FIG. 36 illustrates a cross-validated ROC curve for the PLS components 1-3+Dosh-Hearing model.
FIG. 37 is a table illustrating final ORA weights based on partial least-squares (PLS) components.

The cross-validated ROC curve for the preferred scoring function is shown in FIG. 36. The estimated AUC is 0.79 (95% confidence interval=0.59-0.99). The ROC curve shows that this is a moderately effective diagnostic method. The true positive rate rises sharply at low false positive rates, but increases more slowly with higher false positive rates. For example, supposing the risk of false positives should be no greater than 10% so that hearing change is not erroneously identified, the method can accurately detect almost 60% of PVs that have a hearing change. FIG. 36 also shows the true positive rate and false positive rate for univariate 6 dB methods utilizing DPOAE data collected in the half-octave (□) (true positive rate=0.69; false positive rate=0.36) and top quarter-octave (Δ) (true positive rate=0.48; false positive rate=0.33) measurement ranges. These are univariate methods that do not include the Dose-Hearing model. The 3 component PLS model is more accurate than either the simple 6 dB method using +6 dB across half-octave or the simple 6 dB method using +6 dB across quarter-octave, since the ROC curve is above each of these points in FIG. 36. In particular, the simple 6 dB methods have unreasonably high false positive rates (0.33 or 0.36) at least as determined using the ASHA criteria for ototoxic hearing change as the gold standard.

The final ORA is trained on the full sample using the Dose-Hearing (DH) model along with the top 3 PLS components, denoted C1, C2, and C3. C1 is a linear combination of the ΔOAEf that has maximal sample covariance with the hearing change indicator. C2 is similarly constructed subject to the constraint that it is uncorrelated with C1. C3 is so constructed subject to the constraint that it is uncorrelated with C1 and C2.

The risk score weights, estimated using logistic regression, are shown in FIG. 37. These weights are combined in the final ORA risk scoring algorithm for the ith PV, such that $$R_i = -0.94 + 0.93 \cdot DH_i + 0.49 \cdot C1_i + 0.82 \cdot C2_i + 0.31 \cdot C3_i.$$

The effects of ΔOAEf on the risk score are captured by the linear combination of PLS components C1, C2, and C3, which are themselves linear combinations of the ΔOAEf.

Figure 38:
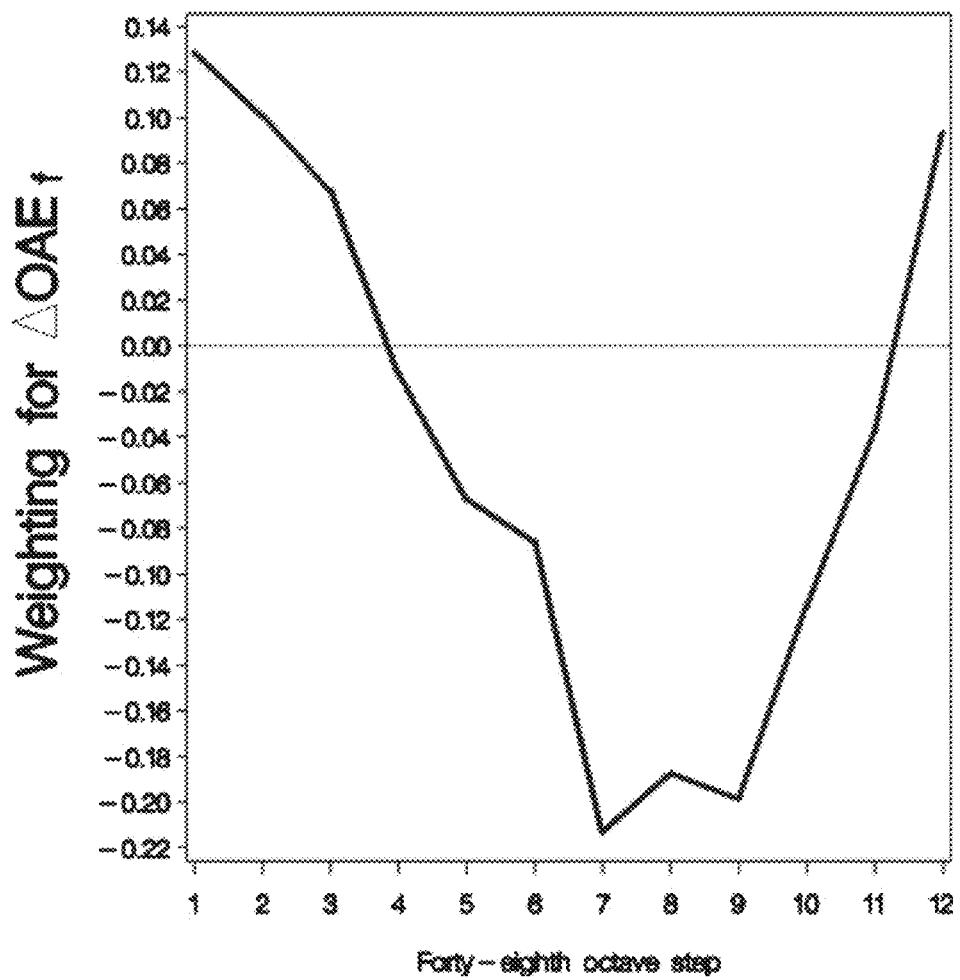
FIG. 38 is a graph of $\Delta OAE_f$ weights used in the ORA as a function of the highest twelve frequencies measured in $\frac{1}{48}^{th}$ octave steps.

Accordingly, the effects of the ΔOAEf on the chances that a hearing change has occurred can be written as a single function of the ΔOAEf. This function is shown graphically in FIG. 38. The DPOAE contribution to the final ORA risk score is equal to the weighted sum of the observed ΔOAEf over quarter-octave at each PV, with weights corresponding to values shown on the vertical axis in FIG. 38. PVs with ΔOAEf profiles that closely match FIG. 38 are ones that have the highest estimated risk of a hearing change. Thus, the highest risk of an ASHA-criteria hearing change occurs in PVs that show large degradations in DPOAEs at the highest frequencies, followed by improvement in the middle frequencies. The $R_i$ are on a log-odds scale, which might not be useful clinically. Instead, the estimated risk, or probability, that a patient has a hearing change at a particular PV can be computed using the inverse logit transformation $$\text{Probability of Hearing Change} = \frac{\exp^{R_i}}{1 + \exp^{R_i}}.$$

Probabilities close to zero indicate little likelihood that the patient has had a hearing change at that monitoring appointment, and values close to one indicates an almost certain ASHA-criteria hearing change.

Figure 39:
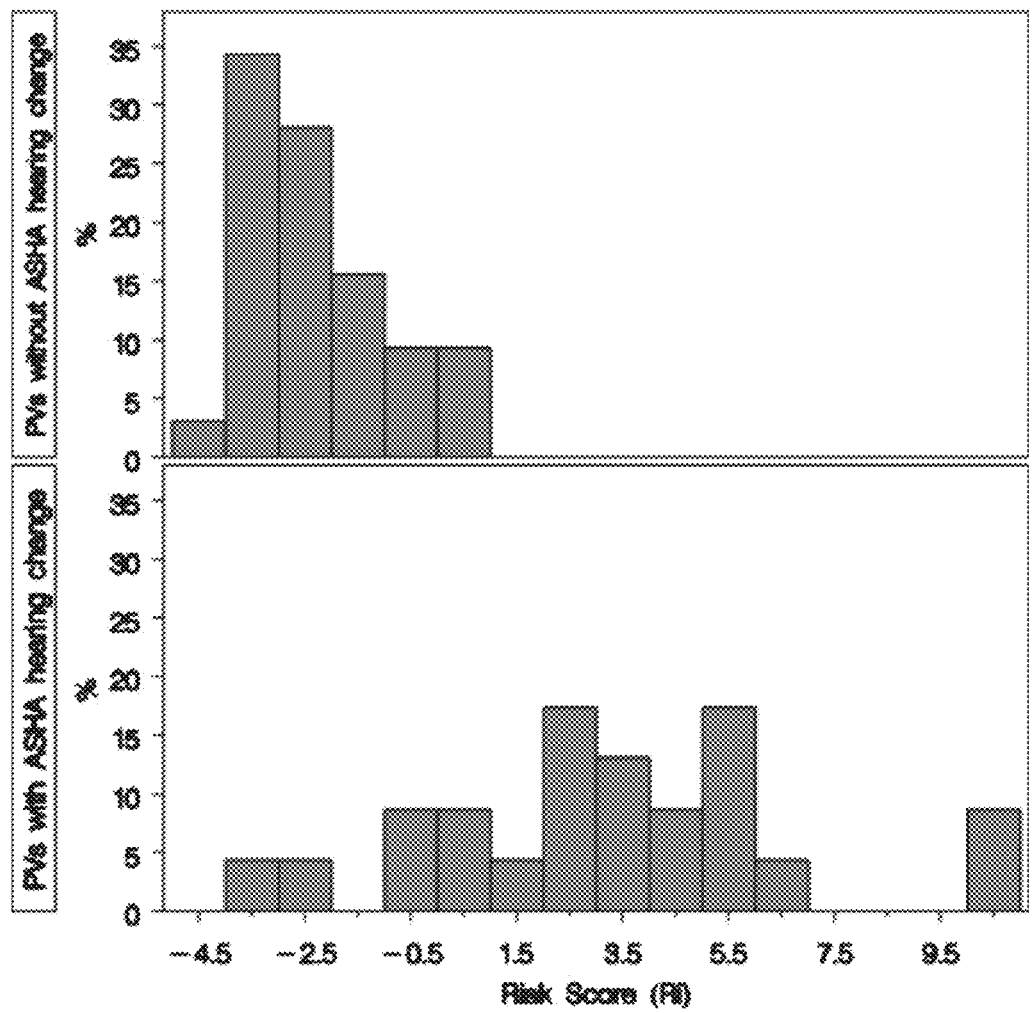
FIG. 39 illustrates histograms of ORA risk scores for PVs in a study sample.

Histograms of the ORA scores for the 56 PVs in our sample are shown in FIG. 39. The top panel shows the scores of PVs that did not have an ASHA-criteria hearing change. The bottom panel shows scores for PVs that did have such a change. As noted earlier, an ideal diagnostic test should give risk scores for the PVs with a hearing change that are higher and well separated from the PVs without a change. This is apparent in FIG. 39. The distribution of scores on the bottom panel is centered to the right of the scores in the top panel, and none of the scores among PVs without a hearing change exceeded 1.5, where the scores on the bottom panel are concentrated.

Discussion. The present results from Veterans receiving cisplatin chemotherapy confirm that cisplatin exposure reduces or eliminates DPOAEs. Results also show an association between changes in DPOAE levels and the presence of a clinically significant hearing change as defined by ASHA (1994). However, significant improvement in the accuracy of DPOAEs for predicting hearing change was shown to be associated with the use of weighted combinations of DPOAE metrics and two risk factors for ototoxicity, behavioral hearing thresholds prior to treatment and cumulative cisplatin dose, from a Dose-Hearing model. A multivariate approach combining these three sources of information, appropriately weighted and using DPOAE level changes evaluated over a quarter-octave range near each subjects' high frequency DPOAE limit, yielded a reasonably accurate (AUC=0.79) and rapid assessment of ototoxicity risk. Accordingly, such an ORA is useful as part of a test battery for all patients receiving cisplatin, but particularly for those unable to take a behavioral hearing test. Although the current example considered only changes in hearing and DPOAEs between each monitoring visit and the pre-exposure baseline test, the approach was designed to both identify and monitor progression of ototoxicity in a clinical setting. This can be achieved by establishing a new baseline following each significant hearing change that is confirmed on a repeat test. By shifting the baseline, DPOAEs can be used to monitor the progression of ototoxic hearing loss until they are no longer recordable.

This example used 1/48th octave step sizes. The rationale for using fine measurements and employing a smoothing algorithm was to reduce the test variability of the DPOAE measurements. Such methods can minimize effects of dips in the DPOAE fine structure, as well as any spurious measurements, that could confound estimates of DPOAE change. Our data (e.g., FIG. 38) support that important information about weighting frequencies differently would not have been obtained using large step sizes. However, in some embodiments, it may be that larger spacing between test frequencies would be preferable to decrease test time. Other ways to improve clinical performance of this method can include collecting other distortion product emissions which require no additional test time and which can improve test performance.

The shape of the weighting function (FIG. 38) provides an indication of the way in which cisplatin altered DPOAEs in subjects with ASHA-significant hearing shifts. Thus, the highest DPOAEs able to be monitored in each subject were those that showed the greatest cisplatin-induced level decrements. While there was some inconsistency in the pattern of the observed DPOAE changes, an enhancement, or increase in the DPOAE level was often seen at the adjacent lower frequencies.

One potential impediment to the use of DPOAEs to monitor hearing in adult cancer patients is that the objective and behavioral measures monitored for changes may not overlap. DPOAEs monitored were often at frequencies below those that showed behavioral change. Overlapping frequency regions can contribute to better performance for both univariate and multivariate solutions. Nevertheless, the ORA accuracy observed within our sample population of pre-exposed hearing impaired Veterans was still remarkably high.

Based on patient characteristics, treatment progress, and DPOAE results, the device disclosed herein can provide clinicians with estimates of the risk that hearing changes have occurred, along with a 95% confidence interval for that risk. A pass/fail result for each PV is also available once a suitable false positive rate is chosen from the validation sample ROC curve. This can be illustrated using the cross-validated ROC curve in FIG. 36. A pass/fail cut-off can be used to minimizes the false positive rate to an acceptably small level so that the cancer treatment is not unnecessarily modified. Supposing that 10% false-positives are acceptable then a cutoff of 1.9 gives a test sensitivity of about 55% correctly identified ASHA-significant hearing changes. Using this, or other appropriate criteria, such test failures can prompt the clinician to further audiological assessment.

Applying the ORA multivariate solution is relatively simple, requires no additional test time, and could be performed immediately following DPOAE data collection at each PV resulting in a clinically applicable interpretation of DPOAE change. The ORA has advantages over current univariate approaches used clinically, specifically greater accuracy and yields a probability of behavioral hearing change given DPOAE change.

In view of the many possible embodiments to which the principles of the disclosed invention may be applied, it should be recognized that the illustrated embodiments are only preferred examples of the invention and should not be taken as limiting the scope of the invention.

We claim:

1. A hearing monitoring system for monitoring hearing loss over a plurality of tests, comprising:
    an audio test unit configured to output one or more test sounds to an ear of a user during a respective hearing test, the audio test unit being configured to deliver the one or more test sounds at a plurality of test frequencies and at a plurality of stimulus levels; and
    a hearing test control system configured to display the plurality of test frequencies on a display screen and receive indications of a selection of respective ones of the plurality of test frequencies, the control system, upon receipt of an indication of a selected test frequency, causing the audio test unit to output one or more test sounds at the selected test frequency to an ear at one or more stimulus levels during the respective hearing test,
    wherein the control system is configured to receive an indication of whether the test sound was heard by the indicated ear at the selected test frequency and, for instances where the test sound was heard, storing the stimulus level for which the test sound was heard for respective hearing tests,
    wherein the control system is configured to store the highest set of test frequencies for which an indication was received that the test sound was heard by the indicated ear along with a baseline value related to the stimulus level at which the test sound was heard, the highest set of test frequencies for each ear being the sensitive range for ototoxicity for that respective ear for respective hearing tests,
    wherein the control system is configured to compare baseline values for the sensitive range for ototoxicity obtained during at least one prior hearing tests with those obtained from one or more subsequent hearing tests, and display on a display screen an indication of a change, if any, between prior baseline values and current baseline values for the sensitive range for ototoxicity and/or between a prior sensitive range for ototoxicity and the current sensitive range for ototoxicity.

2. The hearing monitoring system of claim 1, wherein the sensitive range for ototoxicity comprises a set of seven of the highest set of test frequencies for each ear.

3. The hearing monitoring system of claim 1, wherein the plurality of test frequencies comprise frequencies at 1/6 octave frequency steps.

4. The hearing monitoring system of claim 1, wherein the audio test unit and the control system comprise communication modules for delivering wireless signals from the control system to the audio test unit to cause the audio test unit to output the test sounds at the selected frequencies.

5. The hearing monitoring system of claim 1, further comprising a communication module for delivering signals over a network to a health care provider at a remote location.

6. The hearing monitoring system of claim 1, wherein the control system is configured to store a plurality of acoustic signatures for one or more of the plurality of test frequencies obtained during an acoustic calibration and verify the acoustic performance of the audio test unit by comparing one or more outputted test sounds with the acoustic signature recorded during the acoustic calibration.

7. The hearing monitoring system of claim 1, further comprising one or more microphones to measure ambient noise levels, the hearing monitoring system being configured to provide an indication if the measured ambient noise level exceeds a predetermined threshold value and the hearing monitoring system being configured to reduce and or reject ambient noise between the tympanic membrane and the transducer to a level that supports adequate signal to noise ratios suitable for audiological assessment.

* * * * *